US010195135B2

(12) United States Patent
Nakazono et al.

(10) Patent No.: US 10,195,135 B2
(45) Date of Patent: Feb. 5, 2019

(54) ORGANOPOLYSILOXANE GRAFT POLYMER

(71) Applicant: KAO CORPORATION, Tokyo (JP)

(72) Inventors: Satomi Nakazono, Wakayama (JP); Ryosuke Fujii, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/767,194

(22) PCT Filed: Nov. 11, 2013

(86) PCT No.: PCT/JP2013/080464
§ 371 (c)(1),
(2) Date: Aug. 11, 2015

(87) PCT Pub. No.: WO2014/125687
PCT Pub. Date: Aug. 21, 2014

(65) Prior Publication Data
US 2015/0374612 A1 Dec. 31, 2015

(30) Foreign Application Priority Data

Feb. 13, 2013 (JP) ................. 2013-026116

(51) Int. Cl.
| | | |
|---|---|---|
| *A61Q 5/06* | (2006.01) | |
| *A61K 8/893* | (2006.01) | |
| *C08F 283/12* | (2006.01) | |
| *C08F 290/14* | (2006.01) | |
| *A45D 7/06* | (2006.01) | |
| *C08G 77/442* | (2006.01) | |
| *C08G 77/445* | (2006.01) | |

(52) U.S. Cl.
CPC ............... *A61K 8/893* (2013.01); *A45D 7/06* (2013.01); *A61Q 5/06* (2013.01); *C08F 283/12* (2013.01); *C08F 290/148* (2013.01); *C08G 77/442* (2013.01); *C08G 77/445* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 5,032,460 A | 7/1991 | Kantner et al. | |
| 5,468,477 A | 11/1995 | Kumar et al. | |
| 5,811,109 A | 9/1998 | Cooper et al. | |
| 5,840,291 A | 11/1998 | Tsubakihara et al. | |
| 5,929,173 A * | 7/1999 | Midha ................... | A61K 8/895 424/78.17 |
| 5,973,068 A | 10/1999 | Yamaya et al. | |
| 6,106,820 A | 8/2000 | Morrissey et al. | |
| 6,458,906 B1 * | 10/2002 | Torgerson ................ | A61K 8/73 526/240 |
| 6,537,532 B1 * | 3/2003 | Torgerson .............. | A61K 8/898 424/70.1 |
| 9,351,920 B2 * | 5/2016 | Ohba ........................ | A61Q 5/06 |
| 2002/0015681 A1 | 2/2002 | Carballada et al. | |
| 2002/0081323 A1 | 6/2002 | Nakanishi et al. | |
| 2002/0098214 A1 | 7/2002 | Adams et al. | |
| 2010/0130693 A1 | 5/2010 | Yamada et al. | |
| 2010/0284957 A1 | 11/2010 | Yamada et al. | |
| 2012/0216823 A1 | 8/2012 | Fukuhara et al. | |

FOREIGN PATENT DOCUMENTS

| | | | |
|---|---|---|---|
| JP | 3-086775 | * | 4/1991 |
| JP | 3-086775 A | | 4/1991 |
| JP | 3-088815 A | | 4/1991 |
| JP | 6-092825 A | | 4/1994 |
| JP | 6-271436 A | | 9/1994 |
| JP | 8-003237 A | | 1/1996 |
| JP | 8-100035 A | | 4/1996 |
| JP | 9-157339 A | | 6/1997 |
| JP | 10-501219 A | | 2/1998 |
| JP | 10-512233 A | | 11/1998 |
| JP | 11-049984 A | | 2/1999 |
| JP | 2000-302828 A | | 10/2000 |
| JP | 2001-527559 A | | 12/2001 |
| JP | 2002-540071 A | | 11/2002 |
| JP | 2003-500504 A | | 1/2003 |
| JP | 2005-097494 A | | 4/2005 |
| JP | 2008-274116 A | | 11/2008 |
| JP | 2009-161598 A | | 7/2009 |
| WO | WO 2011/062210 A1 | | 5/2011 |

OTHER PUBLICATIONS

International Search Report issued in PCT/JP2013/080464, dated Feb. 4, 2014.

* cited by examiner

*Primary Examiner* — Jyothsna A Venkat
(74) *Attorney, Agent, or Firm* — Birch, Stewart, Kolasch & Birch, LLP

(57) ABSTRACT

The present invention relates to an organopolysiloxane graft polymer including an organopolysiloxane segment as a main chain thereof and an unsaturated monomer-derived copolymer segment containing a repeating unit derived from an unsaturated monomer containing a carboxylic acid or a carboxylic acid salt as a side chain thereof, in which a content of the organopolysiloxane segment in the organopolysiloxane graft polymer is 35 to 59% by mass, a content of the repeating unit derived from the unsaturated monomer containing a carboxylic acid or a carboxylic acid salt in the organopolysiloxane graft polymer is 4 to 17% by mass, and a content of a repeating unit derived from an unsaturated monomer whose homopolymer has a glass transition point of not lower than 150° C. (except for the unsaturated monomer containing a carboxylic acid or a carboxylic acid salt) in the organopolysiloxane graft polymer is not more than 14% by mass, and a number-average molecular weight of the organopolysiloxane segment is not less than 8,000 and not more than 200,000.

14 Claims, 2 Drawing Sheets

| Polymer C: After 1 hour from hair setting | Polymer D: After 1 hour from hair setting | Polymer E: After 1 hour from hair setting | Polymer F: After 1 hour from hair setting | Polymer R: After 1 hour from hair setting |
|---|---|---|---|---|
|  |  |  |  |  |

ORGANOPOLYSILOXANE GRAFT POLYMER

FIELD OF THE INVENTION

The present invention relates to an organopolysiloxane graft polymer, and more particularly, to an organopolysiloxane graft polymer that is useful as a hair cosmetic.

BACKGROUND OF THE INVENTION

Organopolysiloxanes have various excellent characteristics. Therefore, the organopolysiloxanes having various configurations have been used as a touch improver and the like which are compounded in shampoos, hair conditioners, etc.

For example, Patent Literature 1 aims at providing a hairdressing method that is capable of imparting a soft touch and a natural finish feeling to hair, firmly fixing a hair style, maintaining the hair style for a long period of time without change even when exposed to external factors (such as combing of hand or fingers through hair, wind, vibrations, etc.), and further hairdressing the hair again, and discloses a hair cosmetic containing a poly(N-acyl alkylene imine)-modified organopolysiloxane. In the invention of Patent Literature 1, there is described such a hairdressing method including the steps of applying the hair cosmetic containing a poly(N-acyl alkylene imine)-modified organopolysiloxane to hair, shaping the hair at a hair temperature of 50° C. or higher, and then cooling the hair to a temperature of lower than 50° C. to fix a style of the hair thus shaped.

Patent Literature 2 discloses a cosmetic composition containing a vinyl-silicone graft or block copolymer having a specific structure.

Patent Literature 3 discloses an anionic group-containing organopolysiloxane graft polymer treated powder, and personal care goods containing cosmetics using the powder.

Patent Literature 4 discloses cosmetics containing a grafted silicone polymer that contains a polymerization product of a mercapto-modified silicone polymer and a radical-polymerizable monomer component containing (meth)acrylic acid and/or a (meth)acrylic acid alkyl ester.

Patent Literature 5 discloses a temporary hair color composition containing an anionic resin in the form of a graft-type or an alternative block-type copolymer in which a constitutional unit constituted of a polysiloxane group and a constitutional unit constituted of a polymer of unsaturated monomers containing an anionic group-containing unsaturated monomer are bonded to each other through a sulfide bond, and a pigment.

Patent Literature 6 discloses a process for producing a silicone-vinyl copolymer by polymerizing a mercapto-functional silicone compound and a free radical-polymerizable monomer.

CITATION LIST

Patent Literature

Patent Literature 1: WO 2011/062210A
Patent Literature 2: JP 10-512233 A
Patent Literature 3: JP 2009-161598 A
Patent Literature 4: JP 2008-274116 A
Patent Literature 5: JP 6-271436 A
Patent Literature 6: JP 3-88815 A

SUMMARY OF THE INVENTION

The present invention relates to an organopolysiloxane graft polymer including an organopolysiloxane segment as a main chain thereof and an unsaturated monomer-derived copolymer segment containing a repeating unit derived from an unsaturated monomer containing a carboxylic acid or a carboxylic acid salt as a side chain thereof, in which a content of the organopolysiloxane segment in the organopolysiloxane graft polymer is not less than 35% by mass and not more than 59% by mass, a content of the repeating unit derived from the unsaturated monomer containing a carboxylic acid or a carboxylic acid salt in the organopolysiloxane graft polymer is not less than 4% by mass and not more than 17% by mass, and a content of a repeating unit derived from an unsaturated monomer whose homopolymer has a glass transition point of not lower than 150° C. (except for the unsaturated monomer containing a carboxylic acid or a carboxylic acid salt) in the organopolysiloxane graft polymer is not more than 14% by mass, and a number-average molecular weight of the organopolysiloxane segment is not less than 8,000 and not more than 200,000.

DETAILED DESCRIPTION OF THE INVENTION

Figure 1:
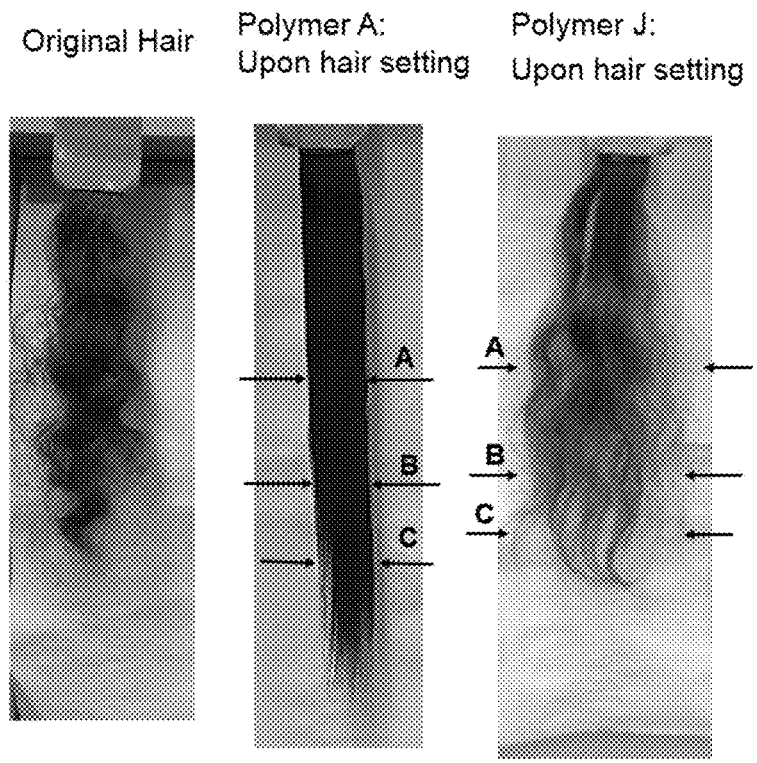
FIG. 1 is a view showing evaluation results of hair settability in Example 1 and Comparative Example 1 (polymers A and J).

As described above, there have been used organopolysiloxanes having various structures. The poly(N-acyl alkylene imine)-modified organopolysiloxane described in Patent Literature 1 fails to exhibit a sufficient hair set retentivity under high-humidity conditions. The anionic group-containing organopolysiloxane graft polymers described in Patent Literatures 2 to 6 are not applicable to a hairdressing method in which after shaping hair at a hair temperature of 50° C. or higher, the hair is then cooled to a temperature of lower than 50° C. to fix a style of the hair thus shaped (for example, upon setting hair using a hair iron or a dryer).

The present invention relates to an organopolysiloxane compound that has an excellent water dispersibility, is capable of fixing a style of hair shaped by shaping the hair at a hair temperature of 50° C. or higher and then cooling the hair to a temperature of lower than 50° C., and is excellent in hair set retentivity under high-humidity conditions as well as a touch feeling of hair after setting.

The present invention relates to an organopolysiloxane graft polymer, a process for producing the organopolysiloxane graft polymer, a hair cosmetic, a use of the organopolysiloxane graft polymer for a hair cosmetic, and a hairdressing method, as described below.

[1] An organopolysiloxane graft polymer including an organopolysiloxane segment as a main chain thereof and an unsaturated monomer-derived copolymer segment containing a repeating unit derived from an unsaturated monomer containing a carboxylic acid or a carboxylic acid salt as a side chain thereof, in which a content of the organopolysiloxane segment in the organopolysiloxane graft polymer is not less than 35% by mass and not more than 59% by mass, a content of the repeating unit derived from the unsaturated monomer containing a carboxylic acid or a carboxylic acid salt in the organopolysiloxane graft polymer is not less than 4% by mass and not more than 17% by mass, and a content of a repeating unit derived from an unsaturated monomer whose homopolymer has a glass transition point of not lower than 150° C. (except for the unsaturated monomer containing a carboxylic acid or a carboxylic acid salt) in the organopolysiloxane graft polymer is not more than 14% by mass, and a number-average molecular weight of the organopolysiloxane segment is not less than 8,000 and not more than 200,000.

[2] A process for producing an organopolysiloxane graft polymer including an organopolysiloxane segment as a main chain thereof and an unsaturated monomer-derived copolymer segment containing a repeating unit derived from an unsaturated monomer containing a carboxylic acid or a carboxylic acid salt as a side chain thereof, said process including the step of subjecting unsaturated monomers containing the unsaturated monomer containing a carboxylic acid or a carboxylic acid salt to polymerization in the presence of a radical-reactive organopolysiloxane represented by the following general formula (4) or (5):

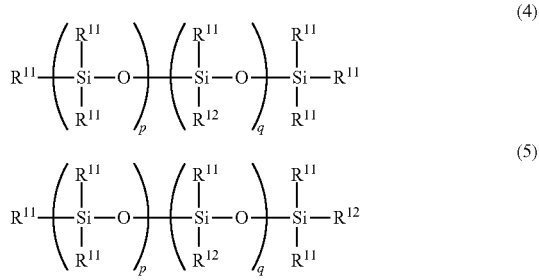

wherein $R^{11}$ groups are each independently an alkyl group having not less than 1 and not more than 22 carbon atoms or an aryl group having not less than 6 and not more than 14 carbon atoms; $R^{12}$ is an alkyl group containing a radical-reactive functional group; p is a number of not less than 2 and not more than 4,000; and q is a number of not less than 2 and not more than 250, in which repeating units in number of p and repeating units in number of q may be bonded to each other either in a block form or in a random form, in which a content of the organopolysiloxane segment in the organopolysiloxane graft polymer is not less than 35% by mass and not more than 59% by mass, a content of the repeating unit derived from the unsaturated monomer containing a carboxylic acid or a carboxylic acid salt in the organopolysiloxane graft polymer is not less than 4% by mass and not more than 17% by mass, and a content of a repeating unit derived from an unsaturated monomer whose homopolymer has a glass transition point of not lower than 150° C. (except for the unsaturated monomer containing a carboxylic acid or a carboxylic acid salt) in the organopolysiloxane graft polymer is not more than 14% by mass, and a number-average molecular weight of the organopolysiloxane segment is not less than 8,000 and not more than 200,000.

[3] A hair cosmetic including the organopolysiloxane graft polymer according to the above [1].

[4] A use of the organopolysiloxane graft polymer according to the above [1] for a hair cosmetic.

[5] A hairdressing method including the step of applying the organopolysiloxane graft polymer according to the above [1] to hair.

The organopolysiloxane graft polymer of the present invention has an excellent water dispersibility, is capable of fixing a style of hair shaped by shaping the hair at a hair temperature of 50° C. or higher and then cooling the hair to a temperature of lower than 50° C. (hereinafter also referred to as "hair settability"), exhibit a high hair set retentivity even under high-humidity conditions (hereinafter also referred to as "hair set retentivity under high-humidity conditions") as well as is excellent in touch feeling of hair without stiffness and stickiness (hereinafter also referred to as a "touch feeling of hair").

[Organopolysiloxane Graft Polymer]

The organopolysiloxane graft polymer according to the present invention (hereinafter also referred to merely as a "graft polymer of the present invention") includes an organopolysiloxane segment as a main chain thereof and an unsaturated monomer-derived copolymer segment containing a repeating unit derived from an unsaturated monomer containing a carboxylic acid or a carboxylic acid salt as a side chain thereof, in which a content of the organopolysiloxane segment in the organopolysiloxane graft polymer is not less than 35% by mass and not more than 59% by mass, a content of the repeating unit derived from the unsaturated monomer containing a carboxylic acid or a carboxylic acid salt in the organopolysiloxane graft polymer is not less than 4% by mass and not more than 17% by mass, and a content of a repeating unit derived from an unsaturated monomer whose homopolymer has a glass transition point of not lower than 150° C. (except for the unsaturated monomer containing a carboxylic acid or a carboxylic acid salt) in the organopolysiloxane graft polymer is not more than 14% by mass, and a number-average molecular weight of the organopolysiloxane segment is not less than 8,000 and not more than 200,000.

In the graft polymer of the present invention, it is preferred that two or more side chains are respectively bonded to optional silicon atoms in the organopolysiloxane segment constituting the main chain of the graft polymer through an alkylene group containing a hetero atom, and it is more preferred that the two or more side chains are respectively bonded to one or more silicon atoms except for those silicon atoms located at opposite ends of the organopolysiloxane segment through the alkylene group, and it is still more preferred that the two or more side chains are respectively bonded to two or more silicon atoms except for those silicon atoms located at opposite ends of the organopolysiloxane segment through the alkylene group.

<Organopolysiloxane Segment>

The graft polymer of the present invention contains the organopolysiloxane segment as a main chain thereof.

The chemical structure of the organopolysiloxane segment is not particularly limited. Specific Examples of the preferred organopolysiloxane segment include modified organopolysiloxane segments represented by the following general formula (1) or (2).

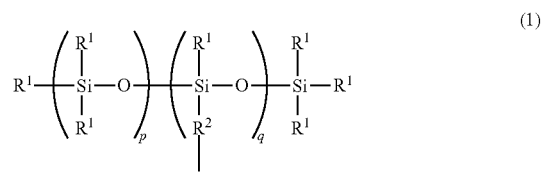

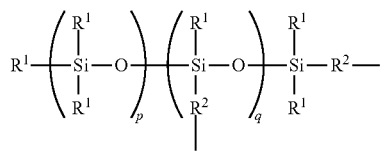

(2)

In the above general formulae (1) and (2), $R^1$ groups are each independently an alkyl group having not less than 1 and not more than 22 carbon atoms or an aryl group having not less than 6 and not more than 14 carbon atoms; and $R^2$ is an alkylene group that may contain a hetero atom. Also, p is a number of not less than 2 and not more than 4,000, and q is a number of not less than 2 and not more than 250. In the general formulae (1) and (2), the repeating units in the number of p and the repeating units in the number of q may be bonded to each other either in a block form or in a random form.

In the above general formulae (1) and (2), the alkyl group represented by $R^1$ is a straight-chain alkyl group, a branched-chain alkyl group or a cyclic alkyl group. The number of carbon atoms of the alkyl group represented by $R^1$ is preferably not less than 1 and not more than 10, more preferably not more than 6, and still more preferably not more than 3, from the viewpoint of a good water dispersibility of the graft polymer of the present invention. Specific examples of the alkyl group represented by $R^1$ include a methyl group, an ethyl group, an n-propyl group, an isopropyl group, an n-butyl group, a tert-butyl group, a pentyl group, a hexyl group, a cyclohexyl group, a heptyl group, an octyl group, a nonyl group, a decyl group, an undecyl group, a dodecyl group, an octadecyl group, a nonadecyl group, an eicosyl group and a docosyl group. Meanwhile, the water dispersibility of the graft polymer means such a property that the graft polymer can be stably dispersed in a composition containing water as a main component. When the graft polymer has a good water dispersibility, it is possible to compound the graft polymer in a hair cosmetic containing water a main solvent, so that the hair cosmetic can exhibit a good shampooing property.

The number of carbon atoms of the aryl group represented by $R^1$ is preferably not less than 6 and not more than 12, and more preferably not more than 9, from the viewpoint of a good water dispersibility of the graft polymer of the present invention. Specific examples of the aryl group represented by $R^1$ include a phenyl group, a tolyl group, a xylyl group, a naphthyl group, a biphenyl group, an anthryl group and a phenanthryl group.

Of these groups as $R^1$, from the viewpoints of a good water dispersibility of the graft polymer of the present invention and a high hair settability after setting hair using the hair cosmetic of the present invention, preferred are straight-chain or branched-chain alkyl groups having not less than 1 and not more than 6 carbon atoms, more preferred are straight-chain or branched-chain alkyl groups having not less than 1 and not more than 3 carbon atoms, and still more preferred is a methyl group.

In the above general formulae (1) and (2), p is a number of not less than 2 and not more than 4,000, and q is a number of not less than 2 and not more than 250.

From the viewpoints of a high hair settability after setting hair using the hair cosmetic of the present invention, a high hair set retentivity under high-humidity conditions and a good touch feeling of hair after setting, p is preferably a number of not less than 50, more preferably not less than 60, still more preferably not less than 80, and even still more preferably not less than 100, and from the viewpoints of a good water dispersibility of the graft polymer of the present invention and a good touch feeling of hair after setting, p is also preferably a number of not more than 1,500, more preferably not more than 1,300, still more preferably not more than 900, even still more preferably not more than 500, and further even still more preferably not more than 200.

From the viewpoint of a good water dispersibility of the graft polymer of the present invention, q is preferably a number of not less than 3, and from the viewpoints of a high hair settability of the hair cosmetic of the present invention and a high hair set retentivity under high-humidity conditions, q is also preferably a number of not more than 150, more preferably not more than 110, still more preferably not more than 70, even still more preferably not more than 20, and further even still more preferably not more than 10.

In the above general formulae (1) and (2), a part or whole of the alkylene groups ($R^2$) which may contain a hetero atom are bonded to both the main chain and the unsaturated monomer-derived copolymer segment to function as a connecting group between the main chain and the unsaturated monomer-derived copolymer segment as the side chain. In the case where any alkylene group that may contain a hetero atom is present in the form of a group unbonded to the unsaturated monomer-derived copolymer segment, the alkylene group that may contain a hetero atom is bonded to the main chain and a hydrogen atom.

In the present invention, the number of carbon atoms of the alkylene group that may contain a hetero atom is preferably not less than 2, and more preferably not less than 3, from the viewpoint of a good availability of the raw materials upon production of the graft polymer of the present invention. Also, from the viewpoint of a good water dispersibility of the graft polymer of the present invention, the number of carbon atoms of the alkylene group that may contain a hetero atom is preferably not more than 20, more preferably not more than 10, and still more preferably not more than 8.

In the present invention, the alkylene group that may contain a hetero atom may be interrupted by at least one atom or functional group selected from the group consisting of an oxygen atom, a sulfur atom, —NH—, —COO—, —NHCO— and —NR³CO—. That is, the alkylene group that may contain a hetero atom may have a structure constituted of "-(an alkylene group portion 1)-(the above atom or functional group)-(an alkylene group portion 2)". In this case, the number of carbon atoms of the alkylene group means a sum of the number of carbon atoms of the alkylene group portion 1 and the number of carbon atoms of the alkylene group portion 2. In the above —NR³CO—, $R^3$ is an alkyl group having not less than 1 and not more than 3 carbon atoms. When the alkylene group that may contain a hetero atom is interrupted by the above atom or functional group, from the viewpoint of facilitated production of the graft polymer of the present invention, the alkylene group that may contain a hetero atom is preferably interrupted by —NHCO—.

In the present invention, the alkylene group that may contain a hetero atom may be substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having 2 to 4 carbon atoms, a carboxy group, and a ($C_1$-$C_3$) alkyl ester group. In this case, the number of carbon atoms of the alkylene group that may contain a hetero atom does not include the number of carbon atoms contained in the above substituent group. From the viewpoint of a good availability of the raw materials upon production of the graft polymer of the present invention, the alkylene group that may contain a hetero atom is preferably substituted with at least one monovalent group selected from the group consisting of an acetamide group, a ($C_1$-$C_3$) alkyl amino group and an amino group.

In the present invention, the alkylene group that may contain a hetero atom may be substituted with a divalent hetero atom or a divalent group containing a hetero atom which is selected from the group consisting of —O—, —S—, —NH—, —$NR^{14}$—, and —COO—, in which $R^{14}$ is a ($C_1$-$C_3$) alkyl group that may be substituted with a dimethyl amino group. The divalent hetero atom or the divalent group containing a hetero atom is bonded to the unsaturated monomer-derived polymer segment in the case where the alkylene group that may contain a hetero atom functions as a connecting group to the unsaturated monomer-derived polymer segment, and in otherwise cases, the divalent hetero atom or the divalent group containing a hetero atom is bonded to a hydrogen atom.

From the viewpoint of facilitated production of the graft polymer of the present invention, the alkylene group that may contain a hetero atom is preferably substituted with —S—.

The alkylene group ($R^2$) which may contain a hetero atom is preferably bonded to the unsaturated monomer-derived polymer segment through the hetero atom, more preferably through a nitrogen atom, an oxygen atom or a sulfur atom, and still more preferably through a sulfur atom.

Therefore, the "alkylene group that may contain a hetero atom" represented by $R^2$ corresponds to (i) an unsubstituted alkylene group; (ii) an alkylene group interrupted by at least one atom or functional group selected from the group consisting of an oxygen atom, a sulfur atom, —NH—, —COO—, —NHCO—, and —$NR^3$CO—; (iii) an alkylene group substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having 2 to 4 carbon atoms, a carboxy group, and a ($C_1$-$C_3$) alkyl ester group; (iv) an alkylene group substituted with a divalent hetero atom or a divalent group containing a hetero atom which is selected from the group consisting of —O—, —S—, —NH—, —$NR^{14}$—, and —COO—; and an alkylene group in the form of a combination of the above (ii), (iii) and (iv).

Specific examples of the alkylene group that may contain a hetero atom as used in the present invention include those group represented by the following formulae (i) to (xii). Of these groups, from the viewpoint of facilitated production of the graft polymer of the present invention, preferred are those groups represented by the following formulae (xi) and (xii).

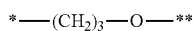

(i)

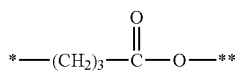

(ii)

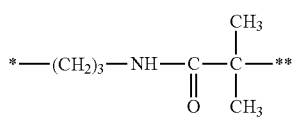

(iii)

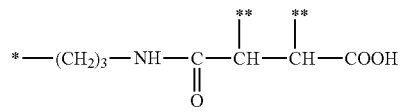

(iv)

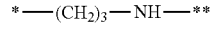

(v)

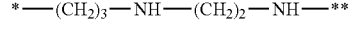

(vi)

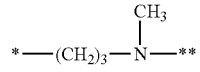

(vii)

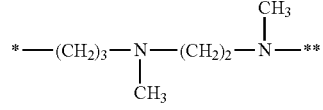

(viii)

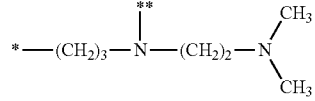

(ix)

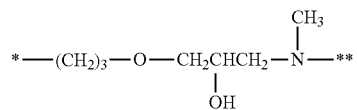

(x)

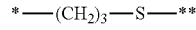

(xi)

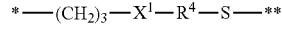

(xii)

In the formulae (i) to (xii), "*" represents a moiety bonded to the silicon atom in the general formula (1) or (2), whereas "**" represents a moiety bonded to the unsaturated monomer-derived copolymer segment.

In the formula (xii), $X^1$ is at least one group selected from the group consisting of —O—, —OCO—, —COO—, —CONH—, and —NHCO—. Of these groups, from the viewpoint of facilitated production of the graft polymer of the present invention, preferred are —CONH— and —NHCO—, and more preferred is —NHCO—.

Also, in the formula (xii), $R^4$ is an alkylene group that may be substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having 2 to 4 carbon atoms, a carboxy group, and a ($C_1$-$C_3$) alkyl ester group. Of these substituent groups, from the viewpoint of a good availability of the raw materials upon production of the graft polymer, preferred are an acetamide group, a ($C_1$-$C_3$) alkyl amino group and an amino group. The number of carbon atoms of the alkylene group represented by $R^4$ is preferably not less than 2, and more preferably not less than 3, from the viewpoint of facilitated production of the graft polymer of the present invention, and is also preferably not more than 10, and more preferably not more than 6, from the viewpoint of a good water dispersibility of the graft polymer of the present invention.

Specific examples of $R^4$ include those groups represented by the following formulae (xiii) to (xiv).

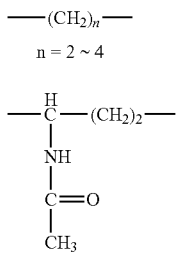

The content of the organopolysiloxane segment in the graft polymer of the present invention is not less than 35% by mass, preferably not less than 38% by mass, more preferably not less than 40% by mass, and still more preferably not less than 45% by mass, from the viewpoint of a good touch feeling of hair after setting the hair using the hair cosmetic of the present invention, and is also not more than 59% by mass, preferably not more than 55% by mass, and more preferably not more than 50% by mass, from the viewpoints of a good water dispersibility of the graft polymer of the present invention, a high hair settability after setting the hair using the hair cosmetic of the present invention, and a high hair set retentivity under high-humidity conditions.

In the case where the graft polymer of the present invention is produced from the below-mentioned radical-reactive organopolysiloxane, the content of the organopolysiloxane segment in the graft polymer of the present invention may be determined from a "total mass (c) of the radical-reactive organopolysiloxane charged upon production of the graft polymer" and a "total mass (d) of the unsaturated monomers charged upon production of the graft polymer".

<Unsaturated Monomer-Derived Copolymer Segment>

The graft polymer of the present invention includes the unsaturated monomer-derived copolymer segment containing the repeating unit derived from the unsaturated monomer containing a carboxylic acid or a carboxylic acid salt as a side chain thereof. The repeating unit derived from the unsaturated monomer as used in the present invention means a repeating unit formed upon polymerization of the unsaturated monomer.

From the viewpoints of a good water dispersibility of the graft polymer of the present invention, a high hair settability after setting the hair using the hair cosmetic of the present invention, and a high hair set retentivity under high-humidity conditions, the content of the unsaturated monomer-derived copolymer segment in the graft polymer of the present invention is not less than 41% by mass, preferably not less than 45% by mass, and more preferably not less than 50% by mass. Also, from the viewpoint of a good touch feeling of hair after setting the hair using a hair cosmetic containing the organopolysiloxane graft polymer of the present invention, the content of the unsaturated monomer-derived copolymer segment in the graft polymer of the present invention is not more than 65% by mass, preferably not more than 62% by mass, more preferably not more than 60% by mass, and still more preferably not more than 55% by mass.

From the viewpoints of a good water dispersibility of the graft polymer of the present invention and a good touch feeling of hair after setting, the content of the repeating unit derived from the unsaturated monomer containing a carboxylic acid or a carboxylic acid salt in the graft polymer of the present invention is not less than 4% by mass, preferably not less than 4.5% by mass, and more preferably not less than 8% by mass. Also, from the viewpoints of a high hair settability after setting the hair using the hair cosmetic of the present invention and a high hair set retentivity under high-humidity conditions, the content of the repeating unit derived from the unsaturated monomer containing a carboxylic acid or a carboxylic acid salt in the graft polymer of the present invention is not more than 17% by mass, preferably not more than 14% by mass, more preferably not more than 11% by mass, and still more preferably not more than 9% by mass.

From the viewpoints of a good water dispersibility of the graft polymer of the present invention and a good touch feeling of hair after setting, the content of the repeating unit derived from the unsaturated monomer containing a carboxylic acid or a carboxylic acid salt in the unsaturated monomer-derived copolymer segment is not less than 6% by mass, preferably not less than 10% by mass, and more preferably not less than 17% by mass. Also, from the viewpoints of a high hair settability after setting the hair using the hair cosmetic of the present invention and a high hair set retentivity under high-humidity conditions, the content of the repeating unit derived from the unsaturated monomer containing a carboxylic acid or a carboxylic acid salt in the unsaturated monomer-derived copolymer segment is not more than 41% by mass, preferably not more than 30% by mass, more preferably not more than 25% by mass, and still more preferably not more than 18% by mass.

In the case where the graft polymer of the present invention is produced from the below-mentioned radical-reactive organopolysiloxane, the content of the repeating unit derived from the unsaturated monomer containing a carboxylic acid or a carboxylic acid salt in the graft polymer of the present invention or in the unsaturated monomer-derived copolymer segment may be determined from a "total mass (c) of the radical-reactive organopolysiloxane charged upon production of the graft polymer", a "total mass (d) of the unsaturated monomers charged upon production of the graft polymer" and a "total mass of the unsaturated monomer containing a carboxylic acid or a carboxylic acid salt charged upon production of the graft polymer".

Specific examples of the unsaturated monomer containing a carboxylic acid or a carboxylic acid salt include unsaturated carboxylic acid monomers such as (meth)acrylic acid, maleic acid, maleic anhydride, itaconic acid, fumaric acid and crotonic acid. Of these unsaturated monomers, from the viewpoint of a good availability, preferred are (meth)acrylic acid and maleic acid, and more preferred is (meth)acrylic acid.

The repeating unit derived from the unsaturated monomer containing a carboxylic acid may be in the form of an acid as such, or may be in the form of a partially or wholly neutralized product. Specific examples of a base compound used for the neutralization include alkali metal hydroxides such as lithium hydroxide, potassium hydroxide and sodium hydroxide; ammonia; and amine compounds such as mono-, di- or triethanol amine, triethylamine, morpholine, aminomethyl propanol and aminoethyl propanediol. Of these base compounds, from the viewpoint of a good water dispersibility of the graft polymer of the present invention, the repeating unit derived from the unsaturated monomer containing a carboxylic acid is preferably in the form of a partially or wholly neutralized product.

In the present invention, the unsaturated monomer-derived copolymer segment containing the repeating unit derived from the unsaturated monomer containing a carboxylic acid or a carboxylic acid salt contains a repeating unit derived from an unsaturated monomer that is copolymerizable with the unsaturated monomer containing a carboxylic acid or a carboxylic acid salt (hereinafter also referred to as a "copolymerizable monomer") in addition to the repeating unit derived from the unsaturated monomer containing a carboxylic acid or a carboxylic acid salt.

The copolymerizable monomer is not particularly limited as long as the monomer can be copolymerized with the unsaturated monomer containing a carboxylic acid or a carboxylic acid salt, and is a monomer other than the unsaturated monomer containing a carboxylic acid or a carboxylic acid salt. The copolymerizable monomer is preferably an unsaturated monomer containing no ionic group. Examples of the copolymerizable monomer include olefins, halogenated olefins, vinyl esters, (meth)acrylic acid esters, and (meth)acrylamides.

Specific examples of the olefins include ethylene, propylene and isobutylene. Specific examples of the halogenated olefins include vinyl chloride, vinyl fluoride, vinylidene chloride and vinylidene fluoride. Specific examples of the vinyl esters include vinyl formate, vinyl acetate, vinyl propionate and vinyl versatate.

Specific examples of the (meth)acrylic acid esters include methyl (meth)acrylate, ethyl (meth)acrylate, propyl (meth)acrylate, butyl(meth)acrylate, hexyl (meth)acrylate, octyl (meth)acrylate, 2-ethylhexyl (meth)acrylate, decyl (meth)acrylate, dodecyl (meth)acrylate, cyclohexyl (meth)acrylate, 2-hydroxyethyl (meth)acrylate, polyethylene glycol (meth)acrylate, and polyethylene glycol monomethyl ether (meth)acrylate.

Specific examples of the (meth)acrylamides include (meth)acrylamide, N-dimethyl (meth)acrylamide, N,N-diethyl (meth)acrylamide, N-isopropyl (meth)acrylamide, N-butyl (meth)acrylamide, diacetone (meth)acrylamide, N-cyclohexyl (meth)acrylamide, N-tert-octyl (meth)acrylamide, N-methylol (meth)acrylamide and N,N-dimethylaminopropyl (meth)acrylamide.

The repeating unit derived from any of these copolymerizable monomers may be present as a single kind thereof in the graft polymer of the present invention, or may be present in the form of a mixture of plural kinds thereof in the graft polymer of the present invention.

Of these copolymerizable monomers, from the viewpoints of a high hair settability after setting the hair using the hair cosmetic of the present invention and a high hair set retentivity under high-humidity conditions, preferred is at least one monomer selected from the group consisting of the aforementioned (meth)acrylamides and (meth)acrylic acid esters; more preferred is at least one monomer selected from the group consisting of N-t-butyl (meth)acrylamide, N-i-butyl (meth)acrylamide, polyethylene glycol (9) monomethyl ether (meth)acrylate, polyethylene glycol (2) monomethyl ether (meth)acrylate, polyethylene glycol (4) monomethyl ether (meth)acrylate, polyethylene glycol (23) monomethyl ether (meth)acrylate, polyethylene glycol (90) monomethyl ether (meth)acrylate, polyethylene glycol (2) (meth)acrylate, polyethylene glycol (4.5) (meth)acrylate, polyethylene glycol (8) (meth)acrylate, polyethylene glycol (10) (meth)acrylate, dodecyl (meth)acrylate, t-butyl (meth)acrylate and i-butyl (meth)acrylate; still more preferred is at least one monomer selected from the group consisting of N-t-butyl (meth)acrylamide, N-i-butyl (meth)acrylamide and polyethylene glycol (9) monomethyl ether (meth)acrylate; even still more preferred is at least one monomer selected from the group consisting of N-t-butyl (meth)acrylamide and polyethylene glycol (9) monomethyl ether (meth)acrylate; and further even still more preferred is combination of N-t-butyl (meth)acrylamide and polyethylene glycol (9) monomethyl ether (meth)acrylate.

The unsaturated monomer-derived copolymer segment containing the repeating unit derived from the unsaturated monomer containing a carboxylic acid or a carboxylic acid salt may be in the form of either a random copolymer or a block copolymer.

The content of the repeating unit derived from the copolymerizable monomer in the graft polymer of the present invention is preferably not less than 24% by mass, and more preferably not less than 28% by mass, from the viewpoints of a high hair settability after setting the hair using the hair cosmetic of the present invention and a high hair set retentivity under high-humidity conditions, and is also preferably not more than 61% by mass, and more preferably not more than 55% by mass, from the viewpoints of a good touch feeling of hair after setting and a good water dispersibility of the graft polymer of the present invention.

Also, the content of the repeating unit derived from the copolymerizable monomer in the unsaturated monomer-derived copolymer segment is preferably not less than 59% by mass, more preferably not less than 65% by mass, still more preferably not less than 70% by mass, and even still more preferably not less than 82% by mass, from the viewpoints of a high hair settability after setting the hair using the hair cosmetic of the present invention and a high hair set retentivity under high-humidity conditions, and is also preferably not more than 94% by mass, more preferably not more than 90% by mass, and still more preferably not more than 83% by mass, from the viewpoints of a good touch feeling of hair after setting and a good water dispersibility of the graft polymer of the present invention.

In the case where the graft polymer of the present invention is produced from the below-mentioned radical-reactive organopolysiloxane, the content of the repeating unit derived from the copolymerizable monomer in the graft polymer of the present invention or in the unsaturated monomer-derived copolymer segment may be determined from a "total mass (c) of the radical-reactive organopolysiloxane charged upon production of the graft polymer", a "total mass (d) of the unsaturated monomers charged upon production of the graft polymer" and a "total mass of the copolymerizable monomer charged upon production of the graft polymer".

As described above, the copolymerizable monomer is not particularly limited as long as the monomer can be copolymerized with the unsaturated monomer containing a carboxylic acid or a carboxylic acid salt, and is a monomer other than the unsaturated monomer containing a carboxylic acid or a carboxylic acid salt. From the viewpoint of facilitated shaping of hair at a hair temperature of not lower than 50° C., the content of a repeating unit derived from an unsaturated monomer whose homopolymer has a glass transition point (Tg) of not lower than 150° C. (except for the unsaturated monomer containing a carboxylic acid or a carboxylic acid salt) in the graft polymer of the present invention is not more than 14% by mass, preferably not more than 12% by mass, more preferably not more than 10% by mass, and still more preferably not more than 5% by mass. In the present invention, Tg of the homopolymer produced from the unsaturated monomer (hereinafter also referred to "Tg for unsaturated monomer") means Tg as described in "Polymer Handbook", 4th Edition, Vol. 1, VI/193-VI/277, published by Wiley-Interscience.

Specific examples of the unsaturated monomer having Tg for unsaturated monomer of not lower than 150° C. (except for the unsaturated monomer containing a carboxylic acid or a carboxylic acid salt) include adamantyl acrylate, adamantyl crotonate, 3,5-dimethyl adamantyl crotonate, ferrocenyl ethyl acrylate, ferrocenyl methyl acrylate, pentabromobenzyl acrylate, acrylamide, N-methyl, N-phenyl acrylamide, adamantyl methacrylate, cyanophenyl methacrylate, 3,5-dimethyl adamantyl methacrylate, ferrocenyl methyl methacrylate, isobornyl methacrylate, N-tert-butyl methacrylamide, N-carboxyphenyl methacrylamide, 3-(4-biphenylyl) styrene, 4-(4-biphenylyl) styrene, 2-carboxystyrene, 2,5-diisopropyl styrene, 2,4-diisopropyl styrene, α-methyl styrene, 2-methyl styrene, perfluorostyrene, 2-phenylaminocarboxystyrene, 4-phenyl styrene, methoxyethylene, 4-vinyl phenyl, N-carbazoyl ethylene, ferrocenyl ethylene, phthalimide ethylene, 4-pyridyl ethylene and N-vinyl pyrrolidone.

In the case where the graft polymer of the present invention is produced from the below-mentioned radical-reactive organopolysiloxane, the content of the repeating unit derived from the unsaturated monomer whose homopolymer has a glass transition point (Tg) of not lower than 150° C. in the graft polymer of the present invention may be determined from a "total mass (c) of the radical-reactive organopolysiloxane charged upon production of the graft polymer", a "total mass (d) of the unsaturated monomers charged upon production of the graft polymer", and a "total mass of the unsaturated monomer having Tg for unsaturated monomer of not lower than 150° C. charged upon production of the graft polymer".

In addition, from the viewpoints of a good water dispersibility of the graft polymer of the present invention, a high hair settability upon setting the hair using the hair cosmetic of the present invention, a high hair set retentivity under high-humidity conditions and a good touch feeling of hair after setting, the mass ratio (a/b) of the organopolysiloxane segment (a) to the unsaturated monomer-derived copolymer segment (b) is preferably not less than 35/65, more preferably not less than 38/62, still more preferably not less than 40/60, and even still more preferably not less than 45/55, and is also preferably not more than 59/41, more preferably not more than 55/45, and still more preferably not more than 50/50.

Meanwhile, in the present specification, in the case where the graft polymer of the present invention is produced from the below-mentioned radical-reactive organopolysiloxane, the above mass ratio (a/b) is regarded as being the same as a ratio (c/d) of a "total mass (c) of the radical-reactive organopolysiloxane charged upon production of the graft polymer" to a "total mass (d) of the unsaturated monomers charged upon production of the graft polymer" (the following formula (I)).

$$a/b = c/d \quad (I)$$

Meanwhile, in the case where the graft polymer of the present invention is produced from the below-mentioned radical-reactive organopolysiloxane, the resulting polymer may be in the form of a mixture of the organopolysiloxane graft polymer and a copolymer derived from an unsaturated monomer not bonded to the organopolysiloxane graft polymer. In the present invention, such a mixture is regarded as the organopolysiloxane graft polymer of the present invention.

The number-average molecular weight (MNg) of the organopolysiloxane segment being present between the adjacent unsaturated monomer-derived copolymer segments (hereinafter also referred to merely as a "molecular weight between graft points") is preferably not less than 500, more preferably not less than 700, and still more preferably not less than 1000, from the viewpoints of a high hair settability upon setting the hair with a hair cosmetic containing the organopolysiloxane graft polymer of the present invention and a high hair set retentivity under high-humidity conditions, and is also preferably not more than 30,000, more preferably not more than 20,000, and still more preferably not more than 4,000, from the viewpoint of a good water dispersibility of the graft polymer of the present invention.

The "organopolysiloxane segment being present between the adjacent unsaturated monomer-derived copolymer segments" as used herein means a portion surrounded by a broken line as shown in the following formula which is located between a bonding point (bonding point A) at which the unsaturated monomer-derived copolymer segment is bonded to the organopolysiloxane segment and a bonding point (bonding point B) at which the unsaturated monomer-derived copolymer segment adjacent to the above copolymer segment is bonded to the organopolysiloxane segment, and is constituted of one $R^1$SiO unit, one $R^2$ group and $R^{12}$SiO units in the number of y+1.

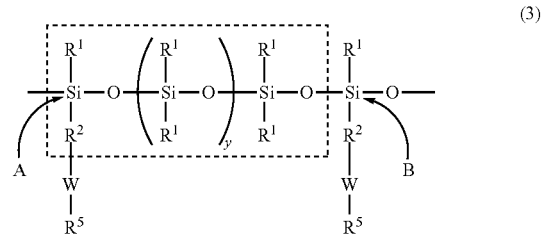

wherein $R^1$ groups are each independently an alkyl group having not less than 1 and not more than 22 carbon atoms or an aryl group having not less than 6 and not more than 14 carbon atoms; $R^2$ is an alkylene group that may contain a hetero atom; —W—$R^5$ is an unsaturated monomer-derived copolymer segment in which $R^5$ is a residue of a polymerization initiator or a hydrogen atom; and y is a positive number.

The molecular weight between graft points may be determined by the method described in Examples below.

The molecular weight between graft points is an average value of molecular weights of the portions surrounded by a broken line in the above formula, and may be construed as a mass (g/mol) of the organopolysiloxane segment per one mole of the unsaturated monomer-derived copolymer segment. In the case where the graft polymer of the present invention is produced from the below-mentioned radical-reactive organopolysiloxane, and all of the radical-reactive functional groups are bonded to the unsaturated monomer-derived copolymer segment, the molecular weight between graft points is also regarded as being identical to an inverse number of a molar number (mol/g) of the radical-reactive functional groups that are present per a unit mass of the radical-reactive organopolysiloxane.

In addition, the number-average molecular weight (MNx) of the organopolysiloxane segment constituting the main chain of the graft polymer is preferably not less than 8,000, more preferably not less than 10,000, still more preferably not less than 11,000, and even still more preferably not less than 12,000, from the viewpoints of a high hair settability upon setting the hair using a hair cosmetic containing the organopolysiloxane graft polymer of the present invention, a high hair set retentivity under high-humidity conditions and a good touch feeling of hair after setting. Also, MNx is not more than 200,000, preferably not more than 100,000, more preferably not more than 50,000, and still more preferably not more than 30,000, from the viewpoints of a good water dispersibility of the graft polymer of the present invention and a good touch feeling of hair after setting.

In the case where the organopolysiloxane graft polymer of the present invention is produced from the below-mentioned radical-reactive organopolysiloxane, the organopolysiloxane segment has a skeleton common to that of the radical-reactive organopolysiloxane, and therefore MNx is substantially the same as a number-average molecular weight of the radical-reactive organopolysiloxane. For this reason, in the present invention, MNx is regarded as being the same as the number-average molecular weight of the radical-reactive organopolysiloxane. Meanwhile, the number-average molecular weight of the radical-reactive organopolysiloxane is the value in terms of polystyrene as measured by GPC under the measuring conditions described in Examples below.

The number-average molecular weight (MNy) of the respective unsaturated monomer-derived copolymer segments in the organopolysiloxane graft polymer of the present invention is preferably not less than 500, more preferably not less than 1,000, and still more preferably not less than 1,500, from the viewpoints of a high hair settability upon setting the hair using the hair cosmetic of the present invention, a high hair set retentivity under high-humidity conditions and a good touch feeling of hair after setting. Also, MNy is preferably not more than 50,000, more preferably not more than 30,000, and still more preferably not more than 6,000, from the viewpoints of facilitated production of the graft polymer of the present invention and a good touch feeling of hair after setting. Meanwhile, MNy is the value as measured by the method described in Examples below.

The number-average molecular weight (MNt) of the graft polymer of the present invention is preferably not less than 10,000, more preferably not less than 14,000, and still more preferably not less than 20,000, from the viewpoints of a high hair settability upon setting the hair using a hair cosmetic containing the organopolysiloxane graft polymer of the present invention, a high hair set retentivity under high-humidity conditions and a good touch feeling of hair after setting. Also, MNt is preferably not more than 300,000, more preferably not more than 250,000, still more preferably not more than 100,000, and even still more preferably not more than 50,000, from the viewpoint of a good water dispersibility of the graft polymer of the present invention.

In the case where the graft polymer of the present invention is produced from the below-mentioned radical-reactive organopolysiloxane, MNt is determined from a number-average molecular weight of the radical-reactive organopolysiloxane as the raw material compound and the above mass ratio (a/b).

In the graft polymer of the present invention, from the viewpoint of a good touch feeling of hair after setting the hair using the hair cosmetic of the present invention, it is preferred that the content of the organopolysiloxane segment therein is not less than 45% by mass and not more than 59% by mass, the content of the repeating unit derived from the unsaturated monomer containing a carboxylic acid or a carboxylic acid salt therein is not less than 4% by mass and not more than 9% by mass, and the content of the repeating unit derived from the copolymerizable monomer therein is not less than 32% by mass and not more than 51% by mass, and it is more preferred that the content of the organopolysiloxane segment therein is not less than 50% by mass and not more than 59% by mass, the content of the repeating unit derived from the unsaturated monomer containing a carboxylic acid or a carboxylic acid salt therein is not less than 5% by mass and not more than 7% by mass, and the content of the repeating unit derived from the copolymerizable monomer therein is not less than 34% by mass and not more than 45% by mass.

In the graft polymer of the present invention, from the viewpoint of a good water dispersibility of the graft polymer of the present invention, it is preferred that the content of the organopolysiloxane segment therein is not less than 45% by mass and not more than 59% by mass, the content of the repeating unit derived from the unsaturated monomer containing a carboxylic acid or a carboxylic acid salt therein is not less than 8% by mass and not more than 17% by mass, and the content of the repeating unit derived from the copolymerizable monomer therein is not less than 24% by mass and not more than 47% by mass, and it is more preferred that the content of the organopolysiloxane segment therein is not less than 50% by mass and not more than 59% by mass, the content of the repeating unit derived from the unsaturated monomer containing a carboxylic acid or a carboxylic acid salt therein is not less than 10% by mass and not more than 15% by mass, and the content of the repeating unit derived from the copolymerizable monomer therein is not less than 26% by mass and not more than 40% by mass.

<Process for Producing Organopolysiloxane Graft Polymer>

Next, the process for producing the graft polymer of the present invention is described. The process for producing the graft polymer of the present invention is not particularly limited. For example, there may be used (i) a graft-onto method (polymer reaction method) in which an organopolysiloxane containing a reactive functional group is reacted with an unsaturated monomer-derived copolymer segment containing the repeating unit derived from the unsaturated monomer containing a carboxylic acid or a carboxylic acid salt which contains a functional group capable of reacting with the reactive functional group at a terminal end thereof; (ii) a graft-from method in which unsaturated monomers including the unsaturated monomer containing a carboxylic acid or a carboxylic acid salt are subjected to radical polymerization in the presence of the below-mentioned radical-reactive organopolysiloxane; or the like. Of these methods, from the viewpoint of reducing a burden upon production of the graft polymer, preferred is (ii) the graft-from method in which unsaturated monomers including the unsaturated monomer containing a carboxylic acid or a carboxylic acid salt are subjected to radical polymerization in the presence of the radical-reactive organopolysiloxane.

In the following, the process for producing the graft polymer of the present invention by the graft-from method is described.

<Radical-Reactive Organopolysiloxane>

The graft polymer of the present invention can be produced by subjecting the unsaturated monomers to radical polymerization in the presence of the radical-reactive organopolysiloxane represented by the following general formula (4) or (5).

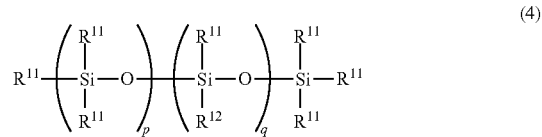

(4)

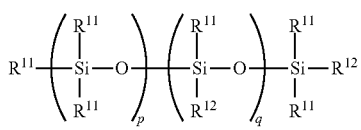

wherein $R^{11}$ groups are each independently an alkyl group having not less than 1 and not more than 22 carbon atoms or an aryl group having not less than 6 and not more than 14 carbon atoms; and $R^{12}$ is an alkyl group containing a radical-reactive functional group (hereinafter also referred to as a "radical-reactive group-containing alkyl group").

The preferred form of $R^{11}$ in the above general formulae (4) and (5) is the same as the preferred form of $R^1$ in the above general formulae (1) and (2).

The suffixes p and q in the above general formulae (4) and (5) have the same meanings as p and q in the above general formulae (1) and (2), and the preferred forms of p and q in the above general formulae (4) and (5) are the same as the preferred forms of p and q in the above general formulae (1) and (2).

The radical-reactive functional group as used in the present invention means a functional group capable of generating a radical. Examples of the radical-reactive functional group include an ethylenically unsaturated group, a halogeno group such as a chloro group and a bromo group, and a sulfanyl group (mercapto group). Of these functional groups, a sulfany group is preferred from the viewpoints of a high reactivity with the unsaturated monomers and a well-controlled molecular weight of the resulting polymer.

In the above general formulae (4) and (5), the radical-reactive group-containing alkyl group represented by $R^{12}$ may be substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having not less than 2 and not more than 4 carbon atoms, a carboxy group, and a ($C_1$-$C_3$) alkyl ester group. Of these monovalent substituent groups, from the viewpoint of a good availability of the raw materials upon production of the radical-reactive organopolysiloxane, preferred are an acetamide group, a ($C_1$-$C_3$) alkyl amino group and an amino group.

In the above general formulae (4) and (5), the number of carbon atoms of the radical-reactive group-containing alkyl group represented by $R^{12}$ is preferably not less than 2, and more preferably not less than 3, from the viewpoint of a good availability of the radical-reactive organopolysiloxane, and is also preferably not more than 20, more preferably not more than 10, and still more preferably not more than 8, from the viewpoint of a good water dispersibility of the graft polymer of the present invention.

Meanwhile, in the present invention, the number of carbon atoms of the radical-reactive group-containing alkyl group does not include the number of carbon atoms of the radical-reactive functional group even though the radical-reactive functional group contains any carbon atoms, and also does not include the number of carbon atoms of the above monovalent substituent group even though the radical-reactive group-containing alkyl group is substituted with the monovalent substituent group.

In the above general formulae (4) and (5), the radical-reactive group-containing alkyl group represented by $R^{12}$ may be interrupted by at least one atom or functional group selected from the group consisting of an oxygen atom, a sulfur atom, —NH—, —OCO—, —NHCO— and —$NR^{13}$CO—. In the above —$NR^{13}$CO—, $R^{13}$ is an alkyl group having not less than 1 and not more than 3 carbon atoms. When the radical-reactive group-containing alkyl group is interrupted by the above atom or functional group, from the viewpoints of a good availability and facilitated production of the radical-reactive organopolysiloxane, the radical-reactive group-containing alkyl group is preferably interrupted by —NHCO—.

Specific examples of the radical-reactive group-containing alkyl group used in the present invention include those groups represented by the following formulae (xvii) to (xx). Of these groups, from the viewpoints of facilitated production and a good availability of the radical-reactive organopolysiloxane, preferred are those groups represented by the following formula (xix) or (xx). $X^{11}$ and $R^{14}$ in the formula (xx) as well as the preferred forms thereof are the same as $X^1$ and $R^4$ in the formula (xii) as well as the preferred forms thereof.

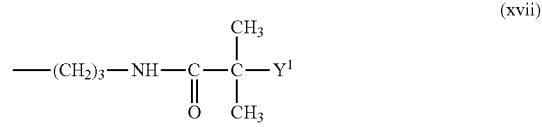

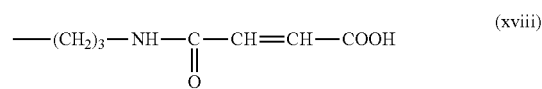

In the present invention, the number-average molecular weight of the radical-reactive organosiloxane is regarded as being the same as MNx, and therefore the preferred form of the number-average molecular weight of the radical-reactive organosiloxane is the same as the preferred form of MNx.

Meanwhile, the number-average molecular weight of the radical-reactive organosiloxane used in the present invention is the value in terms of polystyrene as measured by GPC under the measuring conditions described in Examples below.

The number of moles of the radical-reactive functional group being present per a unit mass of the radical-reactive organopolysiloxane is preferably not more than 1/500 mol/g, more preferably not more than 1/700 mol/g, still more preferably not more than 1/1,000 mol/g, and even still more preferably not more than 1/1,500 mol/g, from the viewpoints of a high hair settability upon setting the hair with a hair cosmetic containing the organopolysiloxane graft polymer of the present invention and a high hair set retentivity under high-humidity conditions, and is also preferably not less than 1/30,000 mol/g, more preferably not less than 1/20,000 mol/g, still more preferably not less than 1/10,000, and even still more preferably not less than 1/4,000, from the viewpoint of a good water dispersibility of the graft polymer of the present invention.

<Reactive Functional Group-Containing Organopolysiloxane>

The radical-reactive organopolysiloxane may also be produced by reacting a reactive functional group-containing organopolysiloxane represented by the following general formula (6) or (7) with a radical reactivity-imparting agent.

The reactive functional group-containing organopolysiloxane represented by the following general formula (6) or (7) is readily commercially available as products having various structures.

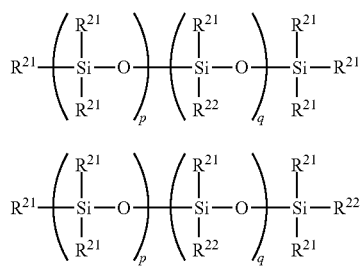

wherein $R^{21}$ groups are each independently an alkyl group having not less than 1 and not more than 22 carbon atoms or an aryl group having not less than 6 and not more than 14 carbon atoms; and $R^{22}$ is an alkyl group containing a reactive functional group (hereinafter also referred to as a "reactive group-containing alkyl group"). The suffixes p and q in the above general formulae (6) and (7) have the same meanings as p and q in the above general formulae (4) and (5), and the preferred forms of p and q in the above general formulae (6) and (7) are the same as the preferred forms of p and q in the above general formulae (4) and (5).

The preferred form of $R^{21}$ in the above general formulae (6) and (7) is the same as the preferred form of $R^{11}$ in the above general formulae (4) and (5).

The reactive functional group as used in the present invention means a hydroxyl group, an amino group, a carboxy group or an epoxy group.

The reactive functional group-containing organopolysiloxane contains at least one substituent group selected from the group consisting of a hydroxyl group, an amino group, a carboxy group and an epoxy group.

Of these reactive functional groups, from the viewpoint of a good availability, preferred are a hydroxyl group, an amino group and an epoxy group, and from the viewpoints of a high reactivity and a good handling property, more preferred is an amino group.

In the above general formulae (6) and (7), the number of carbon atoms of the reactive group-containing alkyl group represented by $R^{22}$ is preferably not less than 2, and more preferably not less than 3, form the viewpoint of a good availability of the reactive functional group-containing organopolysiloxane, and is also preferably not more than 15, more preferably not more than 10, and still more preferably not more than 5, from the viewpoint of a good water dispersibility of the graft polymer of the present invention.

Specific examples of the reactive group-containing alkyl group used in the present invention include those groups represented by the following formulae (xxi) to (xxviii). Of these reactive group-containing alkyl groups, from the viewpoint of a good availability, preferred is at least one reactive group-containing alkyl group selected from the group consisting of those groups represented by the following formulae (xxi) to (xxiv), and from the viewpoint of a high reactivity, more preferred is the reactive group-containing alkyl group represented by the following formula (xxiv).

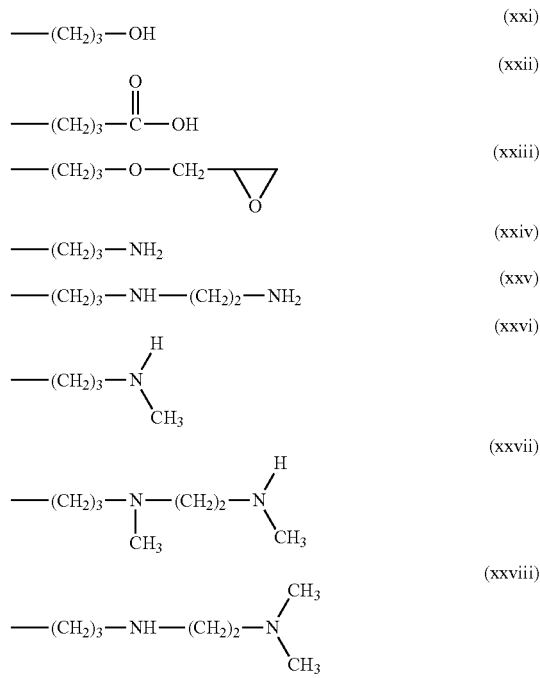

The number-average molecular weight (MNxm) of the reactive functional group-containing organopolysiloxane is preferably not less than 8,000, more preferably not less than 10,000, still more preferably not less than 11,000, and even still more preferably not less than 12,000, from the viewpoints of a high hair settability upon setting the hair using a hair cosmetic containing the organopolysiloxane graft polymer of the present invention, a high hair set retentivity under high-humidity conditions and a good touch feeling of hair after setting, and is also preferably not more than 200,000, more preferably not more than 100,000, still more preferably not more than 50,000, and even still more preferably not more than 30,000, from the viewpoints of a good water dispersibility of the graft polymer of the present invention and a good touch feeling of hair after setting.

Meanwhile, MNxm used in the present invention is the value in terms of polystyrene as measured by GPC under the measuring conditions described in Examples below.

The number of moles of the reactive functional group being present per a unit mass of the reactive functional group-containing organopolysiloxane is preferably not more than 1/500 mol/g, more preferably not more than 1/700 mol/g, still more preferably not more than 1/1,000 mol/g, and even still more preferably not more than 1/1,500 mol/g, from the viewpoints of a high hair settability upon setting the hair with a hair cosmetic containing the organopolysiloxane graft polymer of the present invention and a high hair set retentivity under high-humidity conditions, and is also preferably not less than 1/30,000 mol/g, more preferably not less than 1/20,000 mol/g, still more preferably not less than 1/10,000, and even still more preferably not less than 1/4,000, from the viewpoint of a good water dispersibility of the graft polymer of the present invention.

(Radical Reactivity-Imparting Agent)

The radical reactivity-imparting agent as used in the present invention means an agent capable of reacting with the reactive functional group of the reactive functional group-containing organopolysiloxane to add a radical-reactive functional group to the reactive functional group-containing organopolysiloxane.

As the radical reactivity-imparting agent, there may be used those compounds containing a radical-reactive functional group and at least one functional group capable of reacting with the reactive functional group of the above reactive functional group-containing organopolysiloxane which is selected from the group consisting of a carboxy group, an ester group, an epoxy group, a hydroxyl group and lactones, in a molecule thereof. In the case where the reactive functional group of the above reactive functional group-containing organopolysiloxane is a hydroxyl group, an amino group or an epoxy group, unsubstituted or substituted thiolactones may be used as the radical reactivity-imparting agent.

The radical-reactive functional group of the radical reactivity-imparting agent and the preferred form thereof are the same as the radical-reactive functional group of the radical-reactive organopolysiloxane and the preferred form thereof. Of these radical reactivity-imparting agents, from the viewpoint of a high reactivity upon polymerization, preferred are those radical reactivity-imparting agents containing a sulfanyl group (mercapto group) as the radical-reactive functional group, for example, compounds containing a sulfanyl group and a carboxy group in a molecule thereof such as 3-mercapto propionic acid, and lactones containing a sulfanyl group such as α-butyrolactone thiol. Also, as the unsubstituted or substituted thiolactones, there may be mentioned α-thiobutyrolactone, N-acetyl-DL-homocysteine thiolactone, DL-homocysteine thiolactone hydrochloride, or the like. Of these radical reactivity-imparting agents, from the viewpoints of a high reactivity with the reactive organopolysiloxane and a high reactivity upon the polymerization, more preferred is N-acetyl-DL-homocysteine thiolactone.

The amount of the radical reactivity-imparting agent used is preferably not less than 0.8 equivalent, and more preferably not less than 0.9 equivalent, on the basis of a total mass of the reactive functional group of the reactive functional group-containing organopolysiloxane, from the viewpoint of a high reactivity, and is also preferably not more than 1.2 equivalent, and more preferably not more than 1.1 equivalent, on the basis of a total mass of the reactive functional group of the reactive functional group-containing organopolysiloxane, from the viewpoint of reducing an amount of the radical reactivity-imparting agent remaining unreacted after the reaction.

(Production of Radical-Reactive Organopolysiloxane)

The reaction between the radical reactivity-imparting agent and the reactive functional group-containing organopolysiloxane may be carried out in the presence of a solvent.

Examples of the solvent include water; alcohols such as methanol, ethanol and isopropanol; ketones such as acetone and methyl ethyl ketone; esters such as ethyl acetate and butyl acetate; hydrocarbons such as hexane and cyclohexane; ethers such as diethyl ether and tetrahydrofuran; aromatic compounds such as benzene and toluene; and halogenated hydrocarbons such as dichloromethane and chloroform.

From the viewpoint of reducing an environmental burden, it is preferred that no solvent is used in the above reaction.

The reaction temperature is preferably not lower than 70° C., and more preferably not lower than 90° C., from the viewpoint of a high reactivity, and is also preferably not higher than 200° C., more preferably not higher than 150° C., and still more preferably not higher than 120° C., from the viewpoint of a good chemical stability of the resulting radical-reactive polysiloxane.

The reaction time is preferably not less than 1 h, and more preferably not less than 2 h, from the viewpoint of allowing the reaction to proceed sufficiently, and is also preferably not more than 10 h, and more preferably not more than 5 h, from the viewpoint of a high productivity.

From the viewpoint of a high reactivity of the resulting radical-reactive organopolysiloxane, the reaction between the reactive functional group-containing organopolysiloxane and the radical reactivity-imparting agent is preferably carried out until a conversion rate of at least one of the reactive functional group of the reactive functional group-containing organopolysiloxane and the radical reactivity-imparting agent reaches not less than 80%, and more preferably not less than 90%.

The method of measuring the respective conversion rates may vary depending upon the reactive functional group of the reactive functional group-containing organopolysiloxane and the radical reactivity-imparting agent used in the reaction, and any of the conversion rates may be measured by known methods. For example, in the case where the reactive functional group of the reactive functional group-containing organopolysiloxane is an amino group, and the radical reactivity-imparting agent is a thiolactone, the conversion rate of the amino group may be determined by "Testing Method for Total Base Number of Petroleum Products (perchloric acid method)" (JIS K 2501), and the conversion rate of the thiolactone may be determined by a gas chromatographic method.

(Production of Organopolysiloxane Graft Polymer)

The method of subjecting the unsaturated monomers to polymerization in the presence of the radical-reactive organopolysiloxane is not particularly limited, and there may be adopted a bulk polymerization method, a solution polymerization method and a suspension polymerization method, etc. Of these polymerization methods, preferred is a solution polymerization method.

The amount of the radical-reactive organopolysiloxane used as the raw material is preferably not less than 35% by mass, more preferably not less than 38% by mass, still more preferably not less than 40% by mass, and even still more preferably not less than 45% by mass, on the basis of a total mass of the radical-reactive organopolysiloxane and the unsaturated monomers as the raw materials, from the viewpoint of a good touch feeling of hair after setting the hair using the hair cosmetic of the present invention. Also, from the viewpoints of a good water dispersibility of the graft polymer of the present invention, a high hair settability after setting the hair using the hair cosmetic of the present invention, and a high hair set retentivity under high-humidity conditions, the amount of the radical-reactive organopolysiloxane used is preferably not more than 59% by mass, more preferably not more than 55% by mass, and still more preferably not more than 50% by mass, on the basis of a total mass of the radical-reactive organopolysiloxane and the unsaturated monomers as the raw materials.

The amount of the unsaturated monomers used as the raw material is preferably not less than 41% by mass, more preferably not less than 45% by mass, and still more preferably not less than 50% by mass, on the basis of a total mass of the radical-reactive organopolysiloxane and the unsaturated monomers as the raw materials, from the viewpoint of a good water dispersibility of the graft polymer of the present invention, a high hair settability after setting the hair using the hair cosmetic of the present invention, and a high hair set retentivity under high-humidity conditions. Also, from the viewpoint of a good touch feeling of hair after setting the hair using a hair cosmetic containing the organopolysiloxane graft polymer of the present invention, the amount of the unsaturated monomers used is preferably not more than 65% by mass, more preferably not more than 62% by mass, still more preferably not more than 60% by mass, and even still more preferably not more than 55% by mass, on the basis of a total mass of the radical-reactive organopolysiloxane and the unsaturated monomers as the raw materials.

The unsaturated monomers as the raw materials contain the unsaturated monomer containing a carboxylic acid or a carboxylic acid salt. The amount of the unsaturated monomer containing a carboxylic acid or a carboxylic acid salt used is preferably not less than 4.0% by mass, more preferably not less than 4.5% by mass, and still more preferably not less than 8% by mass, on the basis of a total mass of the radical-reactive organopolysiloxane and the unsaturated monomers as the raw materials, from the viewpoint of a good water dispersibility of the graft polymer of the present invention and a good touch feeling of hair after setting. Also, from the viewpoints of a high hair settability after setting the hair using the hair cosmetic of the present invention, and a high hair set retentivity under high-humidity conditions, the amount of the unsaturated monomer containing a carboxylic acid or a carboxylic acid salt used is preferably not more than 17% by mass, more preferably not more than 14% by mass, still more preferably not more than 11% by mass, and even still more preferably not more than 9% by mass, on the basis of a total mass of the radical-reactive organopolysiloxane and the unsaturated monomers as the raw materials.

The unsaturated monomers as the raw materials contain the copolymerizable monomer in addition to the unsaturated monomer containing a carboxylic acid or a carboxylic acid salt. Specific examples and preferred ranges of the copolymerizable monomer contained in the unsaturated monomers as the raw materials are the same as the specific examples and preferred ranges of the copolymerizable monomer as described in the above item <Unsaturated Monomer-Derived Copolymer Segment>. The copolymerizable monomer may be present in a single kind thereof or in the form of a mixture of plural kinds thereof.

The amount of the copolymerizable monomer used is preferably not less than 24% by mass, and more preferably not less than 28% by mass, on the basis of a total mass of the radical-reactive organopolysiloxane and the unsaturated monomers as the raw materials, from the viewpoints of a high hair settability after setting a style of the hair using the hair cosmetic of the present invention and a high hair set retentivity under high-humidity conditions. Also, from the viewpoints of a good touch feeling of hair after setting a style of the hair using the hair cosmetic of the present invention and a good water dispersibility of the graft polymer of the present invention, the amount of the copolymerizable monomer used is preferably not more than 61% by mass, and more preferably not more than 55% by mass, on the basis of a total mass of the radical-reactive organopolysiloxane and the unsaturated monomers as the raw materials.

In the case where the unsaturated monomers as the raw materials contain the unsaturated monomer having Tg for unsaturated monomer of not lower than 150° C. (except for the unsaturated monomer containing a carboxylic acid or a carboxylic acid salt), the amount of the unsaturated monomer having Tg for unsaturated monomer of not lower than 150° C. used is not more than 14% by mass, preferably not more than 12% by mass, more preferably not more than 10% by mass, and still more preferably not more than 5% by mass, on the basis of a total mass of the radical-reactive organopolysiloxane and the unsaturated monomers as the raw materials, from the viewpoints of facilitated shaping of hair at a hair temperature of not lower than 50° C. The lower limit of the amount of the unsaturated monomer having Tg for unsaturated monomer of not lower than 150° C. used is 0% by mass. Specific examples of the unsaturated monomer having Tg for unsaturated monomer of not lower than 150° C. (except for the unsaturated monomer containing a carboxylic acid or a carboxylic acid salt) are the same as specific examples of the unsaturated monomer having Tg for unsaturated monomer of not lower than 150° C. as described in the above item <Unsaturated Monomer-Derived Copolymer Segment>.

From the viewpoint of a good touch feeling of hair after setting the hair with the hair cosmetic of the present invention, the graft polymer of the present invention is preferably produced by reacting not less than 45% by mass and not more than 59% by mass of the radical-reactive organopolysiloxane, not less than 4% by mass and not more than 9% by mass of the unsaturated monomer containing a carboxylic acid or a carboxylic acid salt, and not less than 32% by mass and not more than 51% by mass of the copolymerizable monomer, on the basis of a total mass of the radical-reactive organopolysiloxane and the unsaturated monomers as the raw materials, and more preferably produced by reacting not less than 50% by mass and not more than 59% by mass of the radical-reactive organopolysiloxane, not less than 5% by mass and not more than 7% by mass of the unsaturated monomer containing a carboxylic acid or a carboxylic acid salt, and not less than 34% by mass and not more than 45% by mass of the copolymerizable monomer, on the basis of a total mass of the radical-reactive organopolysiloxane and the unsaturated monomers as the raw materials.

Also, from the viewpoint of a good water dispersibility of the graft polymer of the present invention, the graft polymer of the present invention is preferably produced by reacting not less than 45% by mass and not more than 59% by mass of the radical-reactive organopolysiloxane, not less than 8% by mass and not more than 17% by mass of the unsaturated monomer containing a carboxylic acid or a carboxylic acid salt, and not less than 24% by mass and not more than 47% by mass of the copolymerizable monomer, on the basis of a total mass of the radical-reactive organopolysiloxane and the unsaturated monomers as the raw materials, and more preferably produced by reacting not less than 50% by mass and not more than 59% by mass of the radical-reactive organopolysiloxane, not less than 10% by mass and not more than 15% by mass of the unsaturated monomer containing a carboxylic acid or a carboxylic acid salt, and not less than 26% by mass and not more than 40% by mass of the copolymerizable monomer, on the basis of a total mass of the radical-reactive organopolysiloxane and the unsaturated monomers as the raw materials.

In the case where the unsaturated monomers are polymerized by a solution polymerization method, the solvent used therein is not particularly limited as long as any of the radical-reactive organopolysiloxane and the unsaturated monomers as the raw materials as well as the obtained graft polymer of the present invention can be dissolved or homogeneously dispersed therein.

Specific examples the solvent include water; alcohols such as methanol, ethanol and isopropanol; ketones such as acetone and methyl ethyl ketone; esters such as ethyl acetate and butyl acetate; hydrocarbons such as hexane and cyclohexane; ethers such as diethyl ether and tetrahydrofuran; aromatic compounds such as benzene and toluene; and halogenated hydrocarbons such as dichloromethane and chloroform. These solvent may be used alone or in combination of any two or more thereof.

Of these solvents, from the viewpoint of obtaining the graft polymer of the present invention which has a more uniform side chain molecular weight distribution, it is preferred to use at least one solvent selected from the group consisting of water; alcohols having not less than 1 and not more than 8 carbon atoms such as ethanol and isopropanol; esters having not less than 2 and not more than 8 carbon atoms such as ethyl acetate and butyl acetate; and ethers having not less than 2 and not more than 8 carbon atoms such as diethyl ether and tetrahydrofuran. Further, from the viewpoint of bringing the solvent used upon production of the graft polymer of the present invention into cosmetic products and the like when using the graft polymer of the present invention in the applications of a hair cosmetic, etc., it is more preferred to use at least one solvent selected from the group consisting of water, and alcohols having not less than 1 and not more than 3 carbon atoms such as ethanol.

The amount of the solvent used is not particularly limited as long as any of the radical-reactive organopolysiloxane and the unsaturated monomers as well as the obtained organopolysiloxane graft polymer of the present invention can be dissolved or homogeneously dispersed therein. From the viewpoints of a facilitated operation upon production of the graft polymer and a high productivity thereof, the amount of the solvent used is preferably not less than 20% by mass, more preferably not less than 40% by mass, still more preferably not less than 60% by mass, and even still more preferably not less than 100% by mass, on the basis of a total mass of the radical-reactive organopolysiloxane and the unsaturated monomers charged upon production of the graft polymer. Also, from the viewpoint of a high reactivity, the amount of the solvent used is preferably not more than 1,000% by mass, more preferably not more than 900% by mass, still more preferably not more than 400% by mass, and even still more preferably not more than 300% by mass, on the basis of a total mass of the radical-reactive organopolysiloxane and the unsaturated monomers charged upon production of the graft polymer.

Examples of the polymerization initiator include azo-based initiators such as 2,2'-azobisisobutyronitrile and 2,2'-azobis(2,4-dimethyl valeronitrile); peroxide-based initiators such as lauroyl peroxide and benzoyl peroxide; and persulfate-based initiators such as ammonium persulfate. Also, the polymerization may be initiated by generating a radical by irradiation of light, etc. Of these polymerization initiators, from the viewpoint of a high reactivity, preferred is 2,2'-azobis(2,4-dimethyl valeronitrile). The amount of the polymerization initiator used is not particularly limited. The amount of the polymerization initiator used is preferably not more than 10% by mass, more preferably not more than 5% by mass, still more preferably not more than 2% by mass, and even still more preferably not more than 1% by mass, on the basis of a total mass of the unsaturated monomers charged, from the viewpoint of obtaining the organopolysiloxane graft polymer having a desired molecular weight, and is also preferably not less than 0.001% by mass, more preferably not less than 0.01% by mass, still more preferably not less than 0.1% by mass, and even still more preferably not less than 0.5% by mass, on the basis of a total mass of the unsaturated monomers charged, from the viewpoint of a high reactivity.

The temperature used upon the polymerization reaction may be appropriately selected according to the kinds of polymerization initiator and solvent used, etc., and is preferably not lower than 50° C., and more preferably not lower than 60° C., from the viewpoint of a high polymerization reaction rate. The polymerization reaction is preferably carried out under a normal pressure in order to reduce a burden on facilities used for the polymerization reaction. From the viewpoint of carrying out the reaction at a temperature not higher than a boiling point of the solvent, the temperature used upon the polymerization reaction is preferably not higher than 100° C., and more preferably not higher than 90° C.

The polymerization reaction is preferably carried out until the conversion rate of the unsaturated monomers reaches not less than 80%, and more preferably not less than 90%.

The conversion rate of the unsaturated monomers may be determined by nuclear magnetic resonance ($^1$H-NMR) analysis. The detailed procedures of $^1$H-NMR are specified in Examples below.

The polymerization reaction time is usually not less than 0.1 h and not more than 60 h, and is preferably not less than 0.5 h, more preferably not less than 1 h, still more preferably not less than 2 h, and even still more preferably not less than 4 h, from the viewpoint of a good operability, and is also preferably not more than 30 h, more preferably not more than 20 h, and still more preferably not more than 10 h, from the viewpoint of a high productivity. During the polymerization reaction, in the case where the raw materials are added dropwise, the polymerization reaction time includes the time required for the dropwise addition of the raw materials. The polymerization reaction time can be suitably controlled by varying the polymerization reaction temperature.

The radical-reactive organopolysiloxane and the unsaturated monomers as the raw materials, the solvent, the polymerization initiator, etc., may be added at one time to conduct the polymerization reaction. Alternatively, in order to control the composition of the resulting product, the polymerization reaction may be carried out by feeding these components in a split addition manner or in a dropwise addition manner. For example, there may be used (1) a method in which the radical-reactive organopolysiloxane, the unsaturated monomers and the solvent are mixed and heated, and then a solution in which the polymerization initiator is dissolved is added at one time or dropwise to the resulting mixture; (2) a method in which the solvent is heated, and then the radical-reactive organopolysiloxane, the unsaturated monomers and the initiator are each independently added to the heated solvent, or a solution prepared by mixing and dissolving these components in a solvent is added dropwise to the heated solvent; (3) a method in which the radical-reactive organopolysiloxane, a part of the unsaturated monomers and the solvent are mixed and heated, and then a solution in which the initiator and a remaining part of the unsaturated monomers are dissolved is added at one time or dropwise to the resulting mixture; or the like.

In addition, after completion of the polymerization reaction, the resulting product may be subjected to purification treatments, reduction of the unreacted unsaturated monomers therein or the like by known methods, if required. For example, the amounts of the unreacted unsaturated monomers and other impurities in the product may be reduced by heating after addition of the polymerization initiator thereto, membrane purification, steam distillation, adsorbent treatment, etc.

The organopolysiloxane graft polymer of the present invention may be produced by the aforementioned method. Alternatively, the organopolysiloxane graft polymer of the present invention may also be produced by the process for producing an organopolysiloxane graft polymer according to the present invention.

That is, the organopolysiloxane graft polymer of the present invention may be produced by the process for producing an organopolysiloxane graft polymer including an organopolysiloxane segment as a main chain thereof and an unsaturated monomer-derived copolymer segment containing a repeating unit derived from an unsaturated monomer containing a carboxylic acid or a carboxylic acid salt as a side chain thereof, said process including the step of subjecting unsaturated monomers containing the unsaturated monomer containing a carboxylic acid or a carboxylic acid salt to polymerization in the presence of a radical-reactive organopolysiloxane represented by the following general formula (4) or (5), in which a content of the organopolysiloxane segment in the organopolysiloxane graft polymer is not less than 35% by mass and not more than 59% by mass, a content of the repeating unit derived from the unsaturated monomer containing a carboxylic acid or a carboxylic acid salt in the organopolysiloxane graft polymer is not less than 4% by mass and not more than 17% by mass, and a content of a repeating unit derived from an unsaturated monomer whose homopolymer has a glass transition point of not lower than 150° C. (except for the unsaturated monomer containing a carboxylic acid or a carboxylic acid salt) in the organopolysiloxane graft polymer is not more than 14% by mass, and a number-average molecular weight of the organopolysiloxane segment is not less than 8,000 and not more than 200,000:

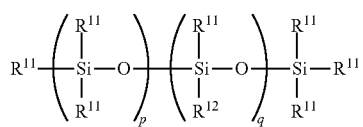

(4)

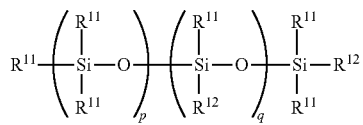

(5)

wherein $R^{11}$ groups are each independently an alkyl group having not less than 1 and not more than 22 carbon atoms or an aryl group having not less than 6 and not more than 14 carbon atoms; $R^{12}$ is an alkyl group containing a radical-reactive functional group; p is a number of not less than 2 and not more than 4,000; and q is a number of not less than 2 and not more than 250, in which repeating units in number of p and repeating units in number of q may be bonded to each other either in a block form or in a random form.

In the process for producing an organopolysiloxane graft polymer according to the present invention, the compounds, amounts, ratios and conditions used therein are the same as those described above in the respective preferred ranges. For example, the aforementioned radical-reactive organopolysiloxane is preferably produced by reacting a reactive functional group-containing organopolysiloxane represented by the following general formula (6) or (7) with a radical reactivity-imparting agent.

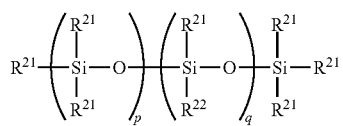

(6)

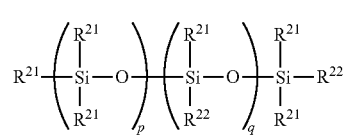

(7)

wherein $R^{21}$ groups are each independently an alkyl group having not less than 1 and not more than 22 carbon atoms or an aryl group having not less than 6 and not more than 14 carbon atoms; $R^{22}$ is an alkyl group containing a reactive functional group; p is a number of not less than 2 and not more than 4,000; and q is a number of not less than 2 and not more than 250, in which repeating units in the number of p and repeating units in the number of q may be bonded to each other either in a block form or in a random form.

[Hair Cosmetic]

(Graft Polymer of the Present Invention (Component (A)))

The hair cosmetic of the present invention contains the graft polymer of the present invention (hereinafter also referred to as a "component (A)"). By incorporating the graft polymer of the present invention into the hair cosmetic, it is possible to attain a soft touch, a hair settability that is free from change of a hair style even upon combing of hand or fingers through hair, and a more natural finish feeling.

The content of the component (A) in the hair cosmetic is preferably not less than 0.01% by mass, more preferably not less than 0.05% by mass, still more preferably not less than 0.1% by mass, and even still more preferably not less than 0.5% by mass, and is also preferably not more than 50% by mass, more preferably not more than 30% by mass, still more preferably not more than 20% by mass, and even still more preferably not more than 10% by mass, on the basis of a total mass of the hair cosmetic, from the viewpoints of a high hair settability of the hair cosmetic of the present invention, a high hair set retentivity under high-humidity conditions, a good touch feeling of hair and a good water dispersibility of the graft polymer of the present invention. By controlling the content of the component (A) in the hair cosmetic to the above-specified range, in particular, when using the below-mentioned organic solvent in combination with an organic acid or a salt thereof, it is possible to further enhance both a hair settability and a hair set retentivity under high-humidity conditions without inhibiting a hair modifying effect by the organic acid and organic solvent (such as enhancement in hair manageability).

(Solvent)

The hair cosmetic of the present invention may also contain, in addition to the above components, at least one solvent selected from the group consisting of water and straight-chain or branched-chain, saturated or unsaturated alcohols having not less than 1 and not more than 3 carbon atoms, from the viewpoints of a hair settability, a good feeling of use and facilitated operation upon preparation of the hair cosmetic. Of these solvents, preferred is at least one solvent selected from the group consisting of water, ethanol and isopropanol, and more preferred is at least one solvent selected from the group consisting of water and ethanol.

(Organic Solvent (Component (B)))

In addition, the hair cosmetic of the present invention may further contain an organic solvent selected from the group consisting of the following compounds (b1) to (b5) (hereinafter referred to as a "component (B)") as a preferred component form the viewpoints of attaining an effect of improving bounce and body of hair, an effect of improving softness and manageability of hair, promotion of modifying effects of hair (such as resilience improving effect and moisture resistance improving effect), etc., and enhancing a hair settability by compatibilizing the component (B) with the component (A).

(b1) Compounds represented by the general formula (8):

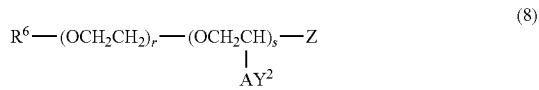

wherein $R^6$ is a hydrogen atom, an alkyl group having not less than 1 and not more than 6 carbon atoms or a group represented by $R^7$-Ph-$R^8$— wherein $R^7$ is a hydrogen atom, a methyl group or a methoxy group, $R^8$ is a bond or a divalent saturated or unsaturated hydrocarbon group having not less than 1 and not more than 3 carbon atoms, and Ph is a p-phenylene group; A is a bond or a divalent saturated hydrocarbon group having not less than 1 and not more than 4 carbon atoms; $Y^2$ and Z are each independently a hydrogen atom or a hydroxyl group; and r and s are each independently an integer of not less than 0 and not more than 5 with the proviso that when r and s are 0 (r=s=0), Z is a hydroxyl group, and $R^6$ is not any of a hydrogen atom, an alkyl group having not less than 1 and not more than 3 carbon atoms and a group represented by $R^7$-Ph-.

(b2) N-alkyl pyrrolidones or N-alkenyl pyrrolidones containing an alkyl group having not less than 1 and not more than 18 carbon atoms or an alkenyl group, which is bonded to a nitrogen atom therein.

(b3) Alkylene carbonates having not less than 2 and not more than 4 carbon atoms.

(b4) Polypropylene glycols having a number-average molecular weight of not less than 200 and not more than 1,000.

(b5) Lactones or cyclic ketones represented by the general formula (9), (10) or (11);

wherein $X^2$ is a methylene group or an oxygen atom; $R^9$ and $R^{10}$ are substituent groups that are different from each other; and a and b are each independently 0 or 1.

Examples of the compound (b1) among the organic solvents as the component (B) include straight-chain or branched-chain aliphatic alcohols having not less than 4 and not more than 6 carbon atoms, such as butanol and isobutanol, ethylene glycol, propylene glycol, dipropylene glycol, 1,3-butanediol, benzyl alcohol, cinnamyl alcohol, phenethyl alcohol, p-anisyl alcohol, p-methyl benzyl alcohol, phenoxyethanol, 2-benzyloxy ethanol, methyl carbitol, ethyl carbitol, propyl carbitol, butyl carbitol, triethylene glycol monoethyl ether and triethylene glycol monobutyl ether.

Examples of the compound (b2) include N-methyl pyrrolidone, N-octyl pyrrolidone and N-lauryl pyrrolidone.

Examples of the compound (b3) include ethylene carbonate and propylene carbonate.

Of the polypropylene glycols having a number-average molecular weight of not less than 200 and not more than 1,000 as the compound (b4), preferred are those having a number-average molecular weight of not less than 300 and not more than 500. Meanwhile, the number-average molecular weight means a number-average molecular weight as measured by GPC in terms of polystyrene.

In the compound (b5), $R^9$ and $R^{10}$ in the general formulae (9) to (11) are respectively preferably a straight-chain, branched-chain or cyclic alkyl group, a hydroxyl group, a sulfonic acid group, a phosphoric acid group, a carboxy group, a phenyl group, a sulfoalkyl group, an phosphoalkyl group or a carboxyalkyl group. Among these groups, straight-chain or branched-chain alkyl groups having not less than 1 and not more than 6 carbon atoms, for example, a methyl group, an ethyl group, a propyl group, an isopropyl group, a butyl group, etc., are more preferred. These substituent groups are preferably bonded to a α-position in the case where the compound (b5) is γ-lactone or a δ-position in the case where the compound (b5) is δ-lactone (i.e., methylene adjacent to a hetero oxygen atom). When it is intended to increase a water solubility of the respective compounds represented by the general formulae (9) to (11), $R^9$ or $R^{10}$ preferably contains an acid group such as a sulfonic acid group, a phosphoric acid group and a carboxy group, or an alkyl group substituted with the acid group.

Examples of the lactones among these compounds (b5) include γ-butyrolactone, γ-caprolactone, γ-valerolactone, δ-valerolactone, δ-caprolactone and δ-heptanolactone. From the viewpoint of a good stability of these lactones, preferred are γ-lactones, in particular, γ-butyrolactone and γ-caprolactone.

Examples of the cyclic ketones among the compounds (b5) include cyclopentanone, cyclohexanone, cycloheptanone and 4-methyl cycloheptanone.

In addition, the component (B) used in the present invention is preferably kept in a liquid state at 25° C. from the viewpoint of promotion of penetration of the component (B).

Further, from the viewpoint of promotion of penetration of the component (B), ClogP of the component (B) is preferably not less than −2, and more preferably not less than −1, and is also preferably not more than 3, and more preferably not more than 2. The parameter ClogP as used herein means a calculation value of an octanol/water partition coefficient (log P) defined by the following formula (II) as a scale representing partition of substances between an octanol phase and a water phase, examples of which are described in "Chemical Reviews", Vol. 71, No. 6 (1971).

$$\log P = \log([\text{substance}]_{Octanol}/[\text{substance}]_{Water}) \quad \text{(II)}$$

wherein $[\text{substance}]_{octanol}$ is a molar concentration of the substance in a 1-octanol phase; and $[\text{substance}]_{Water}$ is a molar concentration of the substance in a water phase.

Concrete values of ClogP of main compounds as the component (B) are as follows: dipropylene glycol (−0.67), 1,3-butanediol (−0.29), benzyl alcohol (1.1), 2-benzyloxy ethanol (1.2), 2-phenyl ethanol (1.2), 1-phenoxy-2-propanol (1.1), polypropylene glycol 400 (0.9), propylene carbonate (−0.41), and γ-butyrolactone (−0.64). Of these components (B), preferred are benzyl alcohol and 2-benzyloxy ethanol.

These components (B) may be used in combination of any two or more thereof. The total content of the compounds as the component (B) in the hair cosmetic is preferably not less than 0.1% by mass, more preferably not less than 0.5% by mass, and still more preferably not less than 1% by mass, and is also preferably not more than 40% by mass, more preferably not more than 10% by mass, and still more preferably not more than 5% by mass, from the viewpoints of a good effect of improving bounce and body of hair, a good effect of improving softness and manageability of hair, promotion of modifying effect of hair (such as resilience improving effect and moisture resistance improving effect), and a good effect of enhancing a hair settability by compatibilizing the component (B) with the component (A).

(Organic Carboxylic Acid and Salt Thereof (Component (C)))

Also, the hair cosmetic used in the present invention may contain, together with the component (B), an organic carboxylic acid or a salt thereof which may contain a hydroxyl group (hereinafter referred to as a "component (C)") from the viewpoints of attaining an inside modifying effect of hair (such as hollowness mending effect), an effect of improving bounce and body of hair, an effect of improving softness and manageability of hair, and enhancing a hair settability by compatibilizing the component (C) with the component (A). In this case, from the viewpoint of promotion of penetration of the component (C), preferred examples of the component (B) include dipropylene glycol, 1,3-butanediol, benzyl alcohol, phenoxyethanol, 2-benzyloxy ethanol, propylene carbonate and polypropylene glycol (having a number-average molecular weight of preferably not less than 300 and not more than 500, and more preferably 400).

The organic carboxylic acid as the component (C) is preferably an organic carboxylic acid having not less than 2 and not more than 8 carbon atoms, from the viewpoint of promotion of penetration of the component (C).

Specific examples of the organic carboxylic acid as the component (C) include monocarboxylic acids such as acetic acid and propionic acid; dicarboxylic acids such as malonic acid, succinic acid, glutaric acid, adipic acid, maleic acid, fumaric acid and phthalic acid; polycarboxylic acids such as polyglutamic acid; hydroxycarboxylic acids such as glycolic acid, lactic acid, hydroxyacrylic acid, glyceric acid, malic acid, tartaric acid and citric acid; and acidic amino acids such as glutamic acid and aspartic acid. Of these organic carboxylic acids, from the viewpoint of promotion of penetration of the component (C), preferred are hydroxycarboxylic acids having not less than 2 and not more than 6 carbon atoms, and more preferred are lactic acid and malic acid.

Examples of salts of these organic carboxylic acids include salts of these organic carboxylic acids with an alkali metal, an alkali earth metal, ammonia or an organic amine compound.

These compounds as the component (C) may be used in combination of any two or more thereof. The total content of the compounds as the component (C) in the hair cosmetic is preferably not less than 0.1% by mass, more preferably not less than 0.5% by mass, and still more preferably not less than 0.5% by mass, and is also preferably not more than 30% by mass, more preferably not more than 20% by mass, and still more preferably not more than 10% by mass, from the viewpoints of attaining an inside modifying effect of hair (such as hollowness mending effect), an effect of improving bounce and body of hair, an effect of improving softness and manageability of hair, and enhancing a hair settability by compatibilizing the component (C) with the component (A).

The mass ratio of the organic carboxylic acid or salt thereof as the component (C) to the organic solvent as the component (B) ((C):(B)) is preferably in the range of from 10:1 to 1:7, and more preferably from 4:1 to 1:3, in order to effectively exhibit an inside modifying effect of hair (such as hollowness mending effect), an effect of improving bounce and body of hair, and an effect of improving softness and manageability of hair.

(Set Polymer (Component (D)))

Further, the hair cosmetic of the present invention may contain, in addition to the component (A) as the set polymer, an additional set polymer (hereinafter referred to as a "component (D)"), if required.

Examples of the additional set polymer as the component (D) include the following polymers 1) to 8). These polymers may be used alone or in combination of any two or more thereof.

1) Vinyl Pyrrolidone-Based Polymer
Polyvinyl Pyrrolidone:
Examples of commercially available products of the polyvinyl pyrrolidone include "LUVISKOL K12" and "LUVISKOL K30" (both available from BASF), "PVP K15" and "PVP K30" (both available from Ashland Inc.), and the like.

Vinyl Pyrrolidone/Vinyl Acetate Copolymer:
Examples of commercially available products of the vinyl pyrrolidone/vinyl acetate copolymer include "LUVISKOL VA28" and "LUVISKOL VA73" (both available from BASF), "PVP/VA E-735" and "PVP/VA S-630" (both available from Ashland Inc.), and the like.

Vinyl Pyrrolidone/Vinyl Acetate/Vinyl Propionate Terpolymer:
Examples of commercially available products of the vinyl pyrrolidone/vinyl acetate/vinyl propionate terpolymer include "LUVISKOL VAP343" (available from BASF), and the like.

Vinyl Pyrrolidone/Alkylaminoacrylate Copolymer:
Examples of commercially available products of the vinyl pyrrolidone/alkylaminoacrylate copolymer include "LUVIFLEX" (available from BASF), "COPOLYMER 845", "COPOLYMER 937" and "COPOLYMER 958" (all available from Ashland Inc.), and the like.

Vinyl Pyrrolidone/Acrylate/(Meth)Acrylic Acid Copolymer:
Examples of commercially available products of the vinyl pyrrolidone/acrylate/(meth)acrylic acid copolymer include "LUVIFLEX VBM35" (available from BASF), and the like.

Vinyl Pyrrolidone/Alkylaminoacrylate/Vinyl Caprolactam Copolymer:
Examples of commercially available products of the vinyl pyrrolidone/alkylaminoacrylate/vinyl caprolactam copolymer include "COPOLYMER VC-713" (available from Ashland Inc.), and the like.

2) Acidic Vinyl Ether-Based Polymer
Methyl Vinyl Ether/Maleic Anhydride Alkyl Half Ester Copolymer:
Examples of commercially available products of the methyl vinyl ether/maleic anhydride alkyl half ester copolymer include "GANTREZ ES-225", "GANTREZ ES-425" and "GANTREZ SP-215" (all available from Ashland Inc.), and the like.

3) Acidic Polyvinyl Acetate-Based Polymer
Vinyl Acetate/Crotonic Acid Copolymer:
Examples of commercially available products of the vinyl acetate/crotonic acid copolymer include "RESIN 28-1310" (available from AKZO NOBEL), "LUVISET CA66" (available from BASF), and the like.

Vinyl Acetate/Crotonic Acid/Vinyl Neodecanoate Copolymer:

Examples of commercially available products of the vinyl acetate/crotonic acid/vinyl neodecanoate copolymer include "RESIN 28-2930" (available from AKZO NOBEL), and the like.

Vinyl Acetate/Crotonic Acid/Vinyl Propionate Copolymer:

Examples of commercially available products of the vinyl acetate/crotonic acid/vinyl propionate copolymer include "LUVISET CAP" (available from BASF), and the like.

4) Acidic Acrylic Polymer (Meth)Acrylic Acid/(Meth)Acrylic Acid Ester Copolymer:

Examples of commercially available products of the (meth)acrylic acid/(meth)acrylic acid ester copolymer include "PLUS SIZE L53P" (available from GOO Chemical Co., Ltd.), "DIAHOLD" (available from Mitsubishi Chemical Holdings Corporation), and the like.

Acrylic Acid/Acrylic Acid Alkyl Ester/Alkyl Acrylamide Copolymer:

Examples of commercially available products of the acrylic acid/acrylic acid alkyl ester/alkyl acrylamide copolymer include "ULTRAHOLD 8" (available from BASF), "UNFOAMER V-42" (available from AKZO NOBEL), and the like.

5) Amphoteric Acrylic Polymer (Meth)Acryl Ethyl Betaine/(Meth)Acrylic Acid Alkyl Ester Copolymer:

Examples of the (meth)acryl ethyl betaine/(meth)acrylic acid alkyl ester copolymer include a copolymer of N-methacryloyloxyethyl-N,N-dimethyl ammonium-α-N-methyl carboxybetaine and a (meth)acrylic acid alkyl ester, and the like, and examples of commercially available products of the (meth)acryl ethyl betaine/(meth)acrylic acid alkyl ester copolymer include "YUKAFOAMER M-75" and "YUKAFOAMER SM" (both available from Mitsubishi Chemical Holdings Corporation), and the like.

Acrylic Acid Alkyl Ester/Butylaminoethyl Methacrylate/Acrylic Acid Octyl Amide Copolymer:

Examples of the acrylic acid alkyl ester/butylaminoethyl methacrylate/acrylic acid octyl amide copolymer include an octyl acrylamide/acrylate/butylaminoethyl methacrylate copolymer and the like, and examples of commercially available products of the acrylic acid alkyl ester/butylaminoethyl methacrylate/acrylic acid octyl amide copolymer include "UNFOAMER 28-4910" (available from AKZO NOBEL), and the like.

6) Basic Acrylic Polymer

Acrylamide/Acrylic Ester-Based Copolymer:

Examples of the acrylamide/acrylic ester-based copolymer include those copolymers described in Examples of JP 2-180911A and JP 8-291206A, and the like.

7) Cellulose Derivative

Cationic Cellulose Derivative:

Examples of commercially available products of the cationic cellulose derivative include "CELLCOAT H-100" and "CELLCOAT L-200" (both available from AKZO NOBEL), and the like.

8) Chitin/Chitosan Derivative

Hydroxypropyl Chitosan:

Examples of commercially available products of the hydroxypropyl chitosan include "CHITOFILMER" (available from Ichimaru Falcos Co., Ltd.,) and the like.

Salt of carboxymethyl chitin, carboxymethyl chitosan or chitosan with a monovalent acid such as pyrrolidone carboxylic acid, lactic acid and glycolic acid or a divalent acid such as adipic acid and succinic acid:

Examples of commercially available products of the above salt include "CHITOMER PC" (pyrrolidone carboxylic acid salt) and "CHITOMER L" (lactic acid salt) (both available from The Dow Chemical Company), and the like.

Of these set polymers, preferred are, in particular, those set polymers selected from acrylic polymers and vinyl pyrrolidone-based polymers. The content of the set polymer in the hair cosmetic is preferably not less than 0.05% by mass, more preferably not less than 0.1% by mass, and still more preferably not less than 0.3% by mass, and is also preferably not more than 20% by mass, more preferably not more than 10% by mass, and still more preferably not more than 5% by mass, on the basis of a total mass of the hair cosmetic.

(Conditioning Component)

The hair cosmetic used in the present invention may also contain a conditioning component selected from oil agents and silicones (except for the component (A) of the present invention) for the purpose of further enhancing a conditioning effect of hair.

The oil agents are used for enhancing a feeling of manageability of hair after drying. Examples of the oil agents include hydrocarbons such as squalene, squalane, liquid isoparaffin, light liquid isoparaffin, heavy liquid isoparaffin, α-olefin oligomers, liquid paraffin and cycloparaffin; glycerides such as castor oil, cacao seed oil, mink oil, avocado oil and olive oil; waxes such as beeswaxes, spermaceti, lanolin, microcrystalline waxes, ceresin waxes and carnauba waxes; higher alcohols such as cetyl alcohol, oleyl alcohol, stearyl alcohol, isostearyl alcohol and 2-octyl dodecanol; esters such as octyl dodecyl myristate, hexyl laurate, cetyl lactate, propylene glycol monostearate, oleyl oleate, hexadecyl 2-ethyl hexanoate, isononyl isononanoate and tridecyl isononanoate; higher fatty acids such as capric acid, lauric acid, myristic acid, palmitic acid, stearic acid, behenic acid, oleic acid, coconut oil fatty acid, isostearic acid and isopalmitic acid; solid fats such as cholesterol, vaseline, cholesteryl isostearate and sphingolipid; as well as jojoba oil, isostearyl glyceryl ether and polyoxypropylene butyl ether. Of these oil agents, preferred are branched hydrocarbons such as squalene, squalane, liquid isoparaffin, light liquid isoparaffin, heavy liquid isoparaffin and α-olefin oligomers.

The content of the oil agents in the hair cosmetic is preferably not less than 0.05% by mass, more preferably not less than 0.1% by mass, and still more preferably not less than 0.5% by mass, and is also preferably not more than 20% by mass, more preferably not more than 10% by mass, and still more preferably not more than 5% by mass, from the viewpoints of a good hair manageability and a less sticky feeling.

Examples of the silicones (except for the component (A) of the present invention) include dimethyl polysiloxane, polyether-modified silicones, amino-modified silicones, carboxy-modified silicones, methyl phenyl polysiloxane, fatty acid-modified silicones, polyglycerin-modified silicones, aliphatic alcohol-modified silicones, epoxy-modified silicones, fluorine-modified silicones, cyclic silicones and alkyl-modified silicones. Of these silicones, preferred are dimethyl polysiloxane, polyether-modified silicones and amino-modified silicones.

The dimethyl polysiloxane is capable of imparting a good lubricating property to hair; the polyether-modified silicones are capable of imparting smoothness to hair; and the amino-modified silicones are capable of imparting a good moist feeling to hair. In the hair cosmetic of the present invention, various silicones may be used alone or in combination of any two or more thereof according to their performances as demanded.

The dimethyl polysiloxane used may have a viscosity ranging from about 5 mm²/s to about 10,000,000 mm²/s at which the dimethyl polysiloxane may be frequently supplied in the from of an emulsion, according to a touch feeling of hair as demanded. The viscosity of the dimethyl polysiloxane is preferably not less than 5,000 mm²/s, and more preferably not less than 50,000 mm²/s, and is also preferably not more than 10,000,000 mm²/s, and more preferably 10,000,000 mm²/s. Meanwhile, the above viscosity is a viscosity as measured at 25° C.

The polyether-modified silicones are not particularly limited as long as they may be silicones having a polyoxyalkylene group. Examples of the group constituting the polyoxyalkylene group include an oxyethylene group and an oxypropylene group. Specific examples of the polyether-modified silicones include "KF-6015", "KF-945 A", "KF-6005", "KF-6009", "KF-6013", "KF-6019", "KF-6029", "KF-6017", "KF-6043", "KF-353 A", "KF-354 A" and "KF-355 A" (all available from Shin-Etsu Chemical Co., Ltd.); and "FZ-2404", "SS-2805", "FZ-2411", "FZ-2412", "SH3771M", "SH3772M", "SH3773M", "SH3775M", "SH3749", "SS-280 X Series", "BY22-008M", "BYR11-030" and "BY25-337" (all available from Dow Corning Toray Co., Ltd.).

The amino-modified silicones are preferably those described under the name of "Amodimethicone" having an average molecular weight of not less than about 3,000 and not more than about 100,000 in CTFA Dictionary (US, Cosmetic Ingredient Dictionary), 3rd Edition. Examples of commercially available products of the amino-modified silicones include "SM 8704C" (available from Dow Corning Toray Co., Ltd.), "DC 929" (available from Dow Corning Corp.), "KT 1989" (available from Momentive Performance Materials Japan Inc.), and "8500 Conditioning Agent", "DOW CORNING TORAY SS-3588" and "DOW CORNING TORAY SILSTYLE 104" (all available from Dow Corning Toray Co., Ltd.).

The content of the silicones (except for the component (A) of the present invention) in the hair cosmetic of the present invention is preferably not less than 0.05% by mass, more preferably not less than 0.1% by mass, and still more preferably not less than 0.5% by mass, and is also preferably not more than 20% by mass, more preferably not more than 10% by mass, and still more preferably not more than 5% by mass, from the viewpoints of smooth combing of fingers through hair and a less sticky feeing.

(Surfactant)

The hair cosmetic of the present invention may also contain a surfactant from the viewpoints of improving a stability of the system including a solubilizability or a dispersibility of the solvent, etc., and enhancing a touch feeling of hair. As the surfactant, there may be used any of a cationic surfactant, a nonionic surfactant, an amphoteric surfactant and an anionic surfactant.

As the cationic surfactant, there may be mentioned an ammonium salt or a quaternary ammonium salt represented by the following general formula (12):

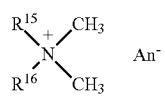

(12)

wherein $R^{15}$ and $R^{16}$ are each independently a hydrogen atom, an alkyl group having not less than 1 and not more than 28 carbon atoms or a benzyl group except for the case where $R^{15}$ and $R^{16}$ are constituted of a hydrogen atom, a benzyl group or a lower alkyl group having not less than 1 and not more than 3 carbon atoms, or a combination thereof, at the same time; An⁻ is a counter ion of the ammonium or quaternary ammonium.

In the general formula (12), one of $R^{15}$ and $R^{16}$ is preferably an alky group having not less than 16 and not more than 24 carbon atoms, more preferably an alkyl group having 22 carbon atoms, and still more preferably a straight-chain alkyl group having 22 carbon atoms, and the other of $R^{15}$ and $R^{16}$ is preferably a lower alky group having not less than 1 and not more than 3 carbon atoms, and more preferably a methyl group. Examples of An⁻ include an ethylsulfuric acid ion, a methylsulfuric acid ion, a chloride ion, an iodide ion, a sulfuric acid ion, a p-toluenesulfonic acid ion and a perchloric acid ion.

The cationic surfactant is preferably a mono-long chain alkyl quaternary ammonium salt. Specific examples of the cationic surfactant include cetyl trimethyl ammonium chloride, stearyl trimethyl ammonium chloride, behenyl trimethyl ammonium chloride and alkyl benzalkonium chlorides. Of these cationic surfactants, preferred are stearyl trimethyl ammonium chloride and behenyl trimethyl ammonium chloride.

Examples of the nonionic surfactant include polyoxyalkylene alkyl ethers, polyoxyalkylene alkenyl ethers, higher fatty acid sucrose esters, polyglycerin fatty acid esters, higher fatty acid mono- or diethanol amides, polyoxyethylene hardened castor oil, polyoxyethylene sorbitan fatty acid esters, polyoxyethylene sorbitol fatty acid esters, alkyl saccharide-based surfactants, alkyl amine oxides and alkyl amide amine oxides. Of these nonionic surfactants, preferred are polyoxyalkylene alkyl ethers and polyoxyethylene hardened castor oil, and more preferred are polyoxyethylene alkyl ethers and polyoxyethylene/polyoxypropylene alkyl ethers.

Examples of the amphoteric surfactant include imidazoline-based surfactants, carbobetaine-based surfactants, amide betaine-based surfactants, sulfobetaine-based surfactants, hydroxysulfobetaine-based surfactants and amide sulfobetaine-based surfactants. Of these amphoteric surfactants, preferred are betaine-based surfactants such as alkyl dimethyl aminoacetic acid betaines and fatty acid amide propyl betaines, and more preferred are fatty acid amide propyl betaines. The fatty acid amide propyl betaines are preferably those containing an acyl group having not less than 8 and not more than 18 carbon atoms, more preferably those containing an acyl group having not less than 10 and not more than 16 carbon atoms, and still more preferably lauric acid amide propyl betaine, palm kernel oil fatty acid amide propyl betaine and coconut oil fatty acid amide propyl betaine.

Examples of the anionic surfactant include alkyl benzenesulfonic acid salts, alkyl or alkenyl ether sulfuric acid salts, alkyl or alkenyl sulfuric acid salts, olefin sulfonic acid salts, alkane sulfonic acid salts, saturated or unsaturated fatty acid salts, alkyl or alkenyl ether carboxylic acid salts, α-sulfone fatty acid salts, N-acyl amino acid-type surfactants, phosphoric acid mono- or diester-type surfactants and sulfosuccinic acid esters. Examples of counter ions to an anionic residue of the above surfactants include alkali metal ions such as a sodium ion and a potassium ion; alkali earth metal ions such as a calcium ion and a magnesium ion; an ammonium ion; alkanol amines containing not less than 1 and not more than 3 alkanol groups each having 2 or 3 carbon atoms (for example, monoethanol amine, diethanol amine, triethanol amine, triisopropanol amine, etc.).

Of these surfactants, from the viewpoint of a good touch feeling of hair upon using the hair cosmetic of the present invention, preferred are the cationic surfactant and the nonionic surfactant. These surfactants may be used alone or in combination of any two or more kinds thereof.

The content of the surfactant in the hair cosmetic of the present invention is preferably not less than 0.01% by mass, and more preferably not less than 0.05% by mass, and is also preferably not more than 10% by mass, and more preferably not more than 5% by mass, from the viewpoints of a good touch feeling of hair upon using the hair cosmetic of the present invention and a good stability of the system including solubilization, emulsification, etc., of solvents or oil agents upon formulating the solvents or oil agents in the hair cosmetic.

(Polyhydric Alcohol)

Further, the hair cosmetic used in the present invention may also contain a polyhydric alcohol other than the component (B). The polyhydric alcohol contributes to solubilization and stable dispersion of the component (B), and also acts synergistically with the component (B) to promote improvement in hair luster or hair modifying effect. Examples of the polyhydric alcohol include glycerin, sorbitol, etc. Of these polyhydric alcohols, preferred is glycerin.

The polyhydric alcohols may be used alone or in combination of any two or more thereof.

The content of the polyhydric alcohol in the hair cosmetic of the present invention is preferably not less than 0.1% by mass, and more preferably not less than 0.5% by mass, and is also preferably not more than 10% by mass, and more preferably not more than 5% by mass.

(Other Components)

In addition to the aforementioned components, other components that can be used in ordinary hair cosmetics may also be appropriately formulated in the hair cosmetic of the present invention according to objects, applications, dosage forms, etc. Examples of the other components include antidandruff agents such as zinc pyrithione and octopirox; vitamin reagents; bactericides such as triclosan and triclocarban; anti-inflammatory agents such as dipotassium glycyrrhizate and tocopherol acetate; antiseptic agents such as methyl paraben and butyl paraben; chelating agents; humectants such as panthenol; colorants such as dyes and pigments; viscosity modifiers such as hydroxyethyl cellulose, methyl cellulose, polyethylene glycol and clay minerals; pH controllers such as organic acids, sodium hydroxide and potassium hydroxide; plant essences; pearling agents; perfumes; coloring matters; ultraviolet absorbers; antioxidants; and other components as described in "Encyclopedia of Shampoo Ingredients" (MICELLE PRESS).

(Configuration of Hair Cosmetic)

The hair cosmetic used in the present invention may be prepared with various configurations or dosage forms by ordinary methods. Examples of the configurations or dosage forms of the hair cosmetic include not only a liquid composition such as a mist, a lotion and a tonic, but also a semi-solid composition such as a gel, a paste, a cream and a wax.

The hair cosmetic of the present invention may also contain a propellant, and may be used in the form of an aerosol type hair cosmetic. The propellant contained in the hair cosmetic is not particularly limited as long as it can be usually used in aerosol type cosmetics. Examples of the propellant usable in the present invention include lower saturated hydrocarbons such as propane, butane and mixtures thereof (including liquefied petroleum gas); ethers such as dimethyl ether; and a nitrogen gas, a carbon dioxide gas and a nitrous oxide gas. These propellants may be used alone or in combination of any two or more thereof.

The content of the propellant in the hair cosmetic of the present invention is preferably not less than 0.01% by mass, and more preferably not less than 10% by mass, and is also preferably not more than 100% by mass, and more preferably not more than 40% by mass, on the basis of a total mass of the hair cosmetic (except for the propellant).

Furthermore, the hair cosmetic of the present invention may also be used in the form of a non-aerosol type hair cosmetic by filling a composition containing the organopolysiloxane as the component (A) into a foam injection container. The foam injection container is not particularly limited as long as it is capable of mixing the composition with air and injecting the resulting mixture in a foamed state therefrom. Examples of the foam injection container include a squeeze foamer that is used by pressing a barrel of a soft container with hand or fingers, a pump foamer that is used by pressing a head of a cap equipped with a pump mechanism with hand or fingers, a trigger type foamer, etc.

As the squeeze foamer, there may be mentioned those squeeze foamers described in JUM 62-042785B, JUM 62-042786B and JUM 62-042787B, and similar products thereto. As the pump foamer, there may be mentioned those pump foamers described in JP 7-315463A, JP 08-230961A, etc., and similar products thereto. These containers may be frequently provided at an injection portion thereof with a screen for the purpose of further improving a quality of injected foam. Of these containers, preferred are those containers equipped with one or more screens having an opening size of not less than 100 mesh and not more than 300 mesh.

The hair cosmetic is preferably used in the form of a hair styling agent, a hair conditioning agent, etc. Examples of the preferred configurations or dosage forms of the hair cosmetic include a pump spray, an aerosol spray, a pump foam, an aerosol foam, a gel, a lotion, a mist and a cream. Of these configurations or dosage forms, preferred are a pump spray, a pump foam and an aerosol foam.

With respect to the aforementioned embodiments of the present invention, there are further described the following aspects concerning the organopolysiloxane graft polymer as well as the hair cosmetic containing the organopolysiloxane graft polymer, etc.

<1> An organopolysiloxane graft polymer including an organopolysiloxane segment as a main chain thereof and an unsaturated monomer-derived copolymer segment containing a repeating unit derived from an unsaturated monomer containing a carboxylic acid or a carboxylic acid salt as a side chain thereof, in which a content of the organopolysiloxane segment in the organopolysiloxane graft polymer is not less than 35% by mass and not more than 59% by mass, a content of the repeating unit derived from the unsaturated monomer containing a carboxylic acid or a carboxylic acid salt in the organopolysiloxane graft polymer is not less than 4% by mass and not more than 17% by mass, and a content of a repeating unit derived from an unsaturated monomer whose homopolymer has a glass transition point of not lower than 150° C. (except for the unsaturated monomer containing a carboxylic acid or a carboxylic acid salt) in the organopolysiloxane graft polymer is not more than 14% by mass, and a number-average molecular weight of the organopolysiloxane segment is not less than 8,000 and not more than 200,000.

<2> The organopolysiloxane graft polymer according to the above aspect <1>, wherein a number-average molecular weight of the organopolysiloxane segment is preferably not less than 10,000, more preferably not less than 11,000, and still more preferably not less than 12,000, and is also preferably not more than 100,000, more preferably not more than 50,000, and still more preferably not more than 30,000.

<3> The organopolysiloxane graft polymer according to the above aspect <1> or <2>, wherein a number-average molecular weight (MNg) of the organopolysiloxane segment being present between the adjacent unsaturated monomer-derived copolymer segments among the organopolysiloxane segments is preferably not less than 500, more preferably not less than 700, and still more preferably not less than 1,000, and is also preferably not more than 30,000, more preferably not more than 20,000, and still more preferably not more than 4,000.

<4> The organopolysiloxane graft polymer according to any one of the above aspects <1> to <3>, wherein the organopolysiloxane segment is a modified organopolysiloxane segment represented by the following general formula (1) or (2):

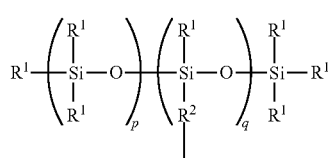

(1)

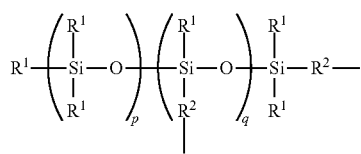

(2)

wherein $R^1$ groups are each independently an alkyl group having not less than 1 and not more than 22 carbon atoms or an aryl group having not less than 6 and not more than 14 carbon atoms; $R^2$ is an alkylene group that may contain a hetero atom; p is a number of not less than 2 and not more than 4,000; and q is a number of not less than 2 and not more than 250, in which repeating units in the number of p and repeating units in the number of q may be bonded to each other either in a block form or in a random form.

<5> The organopolysiloxane graft polymer according to the above aspect <4>, wherein in the above general formulae (1) and (2), $R^1$ is a straight-chain or branched-chain alkyl group having not less than 1 and not more than 6 carbon atoms, preferably a straight-chain or branched-chain alkyl group having not less than 1 and not more than 3 carbon atoms, and more preferably a methyl group.

<6> The organopolysiloxane graft polymer according to the above aspect <4> or <5>, wherein in the above general formulae (1) and (2), p is preferably a number of not less than 50, more preferably not less than 60, still more preferably not less than 80, and even still more preferably not less than 100, and is also preferably a number of not more than 1,500, more preferably not more than 1,300, still more preferably not more than 900, even still more preferably not more than 500, and further even still more preferably not more than 200.

<7> The organopolysiloxane graft polymer according to any one of the above aspects <4> to <6>, wherein in the above general formulae (1) and (2), q is preferably a number of not less than 3, and is also preferably a number of not more than 150, more preferably not more than 110, still more preferably not more than 70, even still more preferably not more than 20, and further even still more preferably not more than 10.

<8> The organopolysiloxane graft polymer according to any one of the above aspects <4> to <7>, wherein in the above general formulae (1) and (2), the number of carbon atoms of the alkylene group ($R^2$) which may contain a hetero atom is preferably not less than 2, and more preferably not less than 3, and is also preferably not more than 20, more preferably not more than 10, and still more preferably not more than 8.

<9> The organopolysiloxane graft polymer according to any one of the above aspects <4> to <8>, wherein in the above general formulae (1) and (2), the alkylene group ($R^2$) which may contain a hetero atom is bonded to the unsaturated monomer-derived polymer segment through the hetero atom, preferably through a nitrogen atom, an oxygen atom or a sulfur atom, and more preferably through a sulfur atom.

<10> The organopolysiloxane graft polymer according to any one of the above aspects <4> to <9>, wherein in the above general formulae (1) and (2), the alkylene group ($R^2$) which may contain a hetero atom is a group selected from the group consisting of those groups represented by the following formulae (i) to (xii), and preferably a group selected from the group consisting of those groups represented by the following formulae (xi) and (xii):

(i)

(ii)

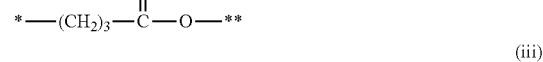

(iii)

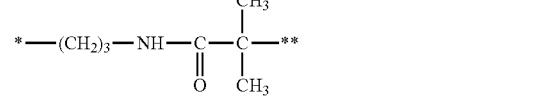

(iv)

(v)

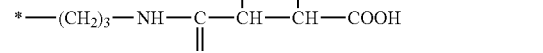

(vi)

(vii)

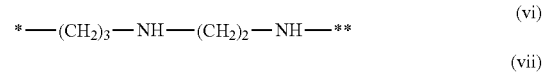

(viii)

-continued

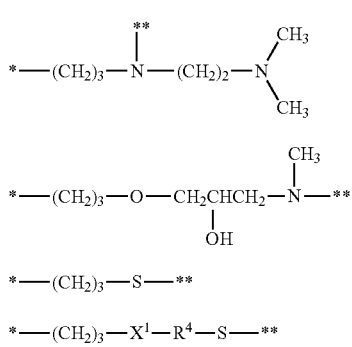

wherein "*" represents a moiety bonded to the silicon atom in the general formula (1) or (2), and "**" represents a moiety bonded to the unsaturated monomer-derived copolymer segment;

in the formula (xii), $X^1$ is an atom or group selected from the group consisting of —O—, —OCO—, —COO—, —CONH— and —NHCO—; and in the formula (xii), $R^4$ is an alkylene group that may be substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having 2 to 4 carbon atoms, a carboxy group and a ($C_1$-$C_3$) alkyl ester group.

<11> The organopolysiloxane graft polymer according to the above aspect <10>, wherein in the formula (xii), $X^1$ is —CONH— or —NHCO—, and preferably —NHCO—.

<12> The organopolysiloxane graft polymer according to the above aspect <10> or <11>, wherein in the formula (xii), $R^4$ is an alkylene group that may be substituted with an acetamide group, a ($C_1$-$C_3$) alkyl amino group or an amino group.

<13> The organopolysiloxane graft polymer according to any one of the above aspects <10> to <12>, wherein in the formula (xii), $R^2$ is a group selected from the group consisting of those groups represented by the following formulae (xiii) to (xiv).

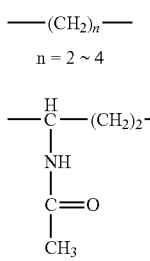

<14> The organopolysiloxane graft polymer according to any one of the above aspects <1> to <13>, wherein the repeating unit derived from the unsaturated monomer containing a carboxylic acid or a carboxylic acid salt is a repeating unit derived from at least one unsaturated monomer selected from the group consisting of (meth) acrylic acid, maleic acid, maleic anhydride, itaconic acid, fumaric acid and crotonic acid, preferably a repeating unit derived from at least one unsaturated monomer selected from the group consisting of (meth)acrylic acid and maleic acid, and more preferably a repeating unit derived from (meth)acrylic acid.

<15> The organopolysiloxane graft polymer according to any one of the above aspects <1> to <14>, wherein a content of the organopolysiloxane segment in the organopolysiloxane graft polymer is preferably not less than 38% by mass, more preferably not less than 40% by mass, and still more preferably not less than 45% by mass, and is also preferably not more than 55% by mass, and more preferably not more than 50% by mass.

<16> The organopolysiloxane graft polymer according to any one of the above aspects <1> to <15>, wherein a content of the unsaturated monomer-derived copolymer segment in the organopolysiloxane graft polymer is not less than 41% by mass, preferably not less than 45% by mass, and more preferably not less than 50% by mass, and is also not more than 65% by mass, preferably not more than 62% by mass, more preferably not more than 60% by mass, and still more preferably not more than 55% by mass.

<17> The organopolysiloxane graft polymer according to any one of the above aspects <1> to <16>, wherein a content of the repeating unit derived from the unsaturated monomer containing a carboxylic acid or a carboxylic acid salt in the organopolysiloxane graft polymer is preferably not less than 4.5% by mass, and more preferably not less than 8% by mass, and is also preferably not more than 14% by mass, more preferably not more than 11% by mass, and still more preferably not more than 9% by mass.

<18> The organopolysiloxane graft polymer according to any one of the above aspects <1> to <17>, wherein a content of the repeating unit derived from the unsaturated monomer containing a carboxylic acid or a carboxylic acid salt in the unsaturated monomer-derived copolymer segment is preferably not less than 6% by mass, more preferably not less than 10% by mass, and still more preferably not less than 17% by mass, and is also preferably not more than 41% by mass, more preferably not more than 30% by mass, still more preferably not more than 25% by mass, and even still more preferably not more than 18% by mass.

<19> The organopolysiloxane graft polymer according to any one of the above aspects <1> to <18>, wherein a content of a repeating unit derived from an unsaturated monomer whose homopolymer has a glass transition point of not lower than 150° C. (except for the unsaturated monomer containing a carboxylic acid or a carboxylic acid salt) in the organopolysiloxane graft polymer is preferably not more than 12% by mass, more preferably not more than 10% by mass, and still more preferably not more than 5% by mass.

<20> The organopolysiloxane graft polymer according to any one of the above aspects <1> to <19>, wherein the unsaturated monomer-derived copolymer segment containing the repeating unit derived from the unsaturated monomer containing a carboxylic acid or a carboxylic acid salt contains a repeating unit derived from an unsaturated monomer that is copolymerizable with the unsaturated monomer containing a carboxylic acid or a carboxylic acid salt in addition to the repeating unit derived from the unsaturated monomer containing a carboxylic acid or a carboxylic acid salt.

<21> The organopolysiloxane graft polymer according to the above aspect <20>, wherein the repeating unit derived from the unsaturated monomer that is copolymerizable with the unsaturated monomer containing a carboxylic acid or a carboxylic acid salt is a repeating unit derived from an unsaturated monomer containing no ionic group, preferably a repeating unit derived from at least one unsaturated monomer selected from the group consisting of olefins, halogenated olefins, vinyl esters, (meth)acrylic acid esters and (meth)acrylamides, and more preferably a repeating unit derived from at least one unsaturated monomer selected from the group consisting of (meth)acrylamides and (meth)acrylic acid esters.

<22> The organopolysiloxane graft polymer according to the above aspect <20> or <21>, wherein a content of the repeating unit derived from the unsaturated monomer that is copolymerizable with the unsaturated monomer containing a carboxylic acid or a carboxylic acid salt in the organopolysiloxane graft polymer is preferably not less than 24% by mass, and more preferably not less than 28% by mass, and is also preferably not more than 61% by mass, and more preferably not more than 55% by mass.

<23> The organopolysiloxane graft polymer according to any one of the above aspects <20> to <22>, wherein a content of the repeating unit derived from the unsaturated monomer that is copolymerizable with the unsaturated monomer containing a carboxylic acid or a carboxylic acid salt in the unsaturated monomer-derived copolymer segment is preferably not less than 59% by mass, more preferably not less than 65% by mass, still more preferably not less than 70% by mass, and even still more preferably not less than 82% by mass, and is also preferably not more than 94% by mass, more preferably not more than 90% by mass, and still more preferably not more than 83% by mass.

<24> The organopolysiloxane graft polymer according to any one of the above aspects <1> to <23>, wherein a mass ratio (a/b) of the organopolysiloxane segment (a) to the unsaturated monomer-derived copolymer segment (b) is preferably not less than 35/65, more preferably not less than 38/62, still more preferably not less than 40/60, and even still more preferably not less than 45/55, and is also preferably not more than 59/41, more preferably not more than 55/45, and still more preferably not more than 50/50.

<25> The organopolysiloxane graft polymer according to any one of the above aspects <1> to <24>, wherein a number-average molecular weight (MNt) of the organopolysiloxane graft polymer is preferably not less than 10,000, more preferably not less than 14,000, and still more preferably not less than 20,000, and is also preferably not more than 300,000, more preferably not more than 250,000, still more preferably not more than 100,000, and even still more preferably not more than 50,000.

<26> The organopolysiloxane graft polymer according to any one of the above aspects <1> to <25>, wherein a number-average molecular weight (MNy) of the unsaturated monomer-derived copolymer segment is preferably not less than 500, more preferably not less than 1,000, and still more preferably not less than 1,500, and is also preferably not more than 50,000, more preferably not more than 30,000, and still more preferably not more than 6,000.

<27> The organopolysiloxane graft polymer according to any one of the above aspects <1> to <26>, wherein the organopolysiloxane graft polymer is produced by subjecting unsaturated monomers containing the unsaturated monomer containing a carboxylic acid or a carboxylic acid salt to radical polymerization in the presence of a radical-reactive organopolysiloxane.

<28> The organopolysiloxane graft polymer according to the above aspect <27>, wherein the radical-reactive organopolysiloxane is represented by the following general formula (4) or (5):

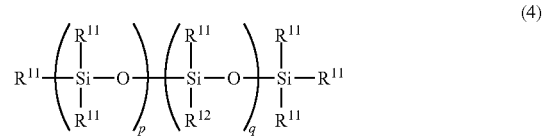

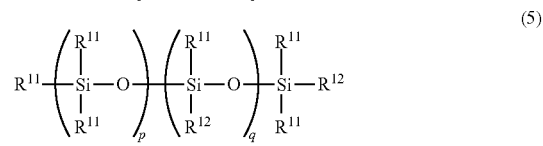

wherein $R^{11}$ groups are each independently an alkyl group having not less than 1 and not more than 22 carbon atoms or an aryl group having not less than 6 and not more than 14 carbon atoms; $R^{12}$ is an alkyl group containing a radical-reactive functional group; p is a number of not less than 2 and not more than 4,000; and q is a number of not less than 2 and not more than 250, in which repeating units in the number of p and repeating units in the number of q may be bonded to each other either in a block form or in a random form.

<29> The organopolysiloxane graft polymer according to the above aspect <28>, wherein the radical-reactive functional group is a group selected from the group consisting of an ethylenically unsaturated group, a halogeno group and a sulfanyl group, and preferably a sulfanyl group.

<30> The organopolysiloxane graft polymer according to the above aspect <28> or <29>, wherein in the above general formulae (4) and (5), $R^{11}$ is a straight-chain or branched-chain alkyl group having not less than 1 and not more than 6 carbon atoms, preferably a straight-chain or branched-chain alkyl group having not less than 1 and not more than 3 carbon atoms, and more preferably a methyl group.

<31> The organopolysiloxane graft polymer according to any one of the above aspects <28> to <30>, wherein in the above general formulae (4) and (5), p is preferably a number of not less than 50, more preferably not less than 60, still more preferably not less than 80, and even still more preferably not less than 100, and is also preferably a number of not more than 1,500, more preferably not more than 1,300, still more preferably not more than 900, even still more preferably not more than 500, and further even still more preferably not more than 200.

<32> The organopolysiloxane graft polymer according to any one of the above aspects <28> to <31>, wherein in the general formulae (4) and (5), q is preferably a number of not less than 3, and is also preferably a number of not more than 150, more preferably not more than 110, still more preferably not more than 70, even still more preferably not more than 20, and further even still more preferably not more than 10.

<33> The organopolysiloxane graft polymer according to any one of the above aspects <28> to <32>, wherein in the general formulae (4) and (5), the number of carbon atoms of the radical-reactive group-containing alkyl group represented by $R^{12}$ is preferably not less than 2, and more preferably not less than 3, and is also preferably not more than 20, more preferably not more than 10, and still more preferably not more than 8.

<34> The organopolysiloxane graft polymer according to any one of the above aspects <28> to <33>, wherein in the general formulae (4) and (5), the radical-reactive group-containing alkyl group represented by $R^{12}$ is interrupted by at least one atom or functional group selected from the group consisting of an oxygen atom, a sulfur atom, —NH—, —COO—, —NHCO— and —NR$^{13}$CO—.

<35> The organopolysiloxane graft polymer according to any one of the above aspects <28> to <34>, wherein in the general formulae (4) and (5), the radical-reactive group-containing alkyl group represented by $R^{12}$ is a group selected from the group consisting of those groups represented by the following formulae (xvii) to (xx), and preferably a group represented by the following formula (xix) or (xx);

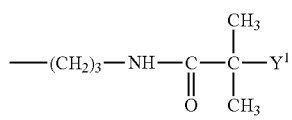
(xvii)

$Y^1$ = Cl or Br

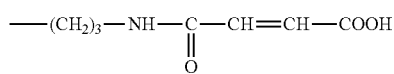
(xviii)

(xix)

(xx)

wherein $X^{11}$ in the formula (xx) is an atom or group selected from the group consisting of —O—, —OCO—, —COO—, —CONH—, and —NHCO—; and WA in the formula (xx) is an alkylene group that may be substituted with at least one substituent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having 2 to 4 carbon atoms, a carboxy group and a ($C_1$-$C_3$) alkyl ester group, and preferably an alkylene group that may be substituted with an acetamide group, a ($C_1$-$C_3$) alkyl amino group or an amino group.

<36> The organopolysiloxane graft polymer according to any one of the above aspects <27> to <35>, wherein the number of moles of the radical-reactive functional group being present per a unit mass of the radical-reactive organopolysiloxane is preferably not more than 1/500 mol/g, more preferably not more than 1/700 mol/g, still more preferably not more than 1/1,000 mol/g, and even still more preferably not more than 1/1,500 mol/g, and is also preferably not less than 1/30,000 mol/g, more preferably not less than 1/20,000 mol/g, still more preferably not less than 1/10,000 mol/g, and even still more preferably not less than 1/4,000 mol/g.

<37> The organopolysiloxane graft polymer according to any one of the above aspects <27> to <36>, wherein a number-average molecular weight of the radical-reactive organopolysiloxane is not less than 8,000, preferably not less than 10,000, more preferably not less than 11,000, and still more preferably not less than 12,000, and is also not more than 200,000, preferably not more than 100,000, more preferably not more than 50,000, and still more preferably not more than 30,000.

<38> The organopolysiloxane graft polymer according to any one of the above aspects <27> to <37>, wherein the radical-reactive organopolysiloxane is produced by reacting a reactive functional group-containing organopolysiloxane with a radical reactivity-imparting agent.

<39> The organopolysiloxane graft polymer according to any one of the above aspects <27> to <38>, wherein the radical-reactive organopolysiloxane is produced by reacting a reactive functional group-containing organopolysiloxane represented by the following general formula (6) or (7) with a radical reactivity-imparting agent:

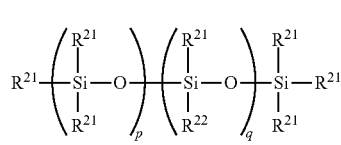
(6)

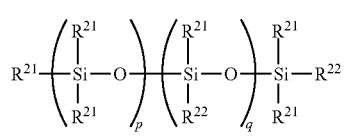
(7)

wherein $R^{21}$ groups are each independently an alkyl group having not less than 1 and not more than 22 carbon atoms or an aryl group having not less than 6 and not more than 14 carbon atoms; $R^{22}$ is an alkyl group containing a reactive functional group; p is a number of not less than 2 and not more than 4,000; and q is a number of not less than 2 and not more than 250, in which repeating units in the number of p and repeating units in the number of q may be bonded to each other either in a block form or in a random form.

<40> The organopolysiloxane graft polymer according to the above aspect <38> or <39>, wherein the reactive functional group is a group selected from the group consisting of a hydroxyl group, an amino group, a carboxy group and an epoxy group, preferably a group selected from the group consisting of a hydroxyl group, an amino group and an epoxy group, and more preferably an amino group.

<41> The organopolysiloxane graft polymer according to the above aspect <39> or <40>, wherein in the above general formulae (6) and (7), $R^{21}$ is a straight-chain or branched-chain alkyl group having not less than 1 and not more than 6 carbon atoms, preferably a straight-chain or branched-chain alkyl group having not less than 1 and not more than 3 carbon atoms, and more preferably a methyl group.

<42> The organopolysiloxane graft polymer according to any one of the above aspects <39> to <41>, wherein in the above general formulae (6) and (7), p is preferably a number of not less than 50, more preferably not less than 60, still more preferably not less than 80, and even more preferably not less than 100, and is also preferably a number of not more than 1,500, more preferably not more than 1,300, still more preferably not more than 900, even still more preferably not more than 500, and further even still more preferably not more than 200.

<43> The organopolysiloxane graft polymer according to any one of the above aspects <39> to <42>, wherein in the general formulae (6) and (7), q is preferably a number of not less than 3, and is also preferably a number of not more than 150, more preferably not more than 110, still more preferably not more than 70, even still more preferably not more than 20, and further even still more preferably not more than 10.

<44> The organopolysiloxane graft polymer according to any one of the above aspect <39> to <43>, wherein in the general formulae (6) and (7), the number of carbon atoms of the reactive group-containing alkyl group represented by $R^{22}$ is preferably not less than 2, and more preferably not less than 3, and is also preferably not more than 15, more preferably not more than 10, and still more preferably not more than 5.

<45> The organopolysiloxane graft polymer according to any one of the above aspects <39> to <44>, wherein in the general formulae (6) and (7), the reactive group-containing alkyl group represented by $R^{22}$ is a group selected from the group consisting of those groups represented by the above formulae (xxi) to (xxviii), preferably a group selected from the group consisting of those groups represented by the above formulae (xxi) to (xxiv), and more preferably a group represented by the above formula (xxiv).

<46> The organopolysiloxane graft polymer according to any one of the above aspects <38> to <45>, wherein a number-average molecular weight of the reactive functional group-containing organopolysiloxane is preferably not less than 8,000, more preferably not less than 10,000, still more preferably not less than 11,000, and even still more preferably not less than 12,000, and is also preferably not more than 200,000, more preferably not more than 100,000, still more preferably not more than 50,000, and even still more preferably not more than 30,000.

<47> The organopolysiloxane graft polymer according to any one of the above aspects <38> to <46>, wherein the number of moles of the reactive functional group being present per a unit mass of the reactive functional group-containing organopolysiloxane is preferably not more than 1/500 mol/g, more preferably not more than 1/700 mol/g, still more preferably not more than 1/1,000 mol/g, and even still more preferably not more than 1/1,500 mol/g, and is also preferably not less than 1/30,000 mol/g, more preferably not less than 1/20,000 mol/g, still more preferably not less than 1/10,000, and even still more preferably not less than 1/4,000.

<48> The organopolysiloxane graft polymer according to any one of the above aspects <38> to <47>, wherein the radical reactivity-imparting agent is a compound containing a radical-reactive functional group and at least one functional group selected from the group consisting of a carboxy group, an ester group, an epoxy group, a hydroxyl group and lactones, in a molecule thereof, or an unsubstituted or substituted thiolactone.

<49> The organopolysiloxane graft polymer according to the above aspect <48>, wherein the radical-reactive functional group of the radical reactivity-imparting agent is a group selected from the group consisting of an ethylenically unsaturated group, a halogeno group and a sulfanyl group, and preferably a sulfanyl group.

<50> The organopolysiloxane graft polymer according to any one of the above aspects <38> to <49>, wherein the radical reactivity-imparting agent is at least one compound selected from the group consisting of 3-mercapto propionic acid, γ-butyrolactone thiol, γ-thiobutyrolactone, N-acetyl-DL-homocysteine thiolactone and DL-homocysteine thiolactone hydrochloride, and preferably N-acetyl-DL-homocysteine thiolactone.

<51> The organopolysiloxane graft polymer according to any one of the above aspects <38> to <50>, wherein an amount of the radical reactivity-imparting agent used is preferably not less than 0.8 equivalent, and more preferably not less than 0.9 equivalent, and is also preferably not more than 1.2 equivalent, and more preferably not more than 1.1 equivalent.

<52> The organopolysiloxane graft polymer according to any one of the above aspects <1> to <51>, wherein it is preferred that a content of the organopolysiloxane segment in the graft polymer is not less than 45% by mass and not more than 59% by mass, a content of the repeating unit derived from the unsaturated monomer containing a carboxylic acid or a carboxylic acid salt in the graft polymer is not less than 4% by mass and not more than 9% by mass, and a content of the repeating unit derived from the copolymerizable monomer in the graft polymer is not less than 32% by mass and not more than 51% by mass, and it is more preferred that a content of the organopolysiloxane segment in the graft polymer is not less than 50% by mass and not more than 59% by mass, a content of the repeating unit derived from the unsaturated monomer containing a carboxylic acid or a carboxylic acid salt in the graft polymer is not less than 5% by mass and not more than 7% by mass, and a content of the repeating unit derived from the copolymerizable monomer in the graft polymer is not less than 34% by mass and not more than 45% by mass.

<53> The organopolysiloxane graft polymer according to any one of the above aspects <1> to <51>, wherein it is preferred that a content of the organopolysiloxane segment in the graft polymer is not less than 45% by mass and not more than 59% by mass, a content of the repeating unit derived from the unsaturated monomer containing a carboxylic acid or a carboxylic acid salt in the graft polymer is not less than 8% by mass and not more than 17% by mass, and a content of the repeating unit derived from the copolymerizable monomer in the graft polymer is not less than 24% by mass and not more than 47% by mass, and it is more preferred that a content of the organopolysiloxane segment in the graft polymer is not less than 50% by mass and not more than 59% by mass, a content of the repeating unit derived from the unsaturated monomer containing a carboxylic acid or a carboxylic acid salt in the graft polymer is not less than 10% by mass and not more than 15% by mass, and a content of the repeating unit derived from the copolymerizable monomer in the graft polymer is not less than 24% by mass and not more than 40% by mass.

<54> The organopolysiloxane graft polymer according to any one of the above aspects <1> to <51>, wherein the organopolysiloxane graft polymer is preferably produced by reacting not less than 45% by mass and not more than 59% by mass of the radical-reactive organopolysiloxane, not less than 4% by mass and not more than 9% by mass of the unsaturated monomer containing a carboxylic acid or a carboxylic acid salt, and not less than 32% by mass and not more than 51% by mass of the copolymerizable monomer, on the basis of a total mass of the radical-reactive organopolysiloxane and the unsaturated monomers, and more preferably produced by reacting not less than 50% by mass and not more than 59% by mass of the radical-reactive organopolysiloxane, not less than 5% by mass and not more than 7% by mass of the unsaturated monomer containing a carboxylic acid or a carboxylic acid salt, and not less than 34% by mass and not more than 45% by mass of the copolymerizable monomer, on the basis of a total mass of the radical-reactive organopolysiloxane and the unsaturated monomers.

<55> The organopolysiloxane graft polymer according to any one of the above aspects <1> to <51>, wherein the organopolysiloxane graft polymer is preferably produced by reacting not less than 45% by mass and not more than 59% by mass of the radical-reactive organopolysiloxane, not less than 8% by mass and not more than 17% by mass of the unsaturated monomer containing a carboxylic acid or a carboxylic acid salt, and not less than 24% by mass and not more than 47% by mass of the copolymerizable monomer, on the basis of a total mass of the radical-reactive organopolysiloxane and the unsaturated monomers, and more preferably produced by reacting not less than 50% by mass and not more than 59% by mass of the radical-reactive organopolysiloxane, not less than 10% by mass and not more than 15% by mass of the unsaturated monomer containing a carboxylic acid or a carboxylic acid salt, and not less than 26% by mass and not more than 40% by mass of the copolymerizable monomer, on the basis of a total mass of the radical-reactive organopolysiloxane and the unsaturated monomers.

<56> A process for producing the organopolysiloxane graft polymer according to any one of the above aspects <1> to <55>, said process including the step of subjecting unsaturated monomers containing the unsaturated monomer containing a carboxylic acid or a carboxylic acid salt to radical polymerization in the presence of the radical-reactive organopolysiloxane.

<57> The process for producing the organopolysiloxane graft polymer according to the above aspect <56>, wherein the polymerization is a solution polymerization that is carried out in the presence of a solvent.

<58> The process for producing the organopolysiloxane graft polymer according to the above aspect <56> or <57>, wherein an amount of the radical-reactive organopolysiloxane used therein is preferably not less than 35% by mass, more preferably not less than 38% by mass, still more preferably not less than 40% by mass, and even still more preferably not less than 45% by mass, and is also preferably not more than 59% by mass, more preferably not more than 55% by mass, and still more preferably not more than 50% by mass, on the basis of a total mass of the radical-reactive organopolysiloxane and the unsaturated monomers as the raw materials.

<59> The process for producing the organopolysiloxane graft polymer according to any one of the above aspects <56> to <58>, wherein an amount of the unsaturated monomers used therein is preferably not less than 41% by mass, more preferably not less than 45% by mass, and still more preferably not less than 50% by mass, and is also preferably not more than 65% by mass, more preferably not more than 62% by mass, still more preferably not more than 60% by mass, and even still more preferably not more than 55% by mass, on the basis of a total mass of the radical-reactive organopolysiloxane and the unsaturated monomers as the raw materials.

<60> The process for producing the organopolysiloxane graft polymer according to any one of the above aspects <56> to <59>, wherein an amount of the unsaturated monomer containing a carboxylic acid or a carboxylic acid salt used therein is preferably not less than 4.0% by mass, more preferably not less than 4.5% by mass, and still more preferably not less than 8% by mass, and is also preferably not more than 17% by mass, more preferably not more than 14% by mass, still more preferably not more than 11% by mass, and even still more preferably not more than 9% by mass, on the basis of a total mass of the radical-reactive organopolysiloxane and the unsaturated monomers as the raw materials.

<61> The process for producing the organopolysiloxane graft polymer according to any one of the above aspects <56> to <60>, wherein an amount of the copolymerizable monomer used therein is preferably not less than 24% by mass, and more preferably not less than 28% by mass, and is also preferably not more than 61% by mass, and more preferably not more than 55% by mass, on the basis of a total mass of the radical-reactive organopolysiloxane and the unsaturated monomers as the raw materials.

<62> The process for producing the organopolysiloxane graft polymer according to any one of the above aspects <56> to <61>, wherein an amount of the unsaturated monomer having Tg for unsaturated monomer of not lower than 150° C. (except for the unsaturated monomer containing a carboxylic acid or a carboxylic acid salt) used therein is preferably not more than 14% by mass, more preferably not more than 12% by mass, still more preferably not more than 10% by mass, and even still more preferably not more than 5% by mass, on the basis of a total mass of the radical-reactive organopolysiloxane and the unsaturated monomers as the raw materials, and a lower limit of the amount of the unsaturated monomer having Tg for unsaturated monomer of not lower than 150° C. used therein is 0% by mass.

<63> The process for producing the organopolysiloxane graft polymer according to any one of the above aspects <56> to <62>, wherein it is preferred that an amount of the radical-reactive organopolysiloxane used therein is not less than 45% by mass and not more than 59% by mass, an amount of the unsaturated monomer containing a carboxylic acid or a carboxylic acid salt used therein is not less than 4% by mass and not more than 9% by mass, and an amount of the copolymerizable monomer used therein is not less than 32% by mass and not more than 51% by mass, on the basis of a total mass of the radical-reactive organopolysiloxane and the unsaturated monomers, and it is more preferred that an amount of the radical-reactive organopolysiloxane used therein is not less than 50% by mass and not more than 59% by mass, an amount of the unsaturated monomer containing a carboxylic acid or a carboxylic acid salt used therein is not less than 5% by mass and not more than 7% by mass, and an amount of the copolymerizable monomer used therein is not less than 34% by mass and not more than 45% by mass, on the basis of a total mass of the radical-reactive organopolysiloxane and the unsaturated monomers.

<64> The process for producing the organopolysiloxane graft polymer according to any one of the above aspects <56> to <63>, wherein it is preferred that an amount of the radical-reactive organopolysiloxane used therein is not less than 45% by mass and not more than 59% by mass, an amount of the unsaturated monomer containing a carboxylic acid or a carboxylic acid salt used therein is not less than 8% by mass and not more than 17% by mass, and an amount of the copolymerizable monomer used therein is not less than 24% by mass and not more than 47% by mass, on the basis of a total mass of the radical-reactive organopolysiloxane and the unsaturated monomers, and it is more preferred that an amount of the radical-reactive organopolysiloxane used therein is not less than 50% by mass and not more than 59% by mass, an amount of the unsaturated monomer containing a carboxylic acid or a carboxylic acid salt used therein is not less than 10% by mass and not more than 15% by mass, and an amount of the copolymerizable monomer used therein is not less than 26% by mass and not more than 40% by mass, on the basis of a total mass of the radical-reactive organopolysiloxane and the unsaturated monomers.

<65> The process for producing the organopolysiloxane graft polymer according to any one of the above aspects <56> to <64>, wherein the solvent is at least one solvent selected from the group consisting of water, alcohols having not less than 1 and not more than 8 carbon atoms, esters having not less than 2 and not more than 8 carbon atoms and ethers having not less than 2 and not more than 8 carbon atoms; and preferably at least one solvent selected from the group consisting of water and alcohols having not less than 1 and not more than 3 carbon atoms.

<66> The process for producing the organopolysiloxane graft polymer according to any one of the above aspects <56> to <65>, wherein an amount of the solvent used therein is preferably not less than 20% by mass, more preferably not less than 40% by mass, still more preferably not less than 60% by mass, and even still more preferably not less than 100% by mass, and is also preferably not more than 1,000% by mass, more preferably not more than 900% by mass, still more preferably not more than 400% by mass, and even still more preferably not more than 300% by mass, on the basis of a total mass of the radical-reactive organopolysiloxane and the unsaturated monomers.

<67> The process for producing the organopolysiloxane graft polymer according to any one of the above aspects <56> to <66>, wherein the polymerization is carried out in the presence of a polymerization initiator; preferably a polymerization initiator selected from the group consisting of azo-based initiators, peroxide-based initiators and persulfate-based initiators; more preferably a polymerization initiator selected from the group consisting of 2,2'-azobisisobutyronitrile, 2,2'-azobis(2,4-dimethyl valeronitrile), lauroyl peroxide, benzoyl peroxide and ammonium persulfate; and still more preferably 2,2'-azobis(2,4-dimethyl valeronitrile).

<68> The process for producing the organopolysiloxane graft polymer according to any one of the above aspects <56> to <67>, wherein an amount of the polymerization initiator used therein is preferably not more than 10% by mass, more preferably not more than 5% by mass, still more preferably not more than 2% by mass, and even still more preferably not more than 1% by mass, and is also preferably not less than 0.001% by mass, more preferably not less than 0.01% by mass, still more preferably not less than 0.1% by mass, and even still more preferably not less than 0.5% by mass, on the basis of a total mass of the unsaturated monomers charged.

<69> The process for producing the organopolysiloxane graft polymer according to any one of the above aspects <56> to <68>, wherein the polymerization reaction is carried out until a conversion rate of the unsaturated monomers reaches not less than 80%, and preferably not less than 90%.

<70> The process for producing the organopolysiloxane graft polymer according to any one of the above aspects <56> to <69>, wherein the polymerization reaction time is not less than 0.1 h, preferably not less than 0.5 h, more preferably not less than 1 h, still more preferably not less than 2 h, and even still more preferably not less than 4 h, and is also not more than 60 h, preferably not more than 30 h, more preferably not more than 20 h, and still more preferably not more than 10 h.

<71> The process for producing the organopolysiloxane graft polymer according to any one of the above aspects <56> to <70>, wherein the radical-reactive organopolysiloxane is produced by reacting the reactive functional group-containing organopolysiloxane with the radical reactivity-imparting agent.

<72> The process for producing the organopolysiloxane graft polymer according to the above aspect <71>, wherein a time of the reaction between the reactive functional group-containing organopolysiloxane and the radical reactivity-imparting agent is preferably not less than 1 h, and more preferably not less than 2 h, and is also preferably not more than 10 h, and more preferably not more than 5 h.

<73> The process for producing the organopolysiloxane graft polymer according to the above aspect <71> or <72>, wherein a temperature of the reaction between the reactive functional group-containing organopolysiloxane and the radical reactivity-imparting agent is preferably not lower than 70° C., and more preferably not lower than 90° C., and is also preferably not higher than 200° C., more preferably not higher than 150° C., and still more preferably not higher than 120° C.

<74> The process for producing the organopolysiloxane graft polymer according to any one of the above aspect <71> to <73>, wherein the reaction between the reactive functional group-containing organopolysiloxane and the radical reactivity-imparting agent is carried out until a conversion rate of at least one of the reactive functional group of the reactive functional group-containing organopolysiloxane and the radical reactivity-imparting agent reaches preferably not less than 80%, and more preferably not less than 90%.

<75> A process for producing an organopolysiloxane graft polymer including an organopolysiloxane segment as a main chain thereof and an unsaturated monomer-derived copolymer segment containing a repeating unit derived from an unsaturated monomer containing a carboxylic acid or a carboxylic acid salt as a side chain thereof, said process including the step of subjecting unsaturated monomers containing the unsaturated monomer containing a carboxylic acid or a carboxylic acid salt to polymerization in the presence of a radical-reactive organopolysiloxane represented by the following general formula (4) or (5):

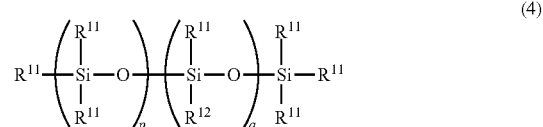

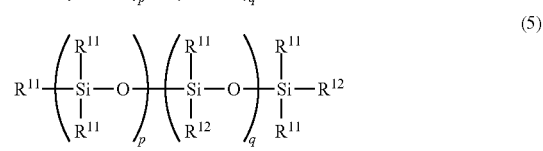

wherein $R^{11}$ groups are each independently an alkyl group having not less than 1 and not more than 22 carbon atoms or an aryl group having not less than 6 and not more than 14 carbon atoms; $R^{12}$ is an alkyl group containing a radical-reactive functional group; p is a number of not less than 2 and not more than 4,000; and q is a number of not less than 2 and not more than 250, in which repeating units in the number of p and repeating units in the number of q may be bonded to each other either in a block form or in a random form, in which a content of the organopolysiloxane segment in the organopolysiloxane graft polymer is not less than 35% by mass and not more than 59% by mass, a content of the repeating unit derived from the unsaturated monomer containing a carboxylic acid or a carboxylic acid salt in the organopolysiloxane graft polymer is not less than 4% by mass and not more than 17% by mass, and a content of a repeating unit derived from an unsaturated monomer whose homopolymer has a glass transition point of not lower than 150° C. (except for the unsaturated monomer containing a carboxylic acid or a carboxylic acid salt) in the organopolysiloxane graft polymer is not more than 14% by mass, and a number-average molecular weight of the organopolysiloxane segment is not less than 8,000 and not more than 200,000.

<76> The process for producing an organopolysiloxane graft polymer according to the above aspect <75>, wherein the radical-reactive organopolysiloxane is produced by reacting a reactive functional group-containing organopolysiloxane represented by the following general formula (6) or (7) with a radical reactivity-imparting agent:

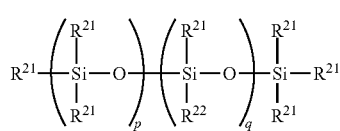

(6)

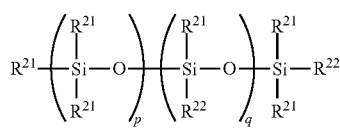

(7)

wherein $R^{21}$ groups are each independently an alkyl group having not less than 1 and not more than 22 carbon atoms or an aryl group having not less than 6 and not more than 14 carbon atoms; $R^{22}$ is an alkyl group containing a reactive functional group; p is a number of not less than 2 and not more than 4,000; and q is a number of not less than 2 and not more than 250, in which repeating units in the number of p and repeating units in the number of q may be bonded to each other either in a block form or in a random form.

<77> A hair cosmetic including the organopolysiloxane graft polymer according to any one of the above aspects <1> to <55>.

<78> A use of the organopolysiloxane graft polymer according to any one of the above aspects <1> to <55>, for a hair cosmetic.

<79> A hairdressing method including the step of applying the organopolysiloxane graft polymer according to any one of the above aspects <1> to <55> to hair.

EXAMPLES

In the following Examples, etc., "%" indicates "% by mass", unless otherwise specified.

<GPC Measuring Conditions of Number-Average Molecular Weights of Reactive Functional Group-Containing Organopolysiloxane and Radical-Reactive Organopolysiloxane)>

Column: "K-804L" (available from Tosoh Corp.); Two columns connected in series were used.

Eluent 1 mM Dimethyl dodecyl amine/chloroform solution

Flow Rate: 1.0 mL/min
Column Temperature: 40° C.
Detector: RI

Concentration and Amount of Sample: 5 mg/mL; 500 μL

Under the above measuring conditions, the number-average molecular weight (MNxm) of the reactive functional group-containing organopolysiloxane or the number-average molecular weight (MNx) of the radical-reactive organopolysiloxane was measured in terms of polystyrene.

<Calculation of Number of Moles of Amino Group per Unit Mass of Side-Chain Primary Aminopropyl-Modified Organopolysiloxane (Reactive Functional Group-Containing Organopolysiloxane)>

The amount of an amino group per a unit mass of a side-chain primary aminopropyl-modified organopolysiloxane was measured by the method according to ASTM D 2073. More specifically, about 10 g of a sample (side-chain primary aminopropyl-modified organopolysiloxane) was weighed and sampled in a flask, and 50 mL of ethanol was added thereto, followed by stirring the contents of the flask. Using a potentiometric titration apparatus, the resulting reaction solution was subjected to titration with a 0.2 mol/L ethanolic hydrochloric acid solution. At the same time, a blank test of the above measurement was conducted to correct the above measured value.

<Calculation of Number of Moles of Sulfanyl Group per Unit Mass of Sulfanyl Group-Modified Organopolysiloxane (Radical-Reactive Organopolysiloxane) Synthesized from Side-Chain Primary Aminopropyl-Modified Organopolysiloxane (Reactive Functional Group-Containing Organopolysiloxane)>

The amount of an amino group contained in a mixture containing a sulfanyl group-modified organopolysiloxane (radical-reactive organopolysiloxane) obtained by the reaction between the side-chain primary aminopropyl-modified organopolysiloxane and a radical reactivity-imparting agent was measured, and an amount of the amino group consumed by the reaction was determined from the thus measured amount of the amino group contained in the mixture and the above-measured amount of the amino group per a unit mass of the side-chain primary aminopropyl-modified organopolysiloxane. The measurement of the amount of the amino group contained in the mixture containing the sulfanyl group-modified organopolysiloxane was carried out in the same manner as in the above measurement of the amount of the amino group per a unit mass of the side-chain primary aminopropyl-modified organopolysiloxane except for using the mixture containing the sulfanyl group-modified organopolysiloxane as the sample.

From the amounts of the amino group thus measured, a conversion rate α (%) of the amino group was first determined from the following formula (IV):

$$\alpha(\%) = [1 - \{a_1 \times (f+g)/(a_0 \times f)\}] \times 100 \qquad (IV).$$

In the above formula (IV), $a_0$ and $a_1$ are the number of moles of the amino group per a unit mass of the side-chain primary aminopropyl-modified organopolysiloxane and the number of moles of the amino group per a unit mass of a reaction mixture obtained after the reaction between the side-chain primary aminopropyl-modified organopolysiloxane and the radical reactivity-imparting agent, respectively; f is a total mass of the side-chain primary aminopropyl-modified organopolysiloxane charged; and g is a total mass of the radical reactivity-imparting agent charged.

Assuming that the radical-reactive organopolysiloxane obtained after the reaction had the same number of sulfanyl groups produced thereon as that of the amino groups consumed by the reaction, the number of moles (5) of the sulfanyl group per a unit mass of the sulfanyl group-modified organopolysiloxane was calculated from the following calculation formula (V):

$$S(\text{mol/g}) = (a_0 \times f \times \sigma/100) / [f + (a_0 \times f \times \alpha/100) \times h] \quad (V).$$

In the above formula (V), $a_0$ and f are respectively the same as $a_0$ and f as defined in the above formula (IV); and h is a molecular weight of the radical reactivity-imparting agent.

<Method of Measuring Residual Rate of Sulfanyl Group (Mercapto Group)>

An ethanol solution containing 0.05 mM of 5,5'-dithiobis(2-nitrobenzoic acid) (available from Wako Pure Chemical Industries, Ltd.) was prepared as a solution A. Also, an ethanol solution containing 4 to 10% by mass of the organopolysiloxane graft polymer obtained in the respective Examples, etc., was prepared as a solution B. A 10 mL screw vial was charged with 100 μL of a borate pH standard solution (pH: 9.18; available from Wako Pure Chemical Industries, Ltd.), 5 mL of the solution A and 1 mL of the solution B, and then capped, followed by mixing the contents of the screw vial by shaking for 5 s. The resulting solution was measured for an absorbance thereof at 412 nm, and a residual amount (S1) of the sulfanyl group in the organopolysiloxane graft polymer was measured from the thus measured absorbance. Then, a residual rate of the sulfanyl group in the obtained product was calculated from the thus measured residual amount (S1) of the sulfanyl group, and further a conversion rate of the sulfanyl group was calculated from the residual rate of the sulfanyl group.

UV Measuring Device: UV visible spectrophotometer (available from Shimadzu Corporation)

Optical Path Length: 1 cm

Residual Amount (S1) of Sulfanyl Group (mol/g) = $(2350 \times 1 + 0.0058)/1000$ Residual Rate of Sulfanyl Group (%) = $S1/S \times (c+d)/c \times 100$ (VI)

Conversion Rate of Sulfanyl Group (%) = 100−[residual rate of sulfanyl group (%)] (VII)

In the above formulae, 1 represents an absorbance at 412 nm as measured using a UV visible spectrophotometer; S represents the number of moles of the sulfanyl group per a unit mass of the sulfanyl group-modified organopolysiloxane; and c and d represent a total mass of the radical-reactive organopolysiloxane charged upon production of the graft polymer and a total mass of the unsaturated monomers charged upon production of the graft polymer, respectively.

<Method of Measuring Conversion Rate of Unsaturated Monomers>

The conversion rate of the respective unsaturated monomers upon the polymerization reaction was determined as follows. That is, the amounts of the unreacted unsaturated monomers were measured by nuclear magnetic resonance ($^1$H-NMR) under the following conditions to calculate a conversion rate thereof.

The organopolysiloxane graft polymer was dissolved in an amount of 2% by mass in deuterochloroform, and the resulting solution was subjected to $^1$H-NMR measurement using a nuclear magnetic resonance ($^1$H-NMR) apparatus "Mercury 400" (available from Varian Inc.) under the following measuring conditions:

Measuring Mode: Proton 1D; Measuring Temperature: room temperature; Integration: 32 frequencies.

Conversion rates of MAA, tBuAA and PEGMA were respectively determined from a ratio between an integrated value of an alkenyl group (5.5 to 6.3 ppm) and an integrated value of an alkyl group or an alkoxy group in the unsaturated monomer-derived polymer segment (a methyl group of MAA: near 0.8 to 1.5 ppm; a tert-butyl group of tBuAA: 1.0 to 1.4 ppm; a methoxy group of PEGMA: near 3.0 to 3.4 ppm).

<Molecular Weight (MNg) Between Graft Points of Organopolysiloxane Graft Polymer>

The number of moles of the sulfanyl group per a unit mass of the radical-reactive organopolysiloxane reacted with the unsaturated monomers was determined from the number of moles of the sulfanyl group per a unit mass of the radical-reactive organopolysiloxane as the raw material and the residual rate of the sulfanyl group as determined in the above <Method of Measuring Residual Rate of Sulfanyl Group>, and the molecular weight between graft points of the organopolysiloxane graft polymer was calculated from an inverse number thereof.

<Number-Average Molecular Weight (MNt) of Organopolysiloxane Graft Polymer>

The number-average molecular weight (MNt) of the organopolysiloxane graft polymer was determined from the number-average molecular weight of the radical-reactive organopolysiloxane and the mass ratio (a/b) of the organopolysiloxane segment (a) to the unsaturated monomer-derived copolymer segment (b) according to the following formula.

Number-Average Molecular Weight of Organopolysiloxane Graft Polymer=Number-Average Molecular Weight of Radical-Reactive Organopolysiloxane×(1+b/a)

<Number-Average Molecular Weight (MNy) of Unsaturated Monomer-Derived Copolymer Segment>

The number-average molecular weight (MNy) of the unsaturated monomer-derived copolymer segment was determined from the molecular weight between graft points of the organopolysiloxane graft polymer, and the mass ratio (a/b) of the organopolysiloxane segment (a) to the unsaturated monomer-derived copolymer segment (b) according to the following formula.

Number-Average Molecular Weight of Unsaturated Monomer-Derived Copolymer Segment=Molecular Weight between Graft Points of Organopolysiloxane Graft Polymer× b/a Synthesis Example 1

Synthesis of Radical-Reactive Organopolysiloxane α

A separable flask equipped with a reflux condenser, a thermometer, a nitrogen inlet tube and a stirrer was charged with 200 g of a side-chain primary aminopropyl-modified organopolysiloxane (available from Dow Corning Toray Co., Ltd.; number of moles of an amino group per a unit mass: 1/1,970 mol/g; 14,000) number-average molecular weight: 14 and 16 g of N-acetyl-DL-homocysteine thiolactone. The contents of the flask were heated to 100° C. and stirred for 3 h in a nitrogen atmosphere, thereby synthesizing a sulfany group-containing radical-reactive organopolysiloxane cc. As a result of subjecting the resulting reaction solution to potentiometric titration measurement to determine a residual amount of an amino group remaining in the reaction solution, it was confirmed that 99% of the amino group of the side-chain primary aminopropyl-modified organopolysiloxane as the raw material was reacted with N-acetyl-DL-homocysteine thiolactone (conversion rate of amino group: 99%). Therefore, the number of moles of the sulfanyl group per a unit mass of the radical-reactive organopolysiloxane cc was 1/2,100 mol/g. As a result of subjecting the radical-reactive organopolysiloxane cc to GPC measurement, it was confirmed that the radical-reactive organopolysiloxane cc had a number-average molecular weight of 14,000.

Synthesis Examples 2 to 4

The same procedure as in Synthesis Example 1 was carried out except for using respective side-chain primary aminopropyl-modified organopolysiloxanes in which the number of moles of an amino group per a unit mass thereof and a number-average molecular weight thereof were changed as shown in Table 1, thereby obtaining radical-reactive organopolysiloxanes 0 to 6.

TABLE 1

| | Synthesis Examples | | | |
|---|---|---|---|---|
| | 1 | 2 | 3 | 4 |
| Radical-reactive organopolysiloxane | α | β | γ | δ |
| Number of moles of amino group per unit mass | 1/1970 | 1/2078 | 1/3630 | 1/19600 |
| Conversion rate κ of amino group (%) | 99 | 98 | 98 | 99 |
| Number of moles of sulfanyl group per unit mass | 1/2100 | 1/2200 | 1/3800 | 1/19600 |
| Number-average molecular weight MNx | 14000 | 10000 | 13000 | 87000 |

Example 1

Synthesis of Organopolysiloxane Graft Polymer A

A separable flask equipped with a reflux condenser, a thermometer, a nitrogen inlet tube and a stirrer was charged with 17 g of ethanol. While stirring ethanol in the flask under reflux at 80° C. in a nitrogen atmosphere, the following solutions (a) and (b) were respectively charged in separate dropping funnels and added dropwise at the same time to the flask over 3 h. Thereafter, while refluxing ethanol, the contents of the flask were stirred for 1 h, and then the following solution (c) was added dropwise to the flask.

Solution (a): Solution prepared by mixing 4.6 g of methacrylic acid (available from Wako Pure Chemical Industries, Ltd.; hereinafter referred to as "MAA"), 27 g of N-tert-butyl acrylamide (available from Wako Pure Chemical Industries, Ltd.; hereinafter referred to as "t-BuAA"), 14 g of polyethylene glycol (9) monomethyl ether methacrylate (available from Nippon Nyukazai Co., Ltd.; hereinafter referred to as "PEGMA") and 110 g of ethanol.

Solution (b): Solution prepared by mixing 30 g of the radical-reactive organopolysiloxane α synthesized in the above Synthesis Example 1, 0.4 g of 2,2'-azobis(2,4-dimethyl valeronitrile) "V-65 B" (available from Wako Pure Chemical Industries, Ltd.; azo-based polymerization initiator) and 30 g of ethanol.

Solution (c): Solution prepared by mixing 0.4 g of 2,2'-azobis(2,4-dimethyl valeronitrile) "V-65B" (available from Wako Pure Chemical Industries, Ltd.; azo-based polymerization initiator) and 20 g of ethanol.

After completion of the dropwise addition, the resulting reaction solution was stirred for 1 h while refluxing ethanol therethrough, and then conversion rates of MAA, tBuAA and PEGMA therein were measured. As a result, it was confirmed that the conversion rates of MAA, tBuAA and PEGMA in the reaction solution were 99%, 95% and 99%, respectively. The reaction solution was allowed to stand and cooled to room temperature, and 4.7 g of aminomethyl propanol (available from Wako Pure Chemical Industries, Ltd.) as a neutralizing agent was added thereto. The total reaction time was 6 h. Ethanol was removed from the reaction mixture at room temperature (25° C.) under reduced pressure (20 kPa) over 4 h, thereby obtaining a mixture containing an organopolysiloxane graft polymer A as a white solid. As a result of measuring a residual rate of a sulfanyl group in the obtained product by the above method, it was confirmed that the residual rate of the sulfanyl group was 1%.

As a result of measuring the number-average molecular weight (MNy) of the unsaturated monomer-derived copolymer segment of the organopolysiloxane graft polymer in the obtained mixture by the above method, it was confirmed that the number-average molecular weight (MNy) was 2,500. Further, the number-average molecular weight (MNt) of the organopolysiloxane graft polymer as calculated was 31,000.

Examples 2 to 9 and Comparative Examples 1 to 4, 7 and 8

Synthesis of Organopolysiloxane Graft Polymers B to I, J to M, P and Q

The same procedure as in Example 1 was repeated except that the kinds and amounts of radical-reactive organopolysiloxanes charged, and the kinds and amounts of unsaturated monomers charged were varied as shown in Table 2, thereby obtaining mixtures containing organopolysiloxane graft polymers B to I, J to M, P and Q, respectively. The numerical values shown in Table 2 represent parts by mass of the respective components charged, assuming that a total mass of the radical-reactive organopolysiloxane and the unsaturated monomers charged was 100 parts by mass.

Meanwhile, as the radical-reactive organopolysiloxane c, there was used a commercially available radical-reactive organopolysiloxane "KF-2001" (available from Shin-Etsu Chemical Co., Ltd.; number of moles of a sulfanyl group per a unit mass: 1/2,000 mol/g; number-average molecular weight: 6,700).

Comparative Example 5

The method described in Example 49 of JP 10-512233A was carried out to thereby obtain an organopolysiloxane graft polymer N.

Comparative Example 6

The method described in Example 5 of JP 2009-161598A was carried out to thereby obtain an organopolysiloxane graft polymer 0.

Comparative Example 9

The method described in Synthesis Example 1 of WO 2011/062210A was carried out to thereby obtain an organopolysiloxane graft polymer R.

The properties of the organopolysiloxane graft polymers obtained in Examples 1 to 9 and Comparative Examples 1 to 9 are shown in Table 3.

TABLE 2

|  |  | Examples | | | | |
| --- | --- | --- | --- | --- | --- | --- |
|  |  | 1 | 2 | 3 | 4 | 5 |
| Raw materials | | | | | | |
| Radical-reactive organopolysiloxane | | | | | | |
| α | Amount charged (part(s) by mass) | 40.0 | | 55.0 | 55.0 | |
|  | Conversion rate (%) | 99.0 | | 99.0 | 99.0 | |
| β | Amount charged (part(s) by mass) | | | | | 40.0 |
|  | Conversion rate (%) | | | | | 99.0 |
| γ | Amount charged (part(s) by mass) | | 40.0 | | | |
|  | Conversion rate (%) | | 99.0 | | | |
| δ | Amount charged (part(s) by mass) | | | | | |
|  | Conversion rate (%) | | | | | |
| ε | Amount charged (part(s) by mass) | | | | | |
|  | Conversion rate (%) | | | | | |
| Unsaturated monomer containing a carboxylic acid or a carboxylic acid salt | | | | | | |
| MAA | Amount charged (part(s) by mass) | 6.0 | 6.0 | 11.3 | | 6.0 |
|  | Conversion rate (%) | 99.0 | 99.0 | 99.0 | | 99.0 |
| AA | Amount charged (part(s) by mass) | | | | 6.8 | |
|  | Conversion rate (%) | | | | 99.0 | |
| Copolymerizable monomer | | | | | | |
| NVP | Amount charged (part(s) by mass) | | | | | |
|  | Conversion rate (%) | | | | | |
| tBuAA | Amount charged (part(s) by mass) | 36.0 | 36.0 | 22.5 | 31.5 | |
|  | Conversion rate (%) | 95.0 | 95.0 | 95.0 | 96.0 | |
| iBuMA | Amount charged (part(s) by mass) | | | | | 54.0 |
|  | Conversion rate (%) | | | | | 99.0 |
| PEGMA | Amount charged (part(s) by mass) | 18.0 | 18.0 | 11.3 | 6.8 | |
|  | Conversion rate (%) | 99.0 | 99.0 | 99.0 | 99.0 | |
| LMA | Amount charged (part(s) by mass) | | | | | |
|  | Conversion rate (%) | | | | | |
| Neutralizing agent | | | | | | |
| AMP | Amount charged (part(s) by mass) | 6.2 | 6.2 | 11.7 | 8.4 | 6.2 |
|  | Polymerization solvent | Ethanol | Ethyl acetate | | Ethanol | |
| Reaction Product | | | | | | |
| Organopolysiloxane graft polymer | | A | B | C | D | E |

|  |  | Examples | | | |
| --- | --- | --- | --- | --- | --- |
|  |  | 6 | 7 | 8 | 9 |
| Raw materials | | | | | |
| Radical-reactive organopolysiloxane | | | | | |
| α | Amount charged (part(s) by mass) | | 40.0 | | 40.0 |
|  | Conversion rate (%) | | 99.0 | | 99.0 |
| β | Amount charged (part(s) by mass) | | | 40.0 | |
|  | Conversion rate (%) | | | 99.0 | |
| γ | Amount charged (part(s) by mass) | | | | |
|  | Conversion rate (%) | | | | |
| δ | Amount charged (part(s) by mass) | 40.0 | | | |
|  | Conversion rate (%) | 99.0 | | | |
| ε | Amount charged (part(s) by mass) | | | | |
|  | Conversion rate (%) | | | | |

TABLE 2-continued

| | | | | | |
|---|---|---|---|---|---|
| Unsaturated monomer containing a carboxylic acid or a carboxylic acid salt | | | | | |
| MAA | Amount charged (part(s) by mass) | 6.0 | 12.0 | 6.0 | |
| | Conversion rate (%) | 99.0 | 99.0 | 99.0 | |
| AA | Amount charged (part(s) by mass) | | | | 12.0 |
| | Conversion rate (%) | | | | 99.0 |
| Copolymerizable monomer | | | | | |
| NVP | Amount charged (part(s) by mass) | | | 9.0 | |
| | Conversion rate (%) | | | 98.0 | |
| tBuAA | Amount charged (part(s) by mass) | 36.0 | | | 36.0 |
| | Conversion rate (%) | 95.0 | | | 95.0 |
| iBuMA | Amount charged (part(s) by mass) | | | | |
| | Conversion rate (%) | | | | |
| PEGMA | Amount charged (part(s) by mass) | 18.0 | | | 12.0 |
| | Conversion rate (%) | 99.0 | | | 99.0 |
| LMA | Amount charged (part(s) by mass) | | 48.0 | 45.0 | |
| | Conversion rate (%) | | 99.0 | 99.0 | |
| Neutralizing agent | | | | | |
| AMP | Amount charged (part(s) by mass) | 6.2 | 12.4 | 6.2 | 14.8 |
| Polymerization solvent | | Ethyl acetate | | Ethanol | |
| Reaction Product | | | | | |
| Organopolysiloxane graft polymer | | F | G | H | I |

| | | Comparative Examples | | | |
|---|---|---|---|---|---|
| | | 1 | 2 | 3 | 4 |
| Raw materials | | | | | |
| Radical-reactive organopolysiloxane | | | | | |
| α | Amount charged (part(s) by mass) | 30.0 | 60.0 | | 40.0 |
| | Conversion rate (%) | 99.0 | 99.0 | | 99.0 |
| β | Amount charged (part(s) by mass) | | | 40.0 | |
| | Conversion rate (%) | | | 99.0 | |
| γ | Amount charged (part(s) by mass) | | | | |
| | Conversion rate (%) | | | | |
| δ | Amount charged (part(s) by mass) | | | | |
| | Conversion rate (%) | | | | |
| ε | Amount charged (part(s) by mass) | | | | |
| | Conversion rate (%) | | | | |
| Unsaturated monomer containing a carboxylic acid or a carboxylic acid salt | | | | | |
| MAA | Amount charged (part(s) by mass) | 14.0 | 8.0 | 18.0 | 12.0 |
| | Conversion rate (%) | 99.0 | 99.0 | 99.0 | 99.0 |
| AA | Amount charged (part(s) by mass) | | | | |
| | Conversion rate (%) | | | | |
| Copolymerizable monomer | | | | | |
| NVP | Amount charged (part(s) by mass) | | | | 18.0 |
| | Conversion rate (%) | | | | 98.0 |
| tBuAA | Amount charged (part(s) by mass) | | | | |
| | Conversion rate (%) | | | | |
| iBuMA | Amount charged (part(s) by mass) | | | | |
| | Conversion rate (%) | | | | |
| PEGMA | Amount charged (part(s) by mass) | | | | |
| | Conversion rate (%) | | | | |
| LMA | Amount charged (part(s) by mass) | 56.0 | 32.0 | 42.0 | 30.0 |
| | Conversion rate (%) | 99.0 | 99.0 | 99.0 | 98.0 |
| MA | Amount charged (part(s) by mass) | | | | |
| | Conversion rate (%) | | | | |
| MMA | Amount charged (part(s) by mass) | | | | |
| | Conversion rate (%) | | | | |
| Neutralizing agent | | | | | |
| AMP | Amount charged (part(s) by mass) | 14.5 | 8.3 | 18.6 | 12.4 |
| $NH_3$ | Amount charged (part(s) by mass) | | | | |

TABLE 2-continued

| Polymerization solvent | | Ethanol | | | |
|---|---|---|---|---|---|
| Reaction Product | | | | | |
| Organopolysiloxane graft polymer | | J | K | L | M |
| | | Comparative Examples | | | |
| | | 5 | 6 | 7 | 8 |
| Raw materials | | | | | |
| Radical-reactive organopolysiloxane | | | | | |
| α | Amount charged (part(s) by mass) | | | | |
| | Conversion rate (%) | | | | |
| β | Amount charged (part(s) by mass) | 27.3 | | | |
| | Conversion rate (%) | 99.0 | | | |
| γ | Amount charged (part(s) by mass) | | | | |
| | Conversion rate (%) | | | | |
| δ | Amount charged (part(s) by mass) | | | | |
| | Conversion rate (%) | | | | |
| ε | Amount charged (part(s) by mass) | | 60.0 | 40.0 | 40.0 |
| | Conversion rate (%) | | 99.0 | 99.0 | 99.0 |
| Unsaturated monomer containing a | | | | | |
| carboxylic acid or a carboxylic acid salt | | | | | |
| MAA | Amount charged (part(s) by mass) | 9.1 | 5.0 | 6.0 | 6.0 |
| | Conversion rate (%) | 99.0 | 99.0 | 99.0 | 99.0 |
| AA | Amount charged (part(s) by mass) | | | | |
| | Conversion rate (%) | | | | |
| Copolymerizable monomer | | | | | |
| NVP | Amount charged (part(s) by mass) | | | | |
| | Conversion rate (%) | | | | |
| tBuAA | Amount charged (part(s) by mass) | | | 36.0 | |
| | Conversion rate (%) | | | 96.0 | |
| iBuMA | Amount charged (part(s) by mass) | | 35.0 | | 54.0 |
| | Conversion rate (%) | | 98.0 | | 99.0 |
| PEGMA | Amount charged (part(s) by mass) | | | 18.0 | |
| | Conversion rate (%) | | | 99.0 | |
| LMA | Amount charged (part(s) by mass) | | | | |
| | Conversion rate (%) | | | | |
| MA | Amount charged (part(s) by mass) | 18.1 | | | |
| | Conversion rate (%) | 99.0 | | | |
| MMA | Amount charged (part(s) by mass) | 45.5 | | | |
| | Conversion rate (%) | 99.0 | | | |
| Neutralizing agent | | | | | |
| AMP | Amount charged (part(s) by mass) | | | 6.2 | 6.2 |
| NH₃ | Amount charged (part(s) by mass) | 2.1 | | | |
| | Polymerization solvent | Methyl ethyl ketone | | Ethyl acetate | Ethyl acetate |
| Reaction Product | | | | | |
| Organopolysiloxane graft polymer | | N | O | P | Q |

Note
MAA: Methacrylic acid;
AA: Acrylic acid;
NVP: N-vinyl pyrrolidone;
tBuAA: N-tert-butyl acrylamide;
iBuMA: Isobutyl methacrylate;
PEGMA: Polyethylene glycol (9) monomethyl ether methacrylate;
LMA: Lauryl methacrylate;
MA: Methyl acrylate;
MMA: Methyl methacrylate;
AMP: Aminomethyl propanol

TABLE 3

| | Examples | | | | | | | | |
|---|---|---|---|---|---|---|---|---|---|
| | 1 Polymer A | 2 Polymer B | 3 Polymer C | 4 Polymer D | 5 Polymer E | 6 Polymer F | 7 Polymer G | 8 Polymer H | 9 Polymer I |
| Organopolysiloxane segment | | | | | | | | | |
| Number-average molecular weight (MNx) | 14000 | 13000 | 14000 | 14000 | 10000 | 87000 | 14000 | 10000 | 14000 |
| Molecular weight between graft points | 2100 | 3800 | 2100 | 2100 | 2200 | 19600 | 2100 | 2200 | 2100 |
| Unsaturated monomer-derived copolymer segment | | | | | | | | | |
| Mass % of repeating unit derived from unsaturated monomer containing carboxylic acid or carboxylic acid salt | 6.0 | 6.0 | 11.3 | 6.8 | 6.0 | 6.0 | 12.0 | 6.0 | 12.0 |
| Mass % of repeating unit derived from copolymerizable monomer | 54.0 | 54.0 | 33.7 | 38.2 | 54.0 | 54.0 | 48.0 | 54.0 | 48.0 |
| Mass % of repeating unit derived from copolymerizable monomer having Tg of 150° C. or higher | 0.0 | 0.0 | 0.0 | 0.0 | 0.0 | 0.0 | 0.0 | 9.0 | 0.0 |
| Number-average molecular weight (MNy) | 3200 | 5700 | 1700 | 1700 | 3300 | 29000 | 3200 | 3300 | 3200 |
| a/b | 40/60 | 40/60 | 55/45 | 55/45 | 40/60 | 40/60 | 40/60 | 40/60 | 40/60 |
| Number-average molecular weight (MNt) of organopolysiloxane graft polymer | 35000 | 33000 | 25000 | 25000 | 25000 | 220000 | 35000 | 25000 | 35000 |

| | Comparative Examples | | | | | | | | |
|---|---|---|---|---|---|---|---|---|---|
| | 1 Polymer J | 2 Polymer K | 3 Polymer L | 4 Polymer M | 5 Polymer N | 6 Polymer O | 7 Polymer P | 8 Polymer Q | 9 Polymer R |
| Organopolysiloxane segment | | | | | | | | | |
| Number-average molecular weight (MNx) | 14000 | 14000 | 10000 | 14000 | 10000 | 6700 | 6700 | 6700 | 14000 |
| Molecular weight between graft points | 2100 | 2100 | 2200 | 2100 | 2200 | 2000 | 2000 | 2000 | 2400 |
| Unsaturated monomer-derived copolymer segment | | | | | | | | | |
| Mass % of repeating unit derived from unsaturated monomer containing carboxylic acid or carboxylic acid salt | 14.0 | 8.0 | 18.0 | 12.0 | 9.1 | 5.0 | 6.0 | 6.0 | — |
| Mass % of repeating unit derived from copolymerizable monomer | 56.0 | 32.0 | 42.0 | 48.0 | 63.6 | 35.0 | 54.0 | 54.0 | — |
| Mass % of repeating unit derived from copolymerizable monomer having Tg of 150° C. or higher | 0.0 | 0.0 | 0.0 | 18.0 | 0.0 | 0.0 | 0.0 | 0.0 | — |
| Number-average molecular weight (MNy) | 4900 | 1400 | 3300 | 3200 | 5900 | 1300 | 3000 | 3000 | — |
| a/b | 30/70 | 60/40 | 40/60 | 40/60 | 27.3/72.7 | 60/40 | 40/60 | 40/60 | 50/50 |
| Number-average molecular weight (MNt) of organopolysiloxane graft polymer | 47000 | 23000 | 25000 | 35000 | 37000 | 11000 | 17000 | 17000 | 28000 |

[Evaluation]
<Elastic Modulus>

The organopolysiloxane graft polymers obtained in Examples 1 to 9 and Comparative Examples 1 to 4, 7 and 8 were used as a sample and measured for an elastic modulus thereof by the following method. Meanwhile, the organopolysiloxane graft polymers obtained in Comparative Examples 5 and 6 were deteriorated in results of the below-mentioned evaluation of <Hair Settability>, and therefore subjected to no measurement of an elastic modulus thereof.

An adequate amount of an ethanol or ethyl acetate solution of the respective organopolysiloxane graft polymers (50% by mass) was cast in a petri dish made of polytetrafluoroethylene, and dried at room temperature for 3 to 5 days under a nitrogen flow. Thereafter, the thus dried polymer was further subjected to drying under reduced pressure at 80° C. for 3 to 8 h, thereby obtaining a light-yellow transparent film having a thickness of about 1 mm. The thus obtained film was cut into a film piece, and the cut film piece was used as a test specimen.

Measuring Apparatus: Dynamic viscoelasticity measuring apparatus "DVA-225" (available from I.T. Keisoku Seigyo K.K.)
Measuring Mode: Shearing mode
Distortion: 0.01 to 0.1%
Frequency: 1 Hz
Size of Sample: (0.6 to 1.5)×(7 to 10)×(5 to 6) mm
Measuring Temperature Range: −50 to 200° C.

The test specimen was measured for an elastic modulus thereof both at room temperature (20° C.) and at an elevated temperature (140° C.). The results are shown in Table 4.

<Softening Point>

The softening point of the test specimen was defined as a temperature at which the elastic modulus as measured at 20° C. was reduced by 45% or more as a result of the above measurement for elastic modulus.

<Hair Settability>

A 5% by mass ethanol solution of a mixture containing the respective organopolysiloxane graft polymers obtained in Examples 1 to 9 and Comparative Examples 1 to 4, 7 and 8 as a sample was prepared, and the thus prepared solution was subjected to evaluation for a hair settability by the following method.

(Evaluation Conditions)

A hair bundle of chemically untreated Caucasian curly hair (width of root portion of hair bundle: 3 cm) having a length of 30 cm and a weight of 6 g was used for the evaluation. The hair bundle was fully wetted with water, and then subjected to towel-drying. Thereafter, 1.2 g of the 5% by mass ethanol solution of each of the organopolysiloxane graft polymers was applied onto the hair bundle, and then the hair bundle was combed alternately from front and back sides thereof 5 times on each side. Next, the hair bundle was completely dried using a dryer. Then, a root portion of the hair bundle was nipped by a flat iron "CREATE ION" (available from CREATE Corporation) heated to 150 to 160° C., and the flat iron was slid over the hair bundle towards a tip end thereof to stretch the hair bundle, and the stretching treatment was repeated 3 times. Thereafter, the similar treatment was further repeated 2 times along with combing. After completing a series of the above treatments, the hair bundle was cooled to room temperature, thereby obtaining a hair bundle for evaluation. The thus obtained hair bundle for evaluation was used to evaluate a hair settability by the following measuring method.

As shown in FIG. 1, after shaping the hair bundle for evaluation, the width of the hair bundle (distance between the leftmost hair and the rightmost hair of the hair bundle) at each of a portion of 15 cm below a root thereof (portion A in FIG. 1; hereinafter also referred to as a "portion A"), a portion of 10 cm above a tip thereof (portion B in FIG. 1; hereinafter also referred to as a "portion B") and a portion of 5 cm above a tip thereof (portion C in FIG. 1; hereinafter also referred to as a "portion C") was measured. A good hair settability means that the width of the portion A of the hair bundle lies within the range of from 3.0 to 4.5 cm, the width of the portion B of the hair bundle lies within the range of from 3.0 to 4.0 cm, and the width of the portion C of the hair bundle lies within the range of from 2.5 to 3.8 cm.

<Touch Feeling>

The organopolysiloxane graft polymers obtained in Examples 1 to 9 and Comparative Example 7 were used as a sample for evaluating a touch feeling of hair. Meanwhile, the organopolysiloxane graft polymers obtained in Comparative Examples 1 to 4 and 8 were deteriorated in results of the above evaluation for hair settability, and therefore subjected to no evaluation for a touch feeling of hair.

The hair bundle for evaluation was obtained by the same method as used in the above evaluation for hair settability. A shaped portion of the hair bundle for evaluation was grasped by a hand to examine a touch feeling (less stiffness and less stickiness) thereof, and conduct a sensory evaluation according the following ratings on the basis of the result of Example 9 as a reference. The evaluation was conducted by three expert panelists to obtain an average value thereof.

(Evaluation Criteria)

5: Very good.
4: Good.
3: Normal (Example 9).
2: Poor.
1: Very poor.

<Water Dispersibility>

The organopolysiloxane graft polymers obtained in Examples 1, 3, 4 and 9 were used as a sample for evaluating a water dispersibility.

(Evaluation Conditions)

A 20 mL screw vial equipped with a stirrer was charged with 0.45 g of each polymer and 0.55 g of ethanol to prepare a homogeneous solution. Thereafter, 9 g of ion-exchanged water was added dropwise to the screw vial to prepare an ion-exchanged water/ethanol dispersion of the polymer. The transmittance (%) of the resulting liquid was measured under the following conditions.

As the transmittance value increases, the water dispersibility of the organopolysiloxane graft polymer becomes more excellent.

Apparatus: UV visible spectrophotometer "UV-3300" (available from Hitachi Ltd.)
Measuring Mode: Transmittance
Measuring Wavelength: 660 nm
Sample: Ion-exchanged water/ethanol dispersion containing 4.5% by weight of the polymer
Optical Path Length: 1 cm These evaluation results are shown in Tables 4 to 6.

TABLE 4

|  | Example 1 | Example 2 | Comparative Example 7 |
|---|---|---|---|
| Polymer | A | B | P |
| Numer-average molecular weight of organopolysiloxane segment | 14000 | 13000 | 6700 |
| Mechanical parameter |  |  |  |
| Softening point (° C.) | 42 | 69 | 49 |
| Elastic modulus (Pa) at 20° C. | $1.2 \times 10^7$ | $4.9 \times 10^6$ | $4.8 \times 10^6$ |
| Elastic modulus (Pa) at 140° C. | $9.4 \times 10^2$ | $6.3 \times 10^3$ | $2.4 \times 10^4$ |
| Hair settability |  |  |  |
| Portion A: width of portion of 15 cm from root of hair (cm) | 3.6 | 4.0 | 3.5 |
| Portion B: width of portion of 10 cm from tip of hair (cm) | 3.5 | 3.5 | 3.3 |
| Portion C: width of portion of 5 cm from tip of hair (cm) | 3.2 | 3.5 | 3.4 |
| Touch feeling | 4.0 | 3.7 | 1.3 |

TABLE 5

|  | Example 5 | Comparative Example 8 |
|---|---|---|
| Polymer | E | Q |
| Number-average molecular weight of organopolysiloxane segment | 10000 | 6700 |
| Mechanical parameter |  |  |
| Softening point (° C.) | 34 | 54 |
| Elastic modulus (Pa) at 20° C. | $4.5 \times 10^7$ | $4.3 \times 10^5$ |
| Elastic modulus (Pa) at 140° C. | $7.7 \times 10^4$ | $1.0 \times 10^2$ |
| Hair settability |  |  |
| Portion A: width of portion of 15 cm from root of hair (cm) | 4.1 | >10 |
| Portion B: width of portion of 10 cm from tip of hair (cm) | 3.5 | >10 |

TABLE 5-continued

|  | Example 5 | Comparative Example 8 |
|---|---|---|
| Portion C: width of portion of 5 cm from tip of hair (cm) | 3.5 | >10 |
| Touch feeling | 3.7 | — | obtained in Comparative Examples 1, 3 and 4, the widths of the portions A, B and C of the respective hair bundles exceeded the above-defined ranges, and therefore it was confirmed that the organopolysiloxane graft polymers J, L and M had an insufficient hair settability. In Comparative Example 2 in which the hair bundle having a largest number of hair fibers was used, the width of the portion A of the hair bundle in which portion the hair bundle was most difficult to

TABLE 6

| | Examples | | | | | | | | |
|---|---|---|---|---|---|---|---|---|---|
| | 1 | 2 | 3 | 4 | 5 | 6 | 7 | 8 | 9 |
| Polymer | A | B | C | D | E | F | G | H | I |
| Mechanical parameter | | | | | | | | | |
| Softening point (° C.) | 42 | 69 | 27 | 75 | 34 | 99 | 35 | 24 | 39 |
| Elastic modulus (Pa) at 20° C. | $1.2 \times 10^7$ | $4.9 \times 10^6$ | $3.8 \times 10^6$ | $3.5 \times 10^7$ | $4.5 \times 10^7$ | $1.3 \times 10^5$ | $3.0 \times 10^6$ | $3.9 \times 10^7$ | $1.0 \times 10^7$ |
| Elastic modulus (Pa) at 140° C. | $9.4 \times 10^2$ | $6.3 \times 10^3$ | $1.1 \times 10^4$ | $5.5 \times 10^4$ | $7.7 \times 10^4$ | $5.1 \times 10^2$ | $3.6 \times 10^2$ | $2.9 \times 10^2$ | $5.5 \times 10^4$ |
| Hair settability | | | | | | | | | |
| Portion A: width of portion of 15 cm from root of hair (cm) | 3.6 | 4.0 | 4.0 | 3.7 | 4.1 | 3.6 | 3.5 | 3.2 | 3.5 |
| Portion B: width of portion of 10 cm from tip of hair (cm) | 3.5 | 3.5 | 3.6 | 3.2 | 3.5 | 3.2 | 3.2 | 3.1 | 3.0 |
| Portion C: width of portion of 5 cm from tip of hair (cm) | 3.2 | 3.5 | 3.4 | 3.1 | 3.5 | 2.9 | 3.0 | 3.1 | 2.5 |
| Touch feeling | 4.0 | 3.7 | 3.7 | 4.7 | 3.7 | 4.0 | 3.7 | 4.0 | 3.0 |
| Water dispersibility | 84.3 | — | 97.7 | 90.4 | — | — | — | — | 94 |

| | Comparative Examples | | | |
|---|---|---|---|---|
| | 1 | 2 | 3 | 4 |
| Polymer | J | K | L | M |
| Mechanical parameter | | | | |
| Softening point (° C.) | 53 | 29 | 85 | 90 |
| Elastic modulus (Pa) at 20° C. | $6.7 \times 10^6$ | $1.1 \times 10^7$ | $2.1 \times 10^7$ | $2.3 \times 10^7$ |
| Elastic modulus (Pa) at 140° C. | $4.2 \times 10^3$ | $3.6 \times 10^3$ | $1.9 \times 10^7$ | $4.1 \times 10^5$ |
| Hair settability | | | | |
| Portion A: width of portion of 15 cm from root of hair (cm) | >10 | 5.5 | >10 | 5.0 |
| Portion B: width of portion of 10 cm from tip of hair (cm) | >10 | 3.5 | >10 | 5.0 |
| Portion C: width of portion of 5 cm from tip of hair (cm) | >10 | 3.0 | >10 | 4.0 |

In Tables 4 and 5, there is shown comparison between the evaluation results of the organopolysiloxane graft polymers that were different in number-average molecular weight of an organopolysiloxane segment therein from each other.

As apparently shown in Tables 4 and 5, it was confirmed that the organopolysiloxane graft polymers obtained in Examples 1, 2 and 6 containing an organopolysiloxane segment having a number-average molecular weight of not less than 8,000 were excellent in hair settability and touch feeling of hair as compared to the organopolysiloxane graft polymers obtained in Comparative Examples 7 and 8 containing an organopolysiloxane segment having a number-average molecular weight of less than 8,000.

In addition, as shown in Table 6, in the hair bundles shaped using the organopolysiloxane graft polymers A to I obtained in the Examples, all of the widths of the portions A, B and C of the respective hair bundles fell within the above-defined ranges, and therefore it was confirmed that the organopolysiloxane graft polymers A to I had a good hair settability. On the other hand, in the hair bundles shaped using the organopolysiloxane graft polymers J, L and M set also exceeded the above-defined range, and it was therefore considered that the organopolysiloxane graft polymer K had an insufficient hair settability. The hair bundles shaped using the organopolysiloxane graft polymers A and J are shown in FIG. 1.

Figure 2:
FIG. 2 is a view showing evaluation results of hair settability in Comparative Examples 5 and 6 (polymers N and O).

Meanwhile, the organopolysiloxane graft polymers N and O obtained in Comparative Examples 5 and 6 were evaluated for their hair settability using a 5% by mass ethanol solution thereof by the same method as described above. The appearance of each of the hair bundles treated with the organopolysiloxane graft polymers N and O, respectively, is shown in FIG. 2. As shown in FIG. 2, it was confirmed that both of the organopolysiloxane graft polymers N and O had an insufficient hair settability.

<Hair Set Retentivity Under High-Humidity Conditions>

Next, the organopolysiloxane graft polymers C, D, E and F obtained in Examples 3 to 6 as typical polymers among the organopolysiloxane graft polymers A to I obtained in Examples 1 to 9 having a good hair settability were subjected to evaluation of a hair set retentivity under high-humidity conditions.

The hair bundle shaped by the same method as described in the above evaluation for <Hair Settability> was suspended such that hair tips thereof faced downwards, and allowed to stand in this state under environmental conditions at a temperature of 25° C. and a relative humidity of 90%. After allowing the hair bundle to stand under the above conditions for 1 h, the degree of change in shape of the hair bundle between before and after the standing test was examined to evaluate a hair set retentivity under high-humidity conditions of the respective polymers. The results are shown in FIG. 3.

Also, the organopolysiloxane graft polymer R obtained in Comparative Example 9 was evaluated for its hair set retentivity under high-humidity conditions by the same method as described above. The results are shown in FIG. 3.

Figure 3:
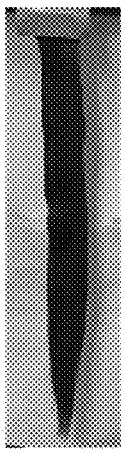
FIG. 3 is a view showing evaluation results of hair set retentivity under high-humidity conditions in Examples 3 to 6 (polymers C to F) and Comparative Example (polymer R).
Figure 3:
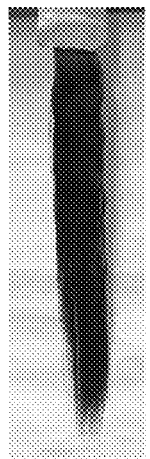
Figure 3:
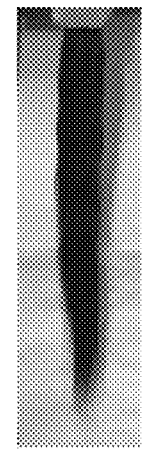
Figure 3:
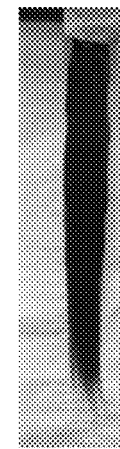
Figure 3:
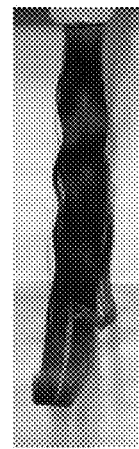

As shown in FIG. 3, it was confirmed that the organopolysiloxane graft polymers C to F according to the present invention all were excellent in hair set retentivity under high-humidity conditions as compared to the polymer R.

INDUSTRIAL APPLICABILITY

The organopolysiloxane graft polymer according to the present invention exhibits an excellent water dispersibility, is optimum for use in a hairdressing method in which a hair is shaped at a hair temperature of 50° C. or higher, and then cooled to a temperature of lower than 50° C. to fix a style of the hair thus shaped, and is excellent in touch feeling of hair after setting and hair set retentivity under high-humidity conditions, and therefore can be usefully used as a hair cosmetic.

The invention claimed is:

1. A hairdressing method comprising:
applying an organopolysiloxane graft polymer to hair, said organopolysiloxane graft polymer comprising:
an organopolysiloxane segment as a main chain of said organopolysiloxane graft polymer, in which a content of the organopolysiloxane segment in the organopolysiloxane graft polymer is not less than 35% by mass and not more than 59% by mass, wherein a number-average molecular weight of the organopolysiloxane segment is not less than 8,000 and not more than 200,000, and
an unsaturated monomer-derived copolymer segment comprising repeating units derived from an unsaturated monomer comprising a carboxylic acid, a carboxylic acid salt, or maleic anhydride as a side chain of said organopolysiloxane graft polymer, in which a content of the unsaturated monomer-derived copolymer segment in the organopolysiloxane graft polymer is not less than 41% by mass, and not more than 65% by mass,
wherein said repeating units of the unsaturated monomer-derived copolymer have a content of a first repeating unit derived from the unsaturated monomer comprising a carboxylic acid, a carboxylic acid salt, or maleic anhydride in the organopolysiloxane graft polymer is not less than 4% by mass and not more than 17% by mass, and
wherein said repeating units of the unsaturated monomer-derived copolymer segment further have a second repeating unit derived from an unsaturated monomer that is copolymerizable with the first repeating unit, and
a content of said second repeating unit derived from an unsaturated monomer whose homopolymer has a glass transition point of not lower than 150° C. in the organopolysiloxane graft polymer is not more than 14% by mass.

2. The hairdressing method comprising the step of applying an organopolysiloxane graft polymer to hair according to claim 1, wherein a number-average molecular weight (MNg) of the organopolysiloxane segment being present between the adjacent unsaturated monomer-derived copolymer segments among the organopolysiloxane segments in the organopolysiloxane graft polymer is not less than 500 and not more than 30,000.

3. The hairdressing method comprising the step of applying an organopolysiloxane graft polymer to hair according to claim 1, wherein the unsaturated monomer-derived copolymer segment further comprises a first repeating unit derived from at least one unsaturated monomer selected from the group consisting of (meth)acrylamides and (meth)acrylates.

4. The hairdressing method comprising the step of applying an organopolysiloxane graft polymer to hair according to claim 1, wherein the first repeating unit derived from the unsaturated monomer comprising a carboxylic acid, a carboxylic acid salt, or maleic anhydride is a repeating unit derived from at least one unsaturated monomer selected from the group consisting of (meth)acrylic acid, maleic acid, maleic anhydride, itaconic acid, fumaric acid and crotonic acid.

5. The hairdressing method comprising the step of applying an organopolysiloxane graft polymer to hair according to claim 1, wherein the organopolysiloxane graft polymer is produced by subjecting unsaturated monomers comprising the unsaturated monomer comprising a carboxylic acid, a carboxylic acid salt, or maleic anhydride to radical polymerization in the presence of a radical-reactive organopolysiloxane represented by the general formula (4) or (5):

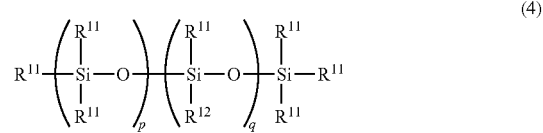

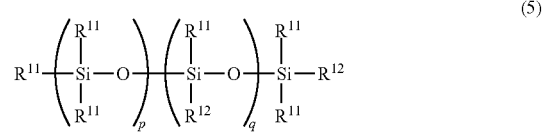

wherein $R^{11}$ groups are each independently an alkyl group having not less than 1 and not more than 22 carbon atoms or an aryl group having not less than 6 and not more than 14 carbon atoms; $R^{12}$ is an alkyl group comprising a radical-reactive functional group; p is a number of not less than 2 and not more than 4,000; and q is a number of not less than 2 and not more than 250, in which repeating units in number of p and repeating units in number of q may be bonded to each other either in a block form or in a random form.

6. The hairdressing method comprising the step of applying an organopolysiloxane graft polymer to hair according to claim 5, wherein the radical-reactive functional group is selected from the group consisting of an ethylenically unsaturated group, a halogeno group and a sulfanyl group.

7. The hairdressing method comprising the step of applying an organopolysiloxane graft polymer to hair according to claim 5, wherein the radical-reactive organopolysiloxane is obtained by reacting a reactive functional group-containing organopolysiloxane represented by the general formula (6) or (7) with a radical reactivity-imparting agent:

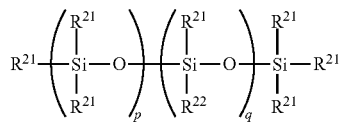  (6)

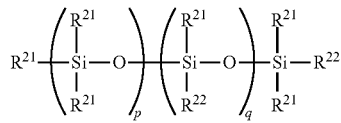  (7)

wherein $R^{21}$ groups are each independently an alkyl group having not less than 1 and not more than 22 carbon atoms or an aryl group having not less than 6 and not more than 14 carbon atoms; $R^{22}$ is an alkyl group comprising a reactive functional group; p is a number of not less than 2 and not more than 4,000; and q is a number of not less than 2 and not more than 250, in which repeating units in number of p and repeating units in number of q may be bonded to each other either in a block form or in a random form.

8. The hairdressing method comprising the step of applying an organopolysiloxane graft polymer to hair according to claim 7, wherein the reactive functional group is selected from the group consisting of a hydroxyl group, an amino group, a carboxy group and an epoxy group.

9. The hairdressing method comprising the step of applying an organopolysiloxane graft polymer to hair according to claim 1, wherein after applying the organopolysiloxane graft polymer to hair, the hair is shaped at a hair temperature of 50° C. or higher and then cooled to a temperature of lower than 50° C.

10. The hairdressing method comprising the step of applying an organopolysiloxane graft polymer to hair according to claim 1, wherein the unsaturated monomer-derived copolymer segment comprises a second repeating unit derived from a (meth)acrylic acid ester.

11. The hairdressing method comprising the step of applying an organopolysiloxane graft polymer to hair according to claim 10, wherein the (meth)acrylic acid ester comprises polyethylene glycol (meth)acrylate.

12. The hairdressing method comprising the step of applying an organopolysiloxane graft polymer to hair according to claim 1, wherein a number average molecular weight of the organopolysiloxane segment constituting the main chain of the graft polymer is 12,000 to 30,000.

13. The hairdressing method comprising the step of applying an organopolysiloxane graft polymer to hair according to claim 1, wherein a mass ratio (a/b) of the organopolysiloxane segment (a) to the unsaturated monomer-derived copolymer segment (b) is 38/62 to 59/41.

14. The hairdressing method comprising the step of applying an organopolysiloxane graft polymer to hair according to claim 1, further comprising a step of neutralizing a carboxylic acid group in a monomer containing the carboxylic acid group with an amine compound.

* * * * *